(12) United States Patent
Young et al.

(10) Patent No.: US 9,068,227 B2
(45) Date of Patent: Jun. 30, 2015

(54) DIAGNOSTIC TEST FOR CARDIOMYOPATHY

(71) Applicant: Genesis Group Inc., St. John's (CA)

(72) Inventors: Terry-Lynn Young, St. John's (CA); Kathy Hodgkinson, St. John's (CA); Sean Connors, St. John's (CA); Patrick Parfrey, St. John's (CA); Annika Haywood, St. John's (CA); Nancy Merner, St. John's (CA); Vanessa French, Torbay (CA)

(73) Assignee: Memorial University of Newfoundland, St. John's, Newfoundland & Labrador (CA)

( * ) Notice: Subject to any disclaimer, the term of this patent is extended or adjusted under 35 U.S.C. 154(b) by 0 days.

(21) Appl. No.: 13/827,705

(22) Filed: Mar. 14, 2013

(65) Prior Publication Data
US 2013/0252836 A1 Sep. 26, 2013

Related U.S. Application Data

(63) Continuation of application No. 12/339,877, filed on Dec. 19, 2008, now Pat. No. 8,409,799.

(60) Provisional application No. 61/016,226, filed on Dec. 21, 2007.

(51) Int. Cl.
| C07H 21/02 | (2006.01) |
| C07H 21/04 | (2006.01) |
| C12Q 1/68 | (2006.01) |
| G01N 33/68 | (2006.01) |

(52) U.S. Cl.
CPC .......... *C12Q 1/6883* (2013.01); *G01N 33/6893* (2013.01); *G01N 2800/325* (2013.01); *G01N 2800/326* (2013.01); *G01N 33/6887* (2013.01); *C12Q 2600/106* (2013.01); *C12Q 2600/156* (2013.01); *C12Q 2600/172* (2013.01)

(58) Field of Classification Search
None
See application file for complete search history.

(56) References Cited

U.S. PATENT DOCUMENTS 5,741,490 A 4/1998 Reyes et al.
6,582,908 B2 * 6/2003 Fodor et al. ................. 506/9

FOREIGN PATENT DOCUMENTS

WO 03027285 3/2003

OTHER PUBLICATIONS

Ahern (The Scientist, vol. 9, pp. 1-5 from the internet; 1995).*
Genbank Accession No. NM_024334; NCBI, NLM; Nov. 2006.*
NEB catalog (1998/1999), pp. 121, 284.*
Database Genbank [Online] Sep. 15, 2006 'Predicted: Pan troglodytes hypothetical LOC460194, transcript variant 3 (LOC460194), mRNA.' Database accession No. XM_516299.
Database Genbank [Online] Aug. 30, 2005 'Predicted: Canis familiaris similar to transmembrane protein 43, transcript variant 1 (LOC484637), mRNA.' Database accession No. XM 541751.
Database Genbank [Online] Sep. 29, 2007 'Mus musculus transmembrane protein 43 (Tmem43), mRNA.' Database accession No. NM_028766.
Database Genbank Nov. 16, 2006 'Predicted: Gallus gallus transmembrane protein 43 (TMEM43), mRNA.' Database accession No. XM_414378.
Database Genbank [Online] Nov. 6, 2002 '*Drosophila melanogaster* CG8111-RA (CG811 1), mRNA.' Database accession No. NM 139905.
Hodgkinson, K.A. et al.: 'The impact of implantable cardioverter-defibrillator therapy on survival in autosomal-dominant arrhythmogenic right ventricular cardiomyopathy (ARVD5).' Journal of the American College of Cardiology vol. 45, No. 3, Feb. 1, 2005, ISSN 0735-1097 pp. 400-408.
Merner, N.D. et al.: 'Arrhythmogenic right ventricular cardiomyopathy type 5 is a fully penetrant, lethal arrhythmic disorder caused by a missense mutation in the TMEM43 gene.' The American Journal of Human Genetics vol. 82, No. 4, Feb. 28, 2008, ISSN 0002-9297 pp. 809-821.
Ahmad, F. et al.: 'Localization of a gene responsible for arrhythmogenic right ventricular dysplasia to chromosome 3p23.' Circulation vol. 98, No. 25, Dec. 22, 1998, ISSN 1524-4539 pp. 2791-2795.
Pilichou Kalliopi et al.: Mutations in desmoglein-2 gene are associated with arrhythmogenic right ventricular cardiomyopathy. Circulation, vol. 113, No. 9, Mar. 2006, pp. 1171-1179.
Mehrle et al., Transmembrane protein 43 (*Homo sapiens*), Gen Bank, NP077310.1, Jun. 3, 2007 (Mar. 6, 2007).
Dreger, Mathias et al. Nuclear envelope proteomics: Novel integral membrane proteins of the inner nuclear membrane, PNAS, Oct. 9, 2001, pp. 11943-11948, vol. 98, No. 21.

(Continued)

*Primary Examiner* — Jehanne Sitton
(74) *Attorney, Agent, or Firm* — Bereskin & Parr LLP; Carmela DeLuca

(57) ABSTRACT

Methods and compositions relating to diagnosing and treating cardiomyopathy and particularly relating to methods and compositions for diagnosing and treating arrhythmogenic right ventricular dysplasia/cardiomyopathy (ARVD/C) are described. Provided are methods for screening for, diagnosing or detecting a risk of developing arrhythmogenic right ventricular dysplasia/cardiomyopathy (ARVD/C) comprising detecting the presence of a transmembrane protein 43 (TMEM43) disease associated variant in a sample of a subject, wherein the presence of a TMEM43 disease variant is indicative that the subject has ARVD/C or an increased risk of developing ARVD/C compared to an individual having wild type TMEM43.

10 Claims, 30 Drawing Sheets

(56) References Cited

OTHER PUBLICATIONS

Bengtsson, Luiza et al. LUMA interacts with emerin and influences its distribution at the inner nuclear membrane, Journal of Cell Science, Nov. 19, 2007, pp. 536-548, 121.
Hegele, Robert A. SNP Judgments and Freedom of Association. Arteriosclerosis, Thrombosis and Vascular Biology, 2002, vol. 22, pp. 1058-1061.
Lucentini, Jack. Gene Association Studies Typically Wrong. The Scientist, 2004, vol. 24, p. 20.
Juppner, H. Functional Properties of the PTH/PTHrP Receptor. Bone, vol. 17, No. 2 Supplement, Aug. 1995, pp. 39S-42S.
Database GeneSeq [Online] Jul. 10, 2008 (Jul. 10, 2008), "Canine osteoarthritis related microarray probe, SEQ ID 84472.", retreived from EBI accession No. GSN:AQG17233 Database Accession No. AQG17233.
Database GeneSeq [Online] Apr. 4, 2000, "Metastatic breast tumour cell upregulated transcript tag #658" XP002525369 Database accession No. AAZ81424.
Sittampalam G. S. et al. High-throughput screening: Advances in assay technologies. Current opinion in chemical biology, vol. 1, Issue 3, Oct. 1997, pp. 384-391.
Database EMBL [Online] Aug. 26, 2008, "Sequence 486533 from patent US 7374927.", retrieved from EBI accession No. EMBL:gc286533 Database accession No. GC286533.
Database EMBL [Online] Dec. 25, 2009, "Sequence 80813 from patent US 7618814.", retrieved from EBI accession No. EMBL:GV080813 Database accession No. GV080813.
Database EMBL [Online] Dec. 25, 2009, "Sequence 318998 from patent US 7618814.", retrieved from EBI accession No. EMBL:GV318998 Database accession No. GV318998.
Database EMBL [Online] Apr. 14, 2007, "Compositions and Methods for the Treatment of Psoriases.", retrieved from EBI accession No. EM_PAT:DD412553 Database accession No. DD412553.

\* cited by examiner

| Gene | Accession | Exon | Variant | Position | AA change | Coordinate | s1 | s2 | s3 | s4 | s5 | s6 | s7 | s8 | s9 | s10 | s11 | s12 | s13 |
|---|---|---|---|---|---|---|---|---|---|---|---|---|---|---|---|---|---|---|---|
| TPRXL | AK092426 | | IVS1-9 ins/delTTT | ATTT microsatellite | | 14079871 | 6 | 5 | 6 | 6 | 8 | 9 | 8 | 6 | 5 | 6 | 8 | 6 | 7 nd |
| TPRXL | AK092426 | | IVS2 +81 A>G | | | 14080090 | A | G | G | A | A | A | A | G | G | G | C | C | C |
| CHCHD4 | NM_144636 | Ex2 | 3'UTR A>C | 5' UTR | | 14129232 | C | C | C | C | C | C | C | T | T | T | T | T | T |
| CHCHD4 | NM_144636 | Ex2 | IVS3 +36 G>C | 160 +36 G>C | | 14132891 | G | G | G | G | G | G | G | G | G | A | A | A | A |
| CHCHD4 | NM_144636 | Ex2 | IVS3 +13 T>C | 160 +13 T>C | | 14132914 | T | T | T | T | T | T | T | T | T | C | C | C | C |
| CHCHD4 | NM_144636 | Ex2 | 5'UTR A>G | | | 14141281 | G | G | G | G | G | G | G | G | G | G | G | G | G |
| TMEM43 | NM_024334 | 4 | IVS3 -106 C>T | 298 -106 C>T | | 14147975 | G | C | C | C | C | C | C | C | C | C | C | C | C |
| TMEM43 | NM_024334 | 5&6 | IVS5 +51 T>C | 442 +51 T>C | | 14149147 | C | C | C | C | C | C | A | A | A | A | A | A | A |
| TMEM43 | NM_024334 | 7 | IVS6 -90 G>A | 513 -90 G>A | | 14150150 | A | A | A | A | A | A | A | A | A | A | A | A | A |
| TMEM43 | NM_024334 | 7 | 536 T>C | | M>T | 14150263 | C | C | C | C | C | C | C | C | C | C | C | C | C |
| TMEM43 | NM_024334 | 8&9 | IVS8 +55 G>A | 705 +55 G>A | | 14151447 | C | C | C | C | C | C | C | C | C | C | C | C | C |
| TMEM43 | NM_024334 | 10 | IVS9 -56 G>A | 781 -56 G>A | | 14152252 | A | A | A | A | A | A | A | A | A | A | A | A | A |
| TMEM43 | NM_024334 | 11 | IVS10 -47 C>T | 883 -47 C>T | | 14155634 | T | T | T | T | T | T | T | T | T | T | T | T | T |
| TMEM43 | NM_024334 | 12a | 1073 C>T | 1203 +115 T>C | S>L | 14158166 | 11 | 13 | 14 | 12 | 11 | 13 | 13 | 11 | 14 | 11 | 11 | 12 | 14 |
| TMEM43 | NM_024334 | 12a | 3'UTR C>T | | | 14158411 | 14 | 13 | 13 | 14 | 14 | 14 | 13 | 13 | nd | nd | 12 | 12 | 14 |
| TMEM43 | NM_024334 | 12b | 3'UTR C>T | | | 14158573 | C | C | C | C | C | C | C | C | C | C | C | C | C |
| TMEM43 | NM_024334 | 12b | 3'UTR A>G | | | 14158759 | A | A | A | A | A | A | A | A | A | A | A | A | A |
| TMEM43 | NM_024334 | 12c | 3'UTR A>C | | | 14159075 | T | T | T | T | T | T | T | T | T | T | T | T | T |
| TMEM43 | NM_024334 | 12d | 3'UTR T>C | | | 14159670 | C | C | C | C | C | C | C | C | C | C | C | C | C |
| TMEM43 | NM_024334 | 12d | 3'UTR T>C | | | 14159720 | A | A | A | A | A | A | A | A | A | A | A | A | A |
| TMEM43 | NM_024334 | 12e | IVS12 +58 ins/del | 1203 +1942 | | 14160264 | A | A | A | A | A | A | A | A | A | A | A | A | A |
| XPC | NM_004628 | 16b | IVS16 +30 ins/del T | 2823 +821 | | 14161621 | G | G | G | G | G | G | G | G | G | G | G | G | G |
| XPC | NM_004628 | 16b | 3'UTR G>C | 2823 +684 G>C | | 14161759 | C | C | C | C | C | C | C | T | T | T | C | T | C |
| XPC | NM_004628 | 16b | 3'UTR A>G | | | 14161824 | T | A | A | T | T | T | T | A | A | A | A | A | A |
| XPC | NM_004628 | 16b | 3'UTR T>A | | | 14161831 | C | T | T | C | C | C | C | T | T | T | T | T | T |
| XPC | NM_004628 | 16a | 3'UTR C>G | | | 14162346 | C | C | C | C | C | C | C | C | C | C | C | C | C |
| XPC | NM_004628 | 16a | 2815 C>A | | Q>K | 14162450 | A | A | A | A | A | A | A | A | A | A | A | A | A |
| XPC | NM_004628 | 16a | IVS15 -40 A>G | 2605 -40 A>G | | 14162700 | A | A | A | A | A | A | A | A | A | A | A | A | A |
| XPC | NM_004628 | 16a | IVS15 -51 A>G | 2605 -51 A>G | | 14162711 | G | G | G | G | G | G | G | G | G | G | G | G | G |
| XPC | NM_004628 | 15 | IVS15 +90 G>T | 2604 +90 G>T | | 14163701 | C | C | C | C | C | C | C | C | C | C | C | C | C |
| XPC | NM_004628 | 15 | IVS15 +28 C>G | 2604 +28 C>G | | 14163763 | T | T | T | T | T | T | T | T | T | T | T | T | T |
| XPC | NM_004628 | 14 | IVS14 +68 T>C | 2514 +68 T>C | | 14164341 | A | A | A | A | A | A | A | A | A | A | A | A | A |
| XPC | NM_004628 | 12&13 | IVS 12 -6 A>C | 2251 -6 A>C | | 14165238 | C | C | C | C | C | C | C | C | C | C | C | C | C |
| XPC | NM_004628 | 12&13 | IVS 12 +46 C>G | 2250 +46 C>G | R>R | 14165269 | G | G | G | G | G | G | G | G | G | G | G | G | G |
| XPC | NM_004628 | 11 | 2061 G>A | | | 14168890 | A | A | A | A | A | A | A | A | A | A | A | A | A |
| XPC | NM_004628 | 10 | del C | | A>A | 14172877 | del | del | del | del | del | del | del | del | del | del | del | del | del |
| XPC | NM_004628 | 10 | 1881 T>A | | A>V | 14172989 | A | A | A | A | A | A | A | A | A | A | A | A | A |
| XPC | NM_004628 | 9b | 1496 C>T | | D>A | 14174889 | T | T | T | C | C | T | C | C | C | C | C | C | T |
| XPC | NM_004628 | 9a | 1415 A>C | | | 14174970 | C | C | C | C | C | C | C | C | C | C | C | C | C |
| XPC | NM_004628 | 9a | del G | | | 14174971 | del | del | del | del | del | del | del | del | del | del | del | del | del |
| XPC | NM_004628 | 9a | del G | | | 14175043 | del | del | del | del | del | del | del | del | del | del | del | del | del |
| XPC | NM_004628 | 8 | IVS7 -70 A>C | 901 -70 A>C | | 14176404 | A | A | A | A | A | A | A | A | A | A | A | A | A |
| XPC | NM_004628 | 5 | IVS5 +44 C>G | 821 +44 C>G | | 14183629 | C | C | C | C | C | C | C | C | C | C | C | C | C |
| XPC | NM_004628 | 3 | IVS3 +73 G>T | 412 +73 G>T | | 14186869 | G | G | T | G | T | G | T | nd | G | G | G | G | T |

| Gene | Accession | Exon | Variant | Variant (alt) | AA | Position | S1 | S2 | S3 | S4 | S5 | S6 | S7 | S8 | S9 | S10 | S11 | S12 | S13 |
|---|---|---|---|---|---|---|---|---|---|---|---|---|---|---|---|---|---|---|---|
| GRIP2 | NM_001080423 | 13 | IVS13 +42 ins AACT | 1787 -42 ins AACT | | 14530762 | wt | wt | ins | wt | wt | wt | ins | nd | nd | wt | wt | wt | wt |
| GRIP2 | NM_001080423 | 13 | 1776 T>C | | S>S | 14530815 | T | T | C | T | T | T | A | nd | nd | T | T | T | T |
| GRIP2 | NM_001080423 | 13 | IVS12 -35 G>A | 1601 -35 G>A | | 14531025 | G | G | A | G | G | G | ins | nd | nd | nd | ins | G | G |
| GRIP2 | NM_001080423 | 10 | 1309 ins | | | 14536633 | C | ins | ins | ins | ins | C | T | nd | nd | nd | T | T | C |
| GRIP2 | NM_001080423 | 8 | 894 T>C | | | 14538262 | nd | T | T | T | T | T | nd | nd | nd | nd | nd | nd | C |
| Marker | D3S3595 | | | | | 14617642 | 265 | | | | | | 265 | | | | | | |
| C3orf19 | NM_016474 | | Start 14617332 | | End | 14617642 | nd | nd | nd | nd | nd | nd | nd | nd | nd | nd | nd | nd | nd |
| C3orf19 | NM_016474 | 2 | IVS2+122 T>A | 147+122 T>A | | 14671163 | A | C | C | C | A | C | C | C | C | A | C | C | A |
| C3orf19 | NM_016474 | 3 | IVS3+45 C>A | 248+45 C>A | | 14672185 | C | C | A | C | C | C | G | G | G | C | G | G | G |
| C3orf19 | NM_016474 | 3 | IVS3+182 A>G | 248+182 A>G | | 14672322 | A | A | A | A | A | A | A | A | A | A | A | A | A |
| C3orf19 | NM_016474 | 5 | IVS4-55 C>A | 308-55 C>A | | 14677986 | C | C | C | C | C | C | C | C | C | C | C | C | C |
| C3orf19 | NM_016474 | 5 | IVS5+83 C>G & T | 485+83 C>G & T | | 14678301 | C | C | C | C | C | T | C | T | T | C | C | C | C |
| C3orf19 | NM_016474 | 5 | IVS5+190 delTTACAATA | 485+190 delTTACAATA | | 14678409 | del | del | del | del | del | del | del | del | del | del | del | del | del |
| C3orf19 | NM_016474 | 6 | IVS6+139 insTTGA | 581+139 insGATT | | 14681773 | wt | wt | wt | wt | wt | wt | ins | wt | wt | ins | wt | wt | A |
| C3orf19 | NM_016474 | 6 | IVS6+140 A>G | 581+140 A>G | | 14681774 | ins | wt | ins | wt | wt | ins | ins | ins | ins | ins | wt | wt | G |
| C3orf19 | NM_016474 | 6 | IVS6+141 insTTGG | 581+141 insTTGG | | 14681775 | G | G | G | G | G | G | G | G | G | G | G | G | G |
| C3orf19 | NM_016474 | 8 | IVS7 -13 A>G | 724 -13 A>G | | 14683922 | A | G | A | A | G | C | G | G | G | G | G | G | C |
| C3orf19 | NM_016474 | 8 | IVS8 +33 G>C | 819 +33 G>C | | 14684062 | C | A | C | C | A | A | A | A | A | A | A | A | A |
| C3orf19 | NM_016474 | 11C | 3UTR G>A | 1404-825 G>A | | 14688530 | A | C | A | A | C | C | C | C | C | C | C | C | C |
| C3orf20 | NM_032137 | 2 | 5UTR C>T | 405-505 C>T | | 14698720 | G | G | G | G | G | G | G | G | G | G | G | G | G |
| C3orf20 | NM_032137 | 2 | 5UTR A>G | 405-498 A>G | | 14698728 | G | G | G | G | G | G | G | G | G | G | G | G | G |
| C3orf20 | NM_032137 | 2 | 5UTR C>A | 405-471 C>A | | 14698754 | A | A | A | A | A | A | A | A | A | A | A | A | A |
| C3orf20 | NM_032137 | 3 | 125 G>A | 125 G>A | G>D | 14699349 | A | A | A | A | A | A | A | A | A | A | A | A | A |
| C3orf20 | NM_032137 | 3 | 193 G>A | 193 G>A | D>N | 14699417 | G | G | G | G | G | G | G | G | G | G | G | G | G |
| C3orf20 | NM_032137 | 7 | 892 G>A | 892 G>A | A>T | 14720861 | G | G | G | G | G | G | G | G | G | G | G | G | G |
| C3orf20 | NM_032137 | 8 | 1219 G>A | 1219 G>A | I>V | 14730576 | A | A | A | A | A | A | A | A | A | A | A | A | A |
| C3orf20 | NM_032137 | 8 | 1264 G>C | 1264 G>C | L>V | 14730621 | A | A | A | A | A | A | A | A | A | A | A | A | A |
| C3orf20 | NM_032137 | Ex9 | IVS8 -66 A>G | 1314-66 A>G | | 14731734 | G | G | G | G | G | G | G | G | G | G | G | G | G |
| C3orf20 | NM_032137 | 11 | IVS11 +3 A>G | 1690+3A>G | | 14743538 | A | A | A | A | A | A | A | A | A | A | A | A | A |
| C3orf20 | NM_032137 | 11 | IVS11 +23 G>A | 1690+23G>A | | 14743558 | A | A | A | A | A | A | A | A | A | A | A | A | A |
| C3orf20 | NM_032137 | 13 | 2039 G>A | 2039 G>A | R>H | 14773980 | A | G | A | G | A | A | A | A | A | A | A | A | A |
| C3orf20 | NM_032137 | 14 | 2334 G>A | 2334 G>A | V>V | 14776491 | T | A | A | T | A | A | A | A | A | A | A | A | T |
| C3orf20 | NM_032137 | 14 | IVS14 +45 G>A | 2352+45 G>A | | 14778554 | C | C | C | C | C | C | C | C | C | C | C | C | C |
| C3orf20 | NM_032137 | 16 | IVS16 +117 G>C | 2630+117G>C | | 14788839 | T | T | T | T | T | T | T | T | T | T | T | T | T |
| FGD5 | NM_152536 | 10 | 934 G>A | 934 G>A | V>M | 14897239 | C | C | C | C | C | C | C | C | C | C | C | C | C |
| FGD5 | NM_152536 | 566 | IVS5 -22 C>A | 2160+22 G>A | | 14914303 | G | T | G | G | T | T | T | T | T | T | T | T | T |
| FGD5 | NM_152536 | 566 | IVS5 -62 G>A | 2187 -82 G>A | | 14914356 | G | T | G | G | T | T | T | T | T | T | T | T | T |
| FGD5 | NM_152536 | 566 | 2230 G>T | 2230 G>T | L>L | 14914493 | G | G | G | G | G | G | G | G | G | G | G | G | G |
| FGD5 | NM_152536 | 8 | IVS8 +64 T>C | 2482+64 T>C | | 14917028 | G | G | G | G | G | G | G | G | G | G | G | G | G |
| FGD5 | NM_152536 | 10 | IVS10 +50 C>T | 2613+50 C>T | | 14929239 | A | A | A | A | A | A | A | A | A | A | A | A | A |
| FGD5 | NM_152536 | 15 | 3072 C>T | 3072 C>T | H>H | 14939047 | T | T | T | T | T | T | T | T | T | T | T | T | T |
| FGD5 | NM_152536 | 15 | IVS15 -74 G>A | 3215-74 G>A | | 14939483 | C | C | C | C | C | C | C | C | C | C | C | C | C |
| FGD5 | NM_152536 | 17 | IVS16 -49 C>T | 3215-49 C>T | | 14940470 | G | G | G | G | G | G | G | G | G | G | G | G | G |
| FGD5 | NM_152536 | 17 | IVS16 -8 A>G | 3215-8 A>G | | 14940511 | T | T | T | T | T | T | T | T | T | T | T | T | T |
| NR2C2 | NM_003298 | 8 | IVS7 -70 G>A | 857+70 G>A | | 15040789 | G | G | G | G | G | G | A | G | G | G | G | G | G |

| Markers | 3p25 location | Affected haplotype | Unaffected recombinants | |
|---|---|---|---|---|
| | | | AR14 | AR6 |
| D3S2403 | 13147397 - 13147709 | 251 | 251 | 251 |
| D3S1516 | 13628628 - 13629103 | 347 | 359 | 347 |
| D3S3608 | 13670236 - 13679541 | 165 | 175 | 165 |
| D3S2385 | 13853945 - 13854287 | 146 | 142 | 146 |
| D3S3602 | 13900968 - 13901215 | 113 | 123 | 113 |
| D3S1585 | 13916682 - 13916861 | 118 | 126 | 118 |
| TMEM43 | 14158166 C>T | T | C | C |
| D3S1554 | 14342778 - 14343106 | 129 | 129 | 133 |
| D3S3595 | 14617332 - 14617642 | 265 | 265 | 265 |
| D3S3613 | 15271250 - 15357905 | 193 | 193 | 187 |

Figure 11

SEQUENCE LISTING

```
<160> NUMBER OF SEQ ID NOS: 76

<210> SEQ ID NO 1
<211> LENGTH: 550
<212> TYPE: DNA
<213> ORGANISM: Homo sapiens

<400> SEQUENCE: 1
agcaacatgg gcccatcctc atctagggac aggagagatc tgctgagctg gtgaggtgta      60
gagcaggtgg cacctcatca cctttctcct ttccacagtg gactggtttc ctgttttccg     120
agacctggtc aacattggcc tgaaagcctt tgccttctgt gtggccacct cgctgaccct     180
gctgaccgtg gcggctggct ggctcttcta ccgacccctg tgggccctcc tcattgccgg     240
cctggccctt gtgcccatcc ttgttgctcg gacacgggtg ccagccaaaa agttggagtg     300
aaaagaccct ggcacccgcc cgacacctgc gtgagcccta ggatccaggt cctctctcac     360
ctctgaccca gctccatgcc agagcaggag ccccggtcaa ttttggactc tgcactccct     420
ctcctcttca ggggccagac ttggcagcat gtgcaccagg ttggtgttca ccagctcatg     480
tcttccccac atctcttctt gccagtaagc agctttggtg ggcagcagca gctcatgaat     540
ggcaagctga                                                             550

<210> SEQ ID NO 2
<211> LENGTH: 3254
<212> TYPE: DNA
<213> ORGANISM: Homo sapiens

<400> SEQUENCE: 2
ggtaactgca gtaagtcccg cttggccctg gagtccacgc ggattttcga agctggggct      60
ggcaagaggc cgctggacac cacgctccag tcgtcagccc acttcctagc tgaacagcgc     120
gaggcggcgc cagcgagccg ggtcccacca tggccgcgaa ttattccagt accagtaccc     180
ggagagaaca tgtcaaagtt aaaaccagct cccagccagg cttcctggaa cggctgagcg     240
agacctcggg tgggatgttt gtggggctca tggccttcct gctctccttc tacctaattt     300
tcaccaatga gggccgcgca ttgaagacgg caacctcatt ggctgagggg ctctcgcttg     360
tggtgtctcc cgacagcatc cacagtgtgg ctccggagaa tgaaggaagg ctggtgcaca     420
tcattggcgc cttacggaca tccaagcttt tgtctgatcc aaactatggg gtccatcttc     480
cggctgtgaa actgcggagg cacgtggaga tgtaccaatg ggtagaaact gaggagtcca     540
gggagtacac cgaggatggg caggtgaaga aggagacgag gtattcctac aacactgaat     600
ggaggtcaga aatcatcaac agcaaaaact cgaccgaga gattggccac aaaaacccca     660
gtgccatggc agtggagtca ttcatggcaa cagcccctt tgtccaaatt ggcaggtttt     720
tcctctcgtc aggcctcatc gacaaagtcg acaacttcaa gtccctgagc ctatccaagc     780
tggaggaccc tcatgtggac atcattcgcc gtggagactt tttctaccac agcgaaaatc     840
ccaagtatcc agaggtggga gacttgcgtg tctccttttc ctatgctgga ctgagcggcg     900
```

```
atgaccctga cctgggccca gctcacgtgg tcactgtgat tgcccggcag cggggtgacc    960
agctagtccc attctccacc aagtctgggg ataccttact gctcctgcac cacgggact    1020
tctcagcaga ggaggtgttt catagagaac taaggagcaa ctccatgaag acctggggcc    1080
tgcgggcagc tggctggatg gccatgttca tgggcctcaa ccttatgaca cggatcctct    1140
acaccttggt ggactggttt cctgtttttcc gagacctggt caacattggc ctgaaagcct    1200
ttgccttctg tgtggccacc tcgctgaccc tgctgaccgt ggcggctggc tggctcttct    1260
accgaccccT gtgggccctc ctcattgccg gcctggccct tgtgcccatc cttgttgctc    1320
ggacacgggc gccagccaaa aagttggagt gaaaagaccc tggcacccgc ccgacacctg    1380
cgtgagccct aggatccagg tcctctctca cctctgaccc agctccatgc cagagcagga    1440
gccccggtca atttTggact ctgcactccc tctcctcttc aggggccaga cttggcagca    1500
tgtgcaccag gttggtgttc accagctcat gtcttcccca catctcttct tgccagtaag    1560
cagctttggt gggcagcagc agctcatgaa tggcaagctg acagcttctc ctgctgtttc    1620
cttcctctct tggactgagt gggtacgccc agccactcag cccattggca gctgacaacg    1680
cagacacgct ctacggaggc ctgctgataa agggctcagc cttgccgtgt gctgcttctc    1740
atcactgcac acaagtgcca tgcttTgcca ccaccaccaa gcacatctgt gatcctgaag    1800
ggcggccgtt agtcattact gctgagtcct gggtcaccag cagacacact gggcatggac    1860
ccctcaaagc aggcacaccc aaaacacaag tctgtggcta aacctgatg tggtgtttaa    1920
aagagaagaa acactgaaga tgtcctgagg agaaaagctg acatatact gggcttcaca    1980
cttatcttat ggcttggcag aatctttgta gtgtgtggga tctctgaagg ccctatttaa    2040
gtttttcttc gttactttgc tgcttcatgt gtactttcct accccaagag gaagttttct    2100
gaaataagat ttaaaaacaa aacaaaaaaa acacttaata ttTcagactg ttacaggaaa    2160
cacccttTag tctgtcagtt gaattcagag cactgaaagg tgttaaattg gggtatgtgg    2220
tttgattgat aaaaagttac ctctcagtat tttgtgtcac tgagaagctt acaatggat    2280
gcttttgaaa caagtatcag caaaaggatt tgttttcact ctgggaggag agggtggaga    2340
aagcacttgc tttcatcctc tggcatcgga aactccccta tgcacttgaa gatggtttaa    2400
aagattaaag aaacgattaa gagaaaaggt tggaagcttt atactaaatg ggctccttca    2460
tggtgacgcc ccgtcaacca caatcaagaa ctgaggcctg aggctggttg tacaatgccc    2520
acgcctgcct ggctgctttc acctgggagt gctttcgatg tgggcacctg gcttcctag    2580
ggctgcttct gagtggttct ttcacgtgtt gtgtccatag ctttagtctt cctaaataag    2640
atccacccac acctaagtca cagaatttct aagttcccca actactctca cacccttTta    2700
aagataaagt atgttgtaac caggatgtct taaatgattc tttgtgtacc ttttctgtca    2760
tattcagaaa ccgttttgtg cctgctggga gtaattcctt tagcaattaa gtatttggta    2820
gctgaataag gggtcagaac ttctgaaacc agagatctgt aatcatctct attggcctgg    2880
ggtgcctgtg ctataaatga gtttcttcac atgaaaaaca cagccagccc aagatgactt    2940
atctgggttt aggattcaat agtattcact aactgcttat tacatgagca atttcatcaa    3000
atctccaaac tcttaaagga tgctttcgga aaacacgctg tatacctaga tgatgactaa    3060
atgcaaaatc cttgggcttt ggttttTttc tagtaaggat tttaaataac tgccgacttc    3120
aaaagtgttc ttaaaacgaa agataatgtt aagaaaatt tgaaagcttt ggaaaaccaa    3180
atttgtaata tcattgtatt tTttattaaa agttttgtaa taaatttcta aattataaaa    3240
aaaaaaaaaa aaaa                                                      3254
```

<210> SEQ ID NO 3
<211> LENGTH: 400
<212> TYPE: PRT
<213> ORGANISM: Homo sapiens

<400> SEQUENCE: 3

Met Ala Ala Asn Tyr Ser Ser Thr Ser Thr Arg Arg Glu His Val Lys
1               5                   10                  15

Val Lys Thr Ser Ser Gln Pro Gly Phe Leu Glu Arg Leu Ser Glu Thr
            20                  25                  30

Ser Gly Gly Met Phe Val Gly Leu Met Ala Phe Leu Leu Ser Phe Tyr
        35                  40                  45

Leu Ile Phe Thr Asn Glu Gly Arg Ala Leu Lys Thr Ala Thr Ser Leu
50                  55                  60

Ala Glu Gly Leu Ser Leu Val Val Ser Pro Asp Ser Ile His Ser Val
65                  70                  75                  80

Ala Pro Glu Asn Glu Gly Arg Leu Val His Ile Ile Gly Ala Leu Arg
                85                  90                  95

Thr Ser Lys Leu Leu Ser Asp Pro Asn Tyr Gly Val His Leu Pro Ala
            100                 105                 110

Val Lys Leu Arg Arg His Val Glu Met Tyr Gln Trp Val Glu Thr Glu
        115                 120                 125

Glu Ser Arg Glu Tyr Thr Glu Asp Gly Gln Val Lys Lys Glu Thr Arg
    130                 135                 140

Tyr Ser Tyr Asn Thr Glu Trp Arg Ser Glu Ile Ile Asn Ser Lys Asn
145                 150                 155                 160

Phe Asp Arg Glu Ile Gly His Lys Asn Pro Ser Ala Met Ala Val Glu
                165                 170                 175

Ser Phe Met Ala Thr Ala Pro Phe Val Gln Ile Gly Arg Phe Phe Leu
            180                 185                 190

Ser Ser Gly Leu Ile Asp Lys Val Asp Asn Phe Lys Ser Leu Ser Leu
        195                 200                 205

Ser Lys Leu Glu Asp Pro His Val Asp Ile Ile Arg Arg Gly Asp Phe
    210                 215                 220

Phe Tyr His Ser Glu Asn Pro Lys Tyr Pro Glu Val Gly Asp Leu Arg
225                 230                 235                 240

Val Ser Phe Ser Tyr Ala Gly Leu Ser Gly Asp Asp Pro Asp Leu Gly
                245                 250                 255

Pro Ala His Val Val Thr Val Ile Ala Arg Gln Arg Gly Asp Gln Leu
            260                 265                 270

Val Pro Phe Ser Thr Lys Ser Gly Asp Thr Leu Leu Leu Leu His His
        275                 280                 285

Gly Asp Phe Ser Ala Glu Glu Val Phe His Arg Glu Leu Arg Ser Asn
    290                 295                 300

Ser Met Lys Thr Trp Gly Leu Arg Ala Ala Gly Trp Met Ala Met Phe
305                 310                 315                 320

Met Gly Leu Asn Leu Met Thr Arg Ile Leu Tyr Thr Leu Val Asp Trp
                325                 330                 335

Phe Pro Val Phe Arg Asp Leu Val Asn Ile Gly Leu Lys Ala Phe Ala
            340                 345                 350

Phe Cys Val Ala Thr Ser Leu Thr Leu Leu Thr Val Ala Ala Gly Trp
        355                 360                 365

Leu Phe Tyr Arg Pro Leu Trp Ala Leu Leu Ile Ala Gly Leu Ala Leu

```
                    370                 375                 380
Val Pro Ile Leu Val Ala Arg Thr Arg Val Pro Ala Lys Lys Leu Glu
385                 390                 395                 400

<210> SEQ ID NO 4
<211> LENGTH: 550
<212> TYPE: DNA
<213> ORGANISM: Homo sapiens

<400> SEQUENCE: 4
agcaacatgg gcccatcctc atctagggac aggagagatc tgctgagctg gtgaggtgta      60
gagcaggtgg cacctcatca cctttctcct ttccacagtg gactggtttc ctgttttccg     120
agacctggtc aacattggcc tgaaagcctt tgccttctgt gtggccacct tgctgaccct     180
gctgaccgtg gcggctggct ggctcttcta ccgaccctg tgggccctcc tcattgccgg      240
cctggccctt gtgcccatcc ttgttgctcg gacacgggtg ccagccaaaa agttggagtg     300
aaaagaccct ggcaccccgcc cgacacctgc gtgagcccta ggatccaggt cctctctcac    360
ctctgaccca gctccatgcc agagcaggag ccccggtcaa ttttggactc tgcactccct    420
ctcctcttca ggggccagac ttggcagcat gtgcaccagg ttggtgttca ccagctcatg    480
tcttccccac atctcttctt gccagtaagc agctttggtg ggcagcagca gctcatgaat    540
ggcaagctga                                                           550

<210> SEQ ID NO 5
<211> LENGTH: 3254
<212> TYPE: DNA
<213> ORGANISM: Homo sapiens

<400> SEQUENCE: 5
ggtaactgca gtaagtcccg cttggccctg gagtccacgc ggattttcga agctggggct      60
ggcaagaggc cgctggacac cacgctccag tcgtcagccc acttcctagc tgaacagcgc     120
gaggcggcgg cagcgagccg ggtcccacca tggccgcgaa ttattccagt accagtaccc     180
ggagagaaca tgtcaaagtt aaaaccagct cccagccagg cttcctgaa cggctgagcg      240 agacctcggg tgggatgttt gtggggctca tggccttcct gctctccttc tacctaattt     300
tcaccaatga gggccgcgca ttgaagacgg caacctcatt ggctgagggg ctctcgcttg     360
tggtgtctcc cgacagcatc cacagtgtgg ctccggagaa tgaaggaagg ctggtgcaca    420
tcattggcgc cttacggaca tccaagcttt tgtctgatcc aaactatggg gtccatcttc     480
cggctgtgaa actgcggagg cacgtggaga tgtaccaatg ggtagaaact gaggagtcca    540
gggagtacac cgaggatggg caggtgaaga aggagacgag gtattcctac aacactgaat    600
ggaggtcaga aatcatcaac agcaaaaact tcgaccgaga gattggccac aaaaacccca    660
gtgccatggc agtggagtca ttcatggcaa cagcccccctt tgtccaaatt ggcaggtttt    720
tcctctcgtc aggcctcatc gacaaagtcg acaacttcaa gtccctgagc ctatccaagc    780
tggaggaccc tcatgtggac atcattcgcc gtggagactt tttctaccac agcgaaaatc    840
ccaagtatcc agaggtggga gacttgcgtg tctccttttc ctatgctgga ctgagcggcg    900
atgaccctga cctgggccca gctcacgtgg tcactgtgat tgcccggcag cggggtgacc    960
agctagtccc attctccacc aagtctgggg ataccttact gctcctgcac cacggggact   1020
tctcagcaga ggaggtgttt catagagaac taaggagcaa ctccatgaag acctgggggcc   1080 tgcgggcagc tggctggatg gccatgttca tgggcctcaa ccttatgaca cggatcctct   1140
```

| | | | | |
|---|---|---|---|---|
| acaccttggt | ggactggttt | cctgttttcc | gagacctggt | caacattggc ctgaaagcct | 1200 |
| ttgccttctg | tgtggccacc | ttgctgaccc | tgctgaccgt | ggcggctggc tggctcttct | 1260 |
| accgacccct | gtgggccctc | ctcattgccg | gcctggccct | tgtgcccatc cttgttgctc | 1320 |
| ggacacgggg | gccagccaaa | aagttggagt | gaaaagaccc | tggcacccgc cgacacctg | 1380 |
| cgtgagccct | aggatccagg | tcctctctca | cctctgaccc | agctccatgc cagagcagga | 1440 |
| gccccggtca | attttggact | ctgcactccc | tctcctcttc | aggggccaga cttggcagca | 1500 |
| tgtgcaccag | gttggtgttc | accagctcat | gtcttcccca | catctcttct tgccagtaag | 1560 |
| cagctttggt | gggcagcagc | agctcatgaa | tggcaagctg | acagcttctc ctgctgtttc | 1620 |
| cttcctctct | tggactgagt | gggtacggcc | agccactcag | cccattggca gctgacaacg | 1680 |
| cagacacgct | ctacggaggc | ctgctgataa | agggctcagc | cttgccgtgt gctgcttctc | 1740 |
| atcactgcac | acaagtgcca | tgctttgcca | ccaccaccaa | gcacatctgt gatcctgaag | 1800 |
| ggcggccgtt | agtcattact | gctgagtcct | gggtcaccag | cagacacact gggcatggac | 1860 |
| ccctcaaagc | aggcacaccc | aaaacacaag | tctgtggcta | gaacctgatg tggtgtttaa | 1920 |
| aagagaagaa | acactgaaga | tgtcctgagg | agaaagctg | acatatact gggcttcaca | 1980 |
| cttatcttat | ggcttggcag | aatctttgta | gtgtgtggga | tctctgaagg ccctatttaa | 2040 |
| gttttcttc | gttactttgc | tgcttcatgt | gtactttcct | accccaagag gaagttttct | 2100 |
| gaaataagat | ttaaaaacaa | aacaaaaaaa | acacttaata | tttcagactg ttacaggaaa | 2160 |
| cacccttag | tctgtcagtt | gaattcagag | cactgaaagg | tgttaaattg gggtatgtgg | 2220 |
| tttgattgat | aaaaagttac | ctctcagtat | tttgtgtcac | tgagaagctt acaatggat | 2280 |
| gcttttgaaa | caagtatcag | caaaaggatt | tgttttcact | ctgggaggag agggtggaga | 2340 |
| aagcacttgc | tttcatcctc | tggcatcgga | aactccccta | tgcacttgaa gatggtttaa | 2400 |
| aagattaaag | aaacgattaa | gagaaaaggt | tggaagcttt | atactaaatg ggctccttca | 2460 |
| tggtgacgcc | ccgtcaacca | caatcaagaa | ctgaggcctg | aggctggttg tacaatgccc | 2520 |
| acgcctgcct | ggctgctttc | acctgggagt | gctttcgatg | tgggcacctg gcttcctag | 2580 |
| ggctgcttct | gagtggttct | ttcacgtgtt | gtgtccatag | ctttagtctt cctaaataag | 2640 |
| atccacccac | acctaagtca | cagaatttct | aagttcccca | actactctca cacccttta | 2700 |
| aagataaagt | atgttgtaac | caggatgtct | taaatgattc | tttgtgtacc ttttctgtca | 2760 |
| tattcagaaa | ccgttttgtg | cctgctggga | gtaattcctt | tagcaattaa gtatttggta | 2820 |
| gctgaataag | gggtcagaac | ttctgaaacc | agagatctgt | aatcatctct attggcctgg | 2880 |
| ggtgcctgtg | ctataaatga | gtttcttcac | atgaaaaaca | cagccagccc aagatgactt | 2940 |
| atctgggttt | aggattcaat | agtattcact | aactgcttat | tacatgagca atttcatcaa | 3000 |
| atctccaaac | tcttaaagga | tgctttcgga | aaacacgctg | tatacctaga tgatgactaa | 3060 |
| atgcaaaatc | cttgggcttt | ggtttttttc | tagtaaggat | tttaaataac tgccgacttc | 3120 |
| aaaagtgttc | ttaaaacgaa | agataatgtt | aagaaaaatt | tgaaagcttt ggaaaaccaa | 3180 |
| atttgtaata | tcattgtatt | ttttattaaa | agttttgtaa | taaatttcta aattataaaa | 3240 |
| aaaaaaaaaa | aaaa | | | | 3254 |

<210> SEQ ID NO 6
<211> LENGTH: 400
<212> TYPE: PRT
<213> ORGANISM: Homo sapiens

<400> SEQUENCE: 6

```
Met Ala Ala Asn Tyr Ser Ser Thr Ser Thr Arg Arg Glu His Val Lys
1               5                   10                  15

Val Lys Thr Ser Ser Gln Pro Gly Phe Leu Glu Arg Leu Ser Glu Thr
            20                  25                  30

Ser Gly Gly Met Phe Val Gly Leu Met Ala Phe Leu Leu Ser Phe Tyr
        35                  40                  45

Leu Ile Phe Thr Asn Glu Gly Arg Ala Leu Lys Thr Ala Thr Ser Leu
    50                  55                  60

Ala Glu Gly Leu Ser Leu Val Val Ser Pro Asp Ser Ile His Ser Val
65              70                  75                  80

Ala Pro Glu Asn Glu Gly Arg Leu Val His Ile Ile Gly Ala Leu Arg
                85                  90                  95

Thr Ser Lys Leu Leu Ser Asp Pro Asn Tyr Gly Val His Leu Pro Ala
                100                 105                 110

Val Lys Leu Arg Arg His Val Glu Met Tyr Gln Trp Val Glu Thr Glu
            115                 120                 125

Glu Ser Arg Glu Tyr Thr Glu Asp Gly Gln Val Lys Lys Glu Thr Arg
    130                 135                 140

Tyr Ser Tyr Asn Thr Glu Trp Arg Ser Glu Ile Ile Asn Ser Lys Asn
145                 150                 155                 160

Phe Asp Arg Glu Ile Gly His Lys Asn Pro Ser Ala Met Ala Val Glu
                165                 170                 175

Ser Phe Met Ala Thr Ala Pro Phe Val Gln Ile Gly Arg Phe Phe Leu
                180                 185                 190

Ser Ser Gly Leu Ile Asp Lys Val Asp Asn Phe Lys Ser Leu Ser Leu
            195                 200                 205

Ser Lys Leu Glu Asp Pro His Val Asp Ile Ile Arg Arg Gly Asp Phe
    210                 215                 220

Phe Tyr His Ser Glu Asn Pro Lys Tyr Pro Glu Val Gly Asp Leu Arg
225                 230                 235                 240

Val Ser Phe Ser Tyr Ala Gly Leu Ser Gly Asp Pro Asp Leu Gly
                245                 250                 255

Pro Ala His Val Val Thr Val Ile Ala Arg Gln Arg Gly Asp Gln Leu
        260                 265                 270

Val Pro Phe Ser Thr Lys Ser Gly Asp Thr Leu Leu Leu His His
        275                 280                 285

Gly Asp Phe Ser Ala Glu Glu Val Phe His Arg Glu Leu Arg Ser Asn
    290                 295                 300

Ser Met Lys Thr Trp Gly Leu Arg Ala Ala Gly Trp Met Ala Met Phe
305                 310                 315                 320

Met Gly Leu Asn Leu Met Thr Arg Ile Leu Tyr Thr Leu Val Asp Trp
                325                 330                 335

Phe Pro Val Phe Arg Asp Leu Val Asn Ile Gly Leu Lys Ala Phe Ala
                340                 345                 350

Phe Cys Val Ala Thr Leu Leu Thr Leu Leu Thr Val Ala Ala Gly Trp
            355                 360                 365

Leu Phe Tyr Arg Pro Leu Trp Ala Leu Leu Ile Ala Gly Leu Ala Leu
    370                 375                 380

Val Pro Ile Leu Val Ala Arg Thr Arg Val Pro Ala Lys Lys Leu Glu
385                 390                 395                 400

<210> SEQ ID NO 7
<211> LENGTH: 400
```

<212> TYPE: PRT
<213> ORGANISM: Pan troglodytes

<400> SEQUENCE: 7

```
Met Ala Ala Asn Tyr Ser Ser Thr Ser Thr Arg Arg Glu His Val Lys
1               5                   10                  15

Val Lys Thr Ser Ser Gln Pro Gly Phe Leu Glu Arg Leu Ser Glu Thr
            20                  25                  30

Ser Gly Gly Met Phe Val Gly Leu Met Ala Phe Leu Leu Ser Phe Tyr
        35                  40                  45

Leu Ile Phe Thr Asn Glu Gly Arg Ala Leu Lys Thr Ala Thr Ser Leu
    50                  55                  60

Ala Glu Gly Leu Ser Leu Val Val Ser Pro Asp Ser Ile His Ser Val
65                  70                  75                  80

Ala Pro Glu Asn Glu Gly Arg Leu Val His Ile Ile Gly Ala Leu Arg
                85                  90                  95

Thr Ser Lys Leu Leu Ser Asp Pro Asn Tyr Gly Val His Leu Pro Ala
            100                 105                 110

Val Lys Leu Arg Arg His Val Glu Met Tyr Gln Trp Val Glu Thr Glu
        115                 120                 125

Glu Ser Arg Glu Tyr Thr Glu Asp Gly Gln Val Lys Lys Glu Thr Arg
    130                 135                 140

Tyr Ser Tyr Asn Thr Glu Trp Arg Ser Glu Ile Ile Asn Ser Lys Asn
145                 150                 155                 160

Phe Asp Arg Glu Ile Gly His Lys Asn Pro Ser Ala Met Ala Val Glu
                165                 170                 175

Ser Phe Thr Ala Thr Ala Pro Phe Val Gln Ile Gly Arg Phe Phe Leu
            180                 185                 190

Ser Ser Gly Leu Ile Asp Lys Val Asp Asn Phe Lys Ser Leu Ser Leu
        195                 200                 205

Ser Lys Leu Glu Asp Pro His Val Asp Ile Ile Arg Arg Gly Asp Phe
    210                 215                 220

Phe Tyr His Ser Glu Asn Pro Lys Tyr Pro Glu Val Gly Asp Leu Arg
225                 230                 235                 240

Val Ser Phe Ser Tyr Ala Gly Leu Ser Gly Asp Pro Asp Leu Gly
                245                 250                 255

Pro Ala His Val Val Thr Val Ile Ala Gln Gln Arg Gly Asp Gln Leu
            260                 265                 270

Val Pro Phe Ser Thr Lys Ser Gly Asp Thr Leu Leu Leu His His
        275                 280                 285

Gly Asp Phe Ser Ala Glu Glu Val Phe His Arg Glu Leu Arg Ser Asn
    290                 295                 300

Ser Met Lys Thr Trp Gly Leu Arg Ala Ala Gly Trp Met Ala Met Phe
305                 310                 315                 320

Met Gly Leu Asn Leu Met Thr Arg Ile Leu Tyr Thr Leu Val Asp Trp
                325                 330                 335

Phe Pro Val Phe Arg Asp Leu Val Asn Ile Gly Leu Lys Ala Phe Ala
            340                 345                 350

Phe Cys Val Ala Thr Ser Leu Thr Leu Leu Thr Val Ala Ala Gly Trp
        355                 360                 365

Leu Phe Tyr Arg Pro Leu Trp Ala Leu Leu Ile Ala Ser Leu Ala Leu
    370                 375                 380

Val Pro Ile Leu Val Ala Arg Thr Arg Val Pro Ala Lys Lys Leu Glu
385                 390                 395                 400
```

<210> SEQ ID NO 8
<211> LENGTH: 400
<212> TYPE: PRT
<213> ORGANISM: Canis familiaris

<400> SEQUENCE: 8

| Met | Ala | Ala | Asn | Tyr | Ser | Ser | Thr | Ser | Asn | Arg | Arg | Glu | His | Val | Lys |
|---|---|---|---|---|---|---|---|---|---|---|---|---|---|---|---|
| 1 | | | | 5 | | | | | 10 | | | | | 15 | |

| Thr | Thr | Thr | Lys | Pro | Gln | Pro | Gly | Phe | Leu | Glu | Arg | Leu | Ser | Glu | Thr |
|---|---|---|---|---|---|---|---|---|---|---|---|---|---|---|---|
| | | | 20 | | | | | 25 | | | | | 30 | | |

| Ser | Gly | Gly | Met | Phe | Val | Gly | Leu | Met | Thr | Phe | Leu | Leu | Ser | Phe | Tyr |
|---|---|---|---|---|---|---|---|---|---|---|---|---|---|---|---|
| | | | 35 | | | | | 40 | | | | | 45 | | |

| Leu | Ile | Phe | Thr | Asn | Glu | Gly | Arg | Ala | Leu | Lys | Thr | Ala | Thr | Ser | Leu |
|---|---|---|---|---|---|---|---|---|---|---|---|---|---|---|---|
| | | | 50 | | | | | 55 | | | | | 60 | | |

| Ala | Glu | Gly | Leu | Ser | Leu | Val | Val | Ser | Pro | Asp | Ser | Ile | His | Ser | Val |
|---|---|---|---|---|---|---|---|---|---|---|---|---|---|---|---|
| 65 | | | | | 70 | | | | | 75 | | | | | 80 |

| Ala | Pro | Glu | Asn | Glu | Gly | Arg | Leu | Val | His | Ile | Ile | Gly | Ala | Leu | Arg |
|---|---|---|---|---|---|---|---|---|---|---|---|---|---|---|---|
| | | | | 85 | | | | | 90 | | | | | 95 | |

| Thr | Ser | Lys | Leu | Leu | Ser | Asp | Pro | Asn | Tyr | Gly | Val | His | Leu | Pro | Ala |
|---|---|---|---|---|---|---|---|---|---|---|---|---|---|---|---|
| | | | | 100 | | | | | 105 | | | | | 110 | |

| Val | Lys | Leu | Arg | Arg | His | Val | Glu | Met | Tyr | Gln | Trp | Val | Glu | Thr | Glu |
|---|---|---|---|---|---|---|---|---|---|---|---|---|---|---|---|
| | | | 115 | | | | | 120 | | | | | 125 | | |

| Glu | Ser | Arg | Glu | Tyr | Thr | Glu | Asp | Gly | Gln | Val | Lys | Thr | Glu | Thr | Arg |
|---|---|---|---|---|---|---|---|---|---|---|---|---|---|---|---|
| | | | 130 | | | | | 135 | | | | | 140 | | |

| Tyr | Ser | Tyr | Asn | Thr | Glu | Trp | Arg | Ser | Glu | Ile | Val | Asn | Ser | Arg | Asn |
|---|---|---|---|---|---|---|---|---|---|---|---|---|---|---|---|
| 145 | | | | | 150 | | | | | 155 | | | | | 160 |

| Phe | Asp | Arg | Glu | Ile | Gly | His | Lys | Asn | Pro | Ser | Ala | Met | Ala | Val | Glu |
|---|---|---|---|---|---|---|---|---|---|---|---|---|---|---|---|
| | | | | 165 | | | | | 170 | | | | | 175 | |

| Ser | Phe | Thr | Ala | Thr | Ala | Pro | Phe | Val | Gln | Ile | Gly | Arg | Phe | Phe | Leu |
|---|---|---|---|---|---|---|---|---|---|---|---|---|---|---|---|
| | | | | 180 | | | | | 185 | | | | | 190 | |

| Ser | Ala | Gly | Leu | Ile | Asp | Lys | Val | Asp | Asn | Phe | Lys | Pro | Leu | Ser | Leu |
|---|---|---|---|---|---|---|---|---|---|---|---|---|---|---|---|
| | | | 195 | | | | | 200 | | | | | 205 | | |

| Ala | Lys | Leu | Asp | Asp | Pro | His | Val | Asp | Ile | Ile | Arg | Arg | Gly | Asp | Tyr |
|---|---|---|---|---|---|---|---|---|---|---|---|---|---|---|---|
| | | 210 | | | | | 215 | | | | | 220 | | | |

| Phe | Tyr | His | Ser | Glu | Asn | Pro | Lys | Tyr | Pro | Glu | Val | Gly | Asp | Val | Arg |
|---|---|---|---|---|---|---|---|---|---|---|---|---|---|---|---|
| 225 | | | | | 230 | | | | | 235 | | | | | 240 |

| Val | Ser | Phe | Ser | Tyr | Ala | Gly | Leu | Ser | Gly | Asp | Pro | Asp | Leu | Gly |
|---|---|---|---|---|---|---|---|---|---|---|---|---|---|---|
| | | | | 245 | | | | | 250 | | | | | 255 |

Pro Ala His Val Val Thr Val Ile Ala Arg Gln Arg Gly Asp Gln Leu
          260                 265                 270

Val Pro Tyr Ser Thr Lys Ser Gly Asp Thr Leu Leu Leu Leu His His
        275                 280                 285

Gly Asp Phe Ser Ala Glu Glu Val Phe His Arg Glu Arg Lys Ser Asn
        290                 295                 300

Ser Leu Lys Thr Trp Gly Leu Arg Ala Ala Gly Trp Leu Ala Met Phe
305                 310                 315                 320

Met Gly Leu Asn Leu Met Thr Arg Ile Val Tyr Thr Leu Val Asp Trp
                325                 330                 335

Phe Pro Ile Phe Arg Asp Leu Val Asp Ile Gly Leu Lys Ala Phe Ala
            340                 345                 350

Phe Cys Val Ala Thr Ser Leu Thr Leu Leu Thr Val Ala Ala Gly Trp
        355                 360                 365

Leu Phe Tyr Arg Pro Leu Cys Ala Leu Phe Ile Ser Cys Leu Ala Leu

```
                370                 375                 380
Val Pro Ile Ile Ile Ala Arg Thr Arg Val Pro Ala Lys Lys Leu Glu
385                 390                 395                 400

<210> SEQ ID NO 9
<211> LENGTH: 400
<212> TYPE: PRT
<213> ORGANISM: Mus musculus

<400> SEQUENCE: 9

Met Ala Ala Asn Tyr Ser Ser Thr Ser Ser Arg Lys Glu His Val Lys
1               5                   10                  15

Val Thr Ser Glu Pro Gln Pro Gly Phe Leu Glu Arg Leu Ser Glu Thr
            20                  25                  30

Ser Gly Gly Met Phe Val Gly Leu Met Thr Phe Leu Leu Ser Phe Tyr
        35                  40                  45

Leu Ile Phe Thr Asn Glu Gly Arg Ala Leu Lys Thr Ala Thr Ser Leu
    50                  55                  60

Ala Glu Gly Leu Ser Leu Val Val Ser Pro Asp Ser Ile His Ser Val
65                  70                  75                  80

Ala Pro Glu Asn Glu Gly Arg Leu Val His Ile Ile Gly Ala Leu Arg
                85                  90                  95

Thr Ser Lys Leu Leu Ser Asp Pro Asn Tyr Gly Val His Leu Pro Ala
            100                 105                 110

Val Lys Leu Arg Arg His Val Glu Met Tyr Gln Trp Val Glu Thr Glu
        115                 120                 125

Glu Ser Ser Glu Tyr Thr Glu Asp Gly Gln Val Lys Lys Glu Thr Lys
    130                 135                 140

Tyr Ser Tyr Asn Thr Glu Trp Arg Ser Glu Ile Val Asn Ser Arg Asn
145                 150                 155                 160

Phe Asp Arg Glu Ile Gly His Lys Asn Pro Ser Ala Met Ala Val Glu
                165                 170                 175

Ser Phe Thr Ala Thr Ala Pro Phe Val Gln Ile Gly Arg Phe Phe Leu
            180                 185                 190

Ser Ala Gly Leu Ile Asp Lys Ile Asp Asn Phe Lys Ala Leu Ser Leu
        195                 200                 205

Ala Lys Leu Glu Asp Pro His Val Asp Ile Ile Arg Arg Gly Asp Phe
    210                 215                 220

Phe Tyr His Ser Glu Asn Pro Lys Tyr Pro Glu Val Gly Asp Val Arg
225                 230                 235                 240

Val Ser Phe Ser Tyr Ala Gly Leu Ser Ser Asp Asp Pro Asp Leu Gly
                245                 250                 255

Pro Ala His Val Val Thr Val Ile Ala Arg Gln Arg Gly Asp Gln Leu
            260                 265                 270

Ile Pro Tyr Ser Thr Lys Ser Gly Asp Thr Leu Leu Leu His His
    275                 280                 285

Gly Asp Phe Ser Ala Glu Glu Val Phe Arg Arg Glu Gln Lys Ser Asn
290                 295                 300

Ser Met Lys Thr Trp Gly Leu Arg Ala Ala Gly Trp Met Ala Met Phe
305                 310                 315                 320

Met Gly Leu Asn Leu Met Thr Arg Ile Leu Tyr Thr Leu Val Asp Trp
                325                 330                 335

Phe Pro Val Phe Arg Asp Leu Val Asn Ile Gly Leu Lys Ala Phe Ala
            340                 345                 350
```

```
Phe Cys Val Ala Thr Ser Leu Thr Leu Leu Thr Val Ala Ala Gly Trp
            355                 360                 365

Leu Phe Tyr Arg Pro Leu Trp Ala Ala Leu Ile Gly Cys Leu Ala Leu
370                 375                 380

Val Pro Ile Ile Ile Ala Arg Thr Arg Val Pro Ala Lys Lys Leu Glu
385                 390                 395                 400

<210> SEQ ID NO 10
<211> LENGTH: 399
<212> TYPE: PRT
<213> ORGANISM: Gallus gallus

<400> SEQUENCE: 10

Met Ser Arg Asn Phe Ser Asp Thr Gly Ser Lys Lys Glu His Val Lys
1               5                   10                  15

Ile Thr Ser Glu Ala Lys Pro Gly Phe Leu Glu Arg Leu Ser Thr Ser
            20                  25                  30

Gly Gly Met Leu Ile Gly Leu Gly Thr Phe Leu Leu Ser Phe Tyr Leu
        35                  40                  45

Leu Phe Thr Asn Glu Gly Arg Ala Leu Arg Thr Ala Lys Ser Leu Asp
    50                  55                  60

Glu Gly Leu Ser Leu Val Ile Pro Leu Asp Asn Ile His Ser Val Ser
65                  70                  75                  80

Gln Gln Asn Glu Gly Arg Leu Val His Leu Ala Gly Ala Leu Ser Thr
                85                  90                  95

Ala Lys Pro Leu Phe Asp Pro Ser Tyr Gly Leu Ser Ile Gln Ala Val
            100                 105                 110

Lys Leu Lys Arg Lys Val Glu Met Tyr Gln Trp Val Glu Tyr Glu Asp
        115                 120                 125

Ser Arg Glu Tyr Glu Glu Asn Gly Glu Ile Lys Lys Glu Thr Lys Tyr
    130                 135                 140

Ser Tyr Asn Thr Glu Trp Lys Pro Glu Val Val Asn Ser Arg Asn Phe
145                 150                 155                 160

Asp Arg Glu Ile Gly His Lys Asn Pro Ser Ala Met Ala Val Glu Ser
                165                 170                 175

Phe Thr Ala Val Ser Pro Asn Val Gln Val Gly Ser Phe Val Leu Ser
            180                 185                 190

Lys Gly Leu Val Asp Lys Ile Asp Asp Phe Lys Gln Leu Ser Leu Ala
        195                 200                 205

His Leu Glu Asp Pro His Ala Asp Val Thr Arg Gly Gly Asp Tyr Phe
    210                 215                 220

Tyr His Ser Glu Asn Pro Arg Arg Pro Glu Val Gly Asp Leu Arg Val
225                 230                 235                 240

Ser Phe Phe Tyr Ala Gly Leu Ser Gly His Asp Pro His Leu Gly Ser
                245                 250                 255

Ala Asp Lys Val Thr Val Ile Ala Arg Gln Lys Gly Asp Gln Leu Val
            260                 265                 270

Pro Tyr His Thr Lys Ser Gly Asp Val Leu Gln Ile Leu Tyr Phe Gly
        275                 280                 285

Asp Leu Ser Val Glu Glu Val Phe Gln Lys Glu His Glu Ser Asn Thr
    290                 295                 300

Met Lys Thr Trp Ala Leu Arg Ala Ala Gly Trp Leu Ala Met Phe Val
305                 310                 315                 320

Gly Ile Ser Leu Met Thr Arg Ile Val Tyr Thr Leu Val Asp Trp Phe
                325                 330                 335
```

```
Pro Val Val Arg Asp Leu Val Asn Ile Gly Leu Lys Ala Phe Ala Phe
            340                 345                 350

Cys Val Ala Ser Ser Leu Ser Leu Leu Thr Ile Ser Ile Gly Trp Phe
            355                 360                 365

Phe Tyr Arg Pro Leu Trp Ala Leu Leu Ile Gly Leu Leu Ser Val Val
            370                 375                 380

Pro Ile Val Val Ala Lys Ser Arg Ile Pro Lys Lys His Gln
385                 390                 395

<210> SEQ ID NO 11
<211> LENGTH: 390
<212> TYPE: PRT
<213> ORGANISM: Zenopus tropicalis

<400> SEQUENCE: 11

Met Lys Glu His Thr Thr Val Arg Ser Glu Gln Lys Pro Gly Phe Leu
1               5                   10                  15

Glu Arg Leu Ser Asp Thr Ala Gly Gly Met Leu Val Gly Leu Leu Ala
            20                  25                  30

Phe Ser Leu Ser Phe Tyr Leu Leu Phe Thr Asn Glu Gly Arg Ala Val
            35                  40                  45

Gln Thr Ala Thr Ser Leu Asp Glu Gly Leu Ser Ile Val Val Pro Val
    50                  55                  60

Gly Asn Ile His Ser Ile Asp His Gln Asn Glu Ala Asn Leu Val His
65              70                  75                  80

Leu Ser Gly Ala Leu Arg Thr Ser Lys Pro Leu Tyr Asp Pro Asn Tyr
            85                  90                  95

Gly Val Ser Ile His Cys Val Lys Leu Lys Arg Gln Val Glu Met Tyr
            100                 105                 110

Gln Trp Ile Glu Tyr Glu Ser Arg Gln Tyr Glu Glu Asn Gly Glu
        115                 120                 125

Gln Lys Thr Glu Thr Arg Tyr Thr Tyr Asn Thr Glu Trp Arg Ser Glu
    130                 135                 140

Ile Val Ser Ser Arg His Phe Asp Arg Glu Ile Ala His Gln Asn Pro
145                 150                 155                 160

Ser Ala Met Ala Val Glu Ser Phe Thr Ala Val Ser Ser Asp Val Gln
            165                 170                 175

Val Gly Ser Tyr Tyr Leu Ser Lys Gly Leu Val Asp Lys Ile Asp Asn
            180                 185                 190

Phe Lys Gln Met Ser Leu Ser Gln Leu Gly Asn Pro His Ala Asp Val
            195                 200                 205

Ile Ala Asp Gly Gly Tyr Phe Tyr His Ser Ala Asn Pro Lys Ser Pro
    210                 215                 220

Glu Val Gly Asp Leu Arg Ile Ser Phe Trp Tyr Ala Gly Val Ala Leu
225                 230                 235                 240

Gly Gly Ala Gln Phe Gly Gln Pro Asp Met Val Ser Val Ile Ala Arg
            245                 250                 255

Gln Arg Gly Gly Glu Leu Gly Ala Tyr Lys Thr Lys Ser Gly Asp Val
            260                 265                 270

Leu Glu Leu Leu His Met Gly Thr Tyr Ser Ala Gln Glu Met Phe Glu
            275                 280                 285

Ala Glu His Lys Ser Asn Asn Leu Lys Thr Trp Ala Leu Arg Gly Ala
            290                 295                 300

Gly Trp Leu Met Met Phe Val Gly Ile Ser Leu Met Thr Lys Ile Phe
```

```
                    305                 310                 315                 320
Tyr Thr Leu Val Asp Trp Phe Pro Leu Val Arg Asp Leu Val Ser Leu
                325                 330                 335

Gly Leu Lys Ile Cys Ala Leu Cys Val Ser Ser Leu Ser Leu Leu
                340                 345                 350

Thr Ile Ala Ala Gly Trp Ile Phe Tyr Arg Pro Leu Leu Ala Leu Leu
                355                 360                 365

Leu Ser Ala Ala Ala Ile Gly Ile Ile Val Leu Ala Arg Ser Arg Val
                370                 375                 380

Pro Pro Lys Lys Tyr Gln
385                 390

<210> SEQ ID NO 12
<211> LENGTH: 402
<212> TYPE: PRT
<213> ORGANISM: Tetradon nigroviridis

<400> SEQUENCE: 12

Met Ser Ser Ala Gln Ser Ser Gly Lys Asn Pro Asn Lys His Thr Arg
1               5                   10                  15

Val Ser Ala Lys Ala Asn Pro Gly Phe Leu Glu Arg Leu Ser Glu Thr
                20                  25                  30

Ala Gly Gly Thr Leu Val Gly Ile Gly Leu Phe Phe Leu Ser Phe Tyr
                35                  40                  45

Val Leu Phe Thr Asn Glu Gly Arg Ala Leu Gln Thr Ser Ser Ser Leu
        50                  55                  60

Asp Glu Gly Leu Ser Arg Val Val Ser Leu Gly Ser Ser Ser Ser Leu
65                  70                  75                  80

Asp Pro Gln Asn Asn Asn His Leu Val His Leu Phe Ala Pro Leu Lys
                85                  90                  95

Thr Ala Gln Pro Leu His Asp Pro Asn Tyr Lys Val Val Gln Ala
                100                 105                 110

Val Lys Leu Lys Arg Gln Val Glu Met Tyr Gln Trp Val Glu His Gln
                115                 120                 125

Glu Ser Lys Asp Tyr Gln Glu Glu Gly Glu Thr Lys Thr Glu Thr Thr
                130                 135                 140

Tyr Thr Tyr Asn Thr Glu Trp Lys Ser Glu Leu Ile Asn Ser Arg His
145                 150                 155                 160

Phe Asp Lys Glu Ile Gly His Gln Asn Pro Ser Ala Met Ala Val Glu
                165                 170                 175

Ser Val Thr Val Val Ala Pro Glu Val Arg Val Gly Pro Phe Val Leu
                180                 185                 190

Ser Lys Gly Leu Val Glu Gln Ile Asp His Phe Gln Thr Leu Ser Leu
                195                 200                 205

Arg Asp Phe Pro Val Leu Asp Leu Glu Pro Phe Leu Ser Ile Asp Asp
                210                 215                 220

Asp Tyr Phe Tyr His Thr Glu His Pro Arg Arg Pro Glu Val Gly Asp
225                 230                 235                 240

Val Arg Val Arg Phe Ser Phe Ala Gly Leu Ser Gly Glu Ser Ser Arg
                245                 250                 255

Phe Gly Pro Pro Gln Pro Val Ser Val Val Ala Met Gln Arg Gly Glu
                260                 265                 270

His Leu Glu Pro Phe Lys Thr Arg Ser Gly Gly Thr Leu Glu Ile Leu
                275                 280                 285
```

```
Tyr Leu Gly Glu Leu Thr Ala Glu Glu Val Phe Ala Lys Glu His Gln
290                 295                 300

His Asn Ser Leu Lys Thr Trp Ala Leu Arg Ala Ala Gly Trp Ala Leu
305                 310                 315                 320

Met Phe Leu Ser Ile Gln Leu Ser Met Arg Ile Ile Tyr Thr Leu Val
                325                 330                 335

Asp Trp Val Pro Val Leu Arg Glu Leu Val Ser Leu Gly Leu Lys Val
                340                 345                 350

Leu Ala Leu Cys Leu Ser Cys Ser Leu Ser Leu Leu Thr Ile Ala Ala
                355                 360                 365

Gly Trp Leu Phe Tyr Arg Pro Leu Val Ala Ala Leu Ala Ala Leu
370                 375                 380

Ala Leu Val Pro Val Phe Leu Thr Arg Ser Gly Leu Pro Ala Lys Lys
385                 390                 395                 400

Asn Glu

<210> SEQ ID NO 13
<211> LENGTH: 376
<212> TYPE: PRT
<213> ORGANISM: Drosophila melanogaster

<400> SEQUENCE: 13

Met Ala Ser Leu Ser Glu Thr Leu Arg Ser His Trp Pro Ile Ala Leu
1               5                   10                  15

Phe Gly Val Ile Leu Phe Val Ala Gly Gly Thr Glu Leu Tyr Trp Asn
                20                  25                  30

Glu Gly Arg Ala Val His Asn Met Met Ala Leu Asp Glu Ala His Ala
            35                  40                  45

Asp Ile Tyr Ser Val Arg Phe Thr Glu Glu Gln Glu Val Gly Leu
        50                  55                  60

Glu Gly Arg Ile Val His Leu Ser Gly Pro Ile Leu Val Gly Glu Pro
65                  70                  75                  80

Leu Thr Glu Pro Asp Tyr Asn Ile Gln Leu Leu Ala Val Lys Leu Arg
                85                  90                  95

Arg Arg Val Gln Met Tyr Gln Trp Val Glu Ala Val Glu His Asn
            100                 105                 110

Tyr Gly Asp Ser Val Gly Thr Thr His Ser Asp Ser Arg Thr Tyr Tyr
            115                 120                 125

Tyr Thr Arg Glu Trp Arg Asp Lys Ile Val Asp Ser Arg Asn Phe Tyr
130                 135                 140

Asn Arg His Gly His Thr Asn Pro Ser His Phe Pro Ile Glu Ser His
145                 150                 155                 160

Val Gln Val Ala Asp Ala Val Phe Ile Gly Arg Tyr Glu Leu Gly Ala
                165                 170                 175

Glu Val Lys Glu Lys Phe Asn Asn Tyr Gln Glu Leu Thr Ser Asp Ile
            180                 185                 190

Arg Pro Glu Asp Ser Gly Val Lys Leu His Leu Gly Ile Tyr Tyr His
        195                 200                 205

Thr Asn Asp Val Phe Asn Pro Glu Val Gly Asp Leu Arg Leu Leu Phe
    210                 215                 220

Ser Phe Ala Gly Met Glu Gly Glu Val Phe Ser Val Gly Lys Leu
225                 230                 235                 240

Ser Gly Asn Lys Leu Val Pro Tyr Ile Thr Ser Arg Gly Val Pro Val
                245                 250                 255
```

```
Leu Leu Val Tyr Pro Gly Gly Leu Ser Val Gln Glu Val Phe Arg Leu
            260                 265                 270

Glu Ala Arg Ala Gln Val Leu His Thr Trp Trp Arg Phe Val Gly
        275                 280                 285

Trp Leu Leu Ile Phe Phe Gly Val Thr Cys Asn Thr Lys Ile Leu Arg
        290                 295                 300

Leu Leu Phe Val Arg Val Pro Leu Leu Val Ala Leu Ala Pro Asp Pro
305                 310                 315                 320

Gln Phe Pro Val Thr Gly Asn Leu Leu Ile Ala Phe Ser Leu Ala Leu
            325                 330                 335

Thr Ile Ala Ala Val Ala Trp Ile Leu His Arg Pro Val Ile Gly Ala
            340                 345                 350

Cys Leu Leu Leu Ala Gly Ala Ser Pro Tyr Val Trp Phe Thr Arg Asn
            355                 360                 365

Leu Val Asp Tyr His Arg Leu Asp
            370                 375

<210> SEQ ID NO 14
<211> LENGTH: 425
<212> TYPE: PRT
<213> ORGANISM: Rhizobium loti

<400> SEQUENCE: 14

Met Glu Phe Val Ala Ala Leu Arg Pro Arg Ser Ser Ala Ala Val Pro
1               5                   10                  15

Cys Gly Leu Leu Ala Ser Phe Val Ser Gly Glu Thr Met Ser Asp Ser
            20                  25                  30

Phe Arg Glu Val Thr Ser Val Ser Trp Phe Gly Arg Ile Lys Arg Ala
        35                  40                  45

Val Gly Gly Val Ile Phe Gly Leu Leu Leu Ile Val Leu Met Val Ile
    50                  55                  60

Gly Leu Phe Trp Asn Glu Gly Arg Ala Val Gln Thr Ala Arg Ser Leu
65                  70                  75                  80

Ala Glu Gly Ala Gly Ala Val Val Ala Ile Asn Ala Asp Ser Val Asp
                85                  90                  95

Ala Gly Asn Asp Gly Arg Leu Val His Val Ser Gly Pro Val Thr Ala
            100                 105                 110

Asp Gly Ser Leu Ser Asp Pro Asp Phe Gly Ile Ala Ala Gln Gly Leu
        115                 120                 125

Arg Leu Ser Arg Ser Val Glu Met Tyr Gln Trp Lys Glu Glu Ser Lys
    130                 135                 140

Ser Glu Thr Thr Lys Lys Leu Gly Gly Gly Glu Glu Thr Glu Thr Thr
145                 150                 155                 160

Tyr Ser Tyr Ser Lys Val Trp Asp Asp Ser Gln Ile Asp Ser Ser Asp
                165                 170                 175

Phe Lys Lys Pro Asp Gly His Gln Asn Pro Pro Met Ala Ile His Ser
            180                 185                 190

Arg Val Phe Gln Ile Pro Gln Gly Lys Leu Val Ala Phe Asp Leu Asp
        195                 200                 205

Thr Pro Val Leu Asp Arg Ile Asp Gly Asp Lys Ala Tyr Ser Leu Ser
    210                 215                 220

Ala Asn Gln Ser Ala Thr Ile Lys Ala Ala Tyr Thr Gly Thr Lys Pro
225                 230                 235                 240

Leu Ser Ile Val Asp Gly Arg Ile Tyr Leu Gly Asn Asp Asn Thr Thr
                245                 250                 255
```

Pro Ala Leu Gly Asp Tyr Arg Ile Gly Tyr Glu Leu Ala Pro Leu Gly
            260                 265                 270

Val Val Ser Ile Val Ala Arg Gln Ala Gly Ser Arg Phe Glu Pro Tyr
        275                 280                 285

Gln Thr Gln Ala Gly Asp Ala Leu Leu Met Val Asp Thr Gly Asn Val
    290                 295                 300

Pro Ala Asp Lys Met Phe Ala Glu Ala Val Ser Ala Asn Thr Leu Ile
305                 310                 315                 320

Thr Trp Leu Leu Arg Ala Gly Leu Leu Leu Thr Ile Gly Phe
                325                 330                 335

Ala Leu Phe Leu Ser Pro Ile Gly Val Ile Leu Asp Val Ile Pro Phe
                340                 345                 350

Leu Gly Ser Met Ala Arg Met Gly Thr Gly Ile Ile Ala Phe Phe Leu
                355                 360                 365

Ala Ile Leu Val Gly Thr Thr Thr Ile Ala Ile Ala Trp Phe Trp Tyr
            370                 375                 380

Arg Pro Val Leu Ala Ala Gly Ile Leu Ala Thr Gly Val Ile Ala Ala
385                 390                 395                 400

Ala Ala Val Tyr Tyr Leu Gly Arg Ser Arg Lys Ala Ala Ala Pro Met
                405                 410                 415

Ala Thr Pro Ser Thr Gly Thr Ala Thr
                420                 425

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
gtcagcccac ttcctagctg                                                 20

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
cctcgtctcc ttcttcacct                                                 20

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
agaatgaagg aaggctggtg                                                 20

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
tggtggagaa tgggactagc                                                    20

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
cgccgtggag acttttttcta                                                   20

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
acctggatcc tagggctcac                                                    20

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
gtcagcccac ttcctagctg                                                    20

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
cccaggtctt catggagttg                                                    20

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
atcttccggc tgtgaaactg                                                    20

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
agagggagtg cagagtccaa                                                    20

<210> SEQ ID NO 25
<211> LENGTH: 20
<212> TYPE: DNA

```
<213> ORGANISM: Artificial Sequence
<220> FEATURE:
<223> OTHER INFORMATION: Primer

<400> SEQUENCE: 25
caatgtcccg gaccgtatag                                                20

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
ggcgaaatgg acctagagga                                                20

<210> SEQ ID NO 27
<211> LENGTH: 27
<212> TYPE: DNA
<213> ORGANISM: Artificial Sequence
<220> FEATURE:
<223> OTHER INFORMATION: Primer

<400> SEQUENCE: 27
agttttcatt ctgttactgt ttctttt                                        27

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
ggcccttgat taccaaatcc                                                20

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
aactgtacgg tggggagatg                                                20

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
atcactccca tgtgtgacca                                                20

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
aagaacctgg gacagggagt                                                20
```

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
ctcctggagc cactcttcac                                           20

<210> SEQ ID NO 33
<211> LENGTH: 20
<212> TYPE: DNA
<213> ORGANISM: Artificial Sequence
<220> FEATURE:
<223> OTHER INFORMATION: Primer

<400> SEQUENCE: 33
tgatctggta gccctgaggt                                           20

<210> SEQ ID NO 34
<211> LENGTH: 21
<212> TYPE: DNA
<213> ORGANISM: Artificial Sequence
<220> FEATURE:
<223> OTHER INFORMATION: Primer

<400> SEQUENCE: 34
cacgaggcag gattaactca a                                         21

<210> SEQ ID NO 35
<211> LENGTH: 20
<212> TYPE: DNA
<213> ORGANISM: Artificial Sequence
<220> FEATURE:
<223> OTHER INFORMATION: Primer

<400> SEQUENCE: 35
cctgggctaa tctggacttg                                           20

<210> SEQ ID NO 36
<211> LENGTH: 20
<212> TYPE: DNA
<213> ORGANISM: Artificial Sequene
<220> FEATURE:
<223> OTHER INFORMATION: Primer

<400> SEQUENCE: 36
ctgatcctgt gcctttagcc                                           20

<210> SEQ ID NO 37
<211> LENGTH: 20
<212> TYPE: DNA
<213> ORGANISM: Artificial Sequence
<220> FEATURE:
<223> OTHER INFORMATION: Primer

<400> SEQUENCE: 37
cgtggacgag acagagtcag                                           20

<210> SEQ ID NO 38
<211> LENGTH: 20
<212> TYPE: DNA
<213> ORGANISM: Artificial Sequence
<220> FEATURE:

<223> OTHER INFORMATION: Primer

<400> SEQUENCE: 38
cgctcctgac attgaccaag					20

<210> SEQ ID NO 39
<211> LENGTH: 20
<212> TYPE: DNA
<213> ORGANISM: Artificial Sequence
<220> FEATURE:
<223> OTHER INFORMATION: Primer

<400> SEQUENCE: 39
gggtttctgt gctcacttcc					20

<210> SEQ ID NO 40
<211> LENGTH: 20
<212> TYPE: DNA
<213> ORGANISM: Artificial Sequence
<220> FEATURE:
<223> OTHER INFORMATION: Primer

<400> SEQUENCE: 40
tgcctcattc actggctatg					20

<210> SEQ ID NO 41
<211> LENGTH: 20
<212> TYPE: DNA
<213> ORGANISM: Artificial Sequence
<220> FEATURE:
<223> OTHER INFORMATION: Primer

<400> SEQUENCE: 41
tgttcagaaa tggccaacag					20

<210> SEQ ID NO 42
<211> LENGTH: 20
<212> TYPE: DNA
<213> ORGANISM: Artificial Sequence
<220> FEATURE:
<223> OTHER INFORMATION: Primer

<400> SEQUENCE: 42
ctcatcccaa ggctatggag					20

<210> SEQ ID NO 43
<211> LENGTH: 20
<212> TYPE: DNA
<213> ORGANISM: Artificial Sequence
<220> FEATURE:
<223> OTHER INFORMATION: Primer

<400> SEQUENCE: 43
cccatcctca tctagggaca					20

<210> SEQ ID NO 44
<211> LENGTH: 20
<212> TYPE: DNA
<213> ORGANISM: Artificial Sequence
<220> FEATURE:
<223> OTHER INFORMATION: Primer

<400> SEQUENCE: 44
ggaaacagca ggagaagctg					20

<210> SEQ ID NO 45
<211> LENGTH: 20
<212> TYPE: DNA
<213> ORGANISM: Artificial Sequence
<220> FEATURE:
<223> OTHER INFORMATION: Primer

<400> SEQUENCE: 45
tggtgttcac cagctcatgt                                                  20

<210> SEQ ID NO 46
<211> LENGTH: 20
<212> TYPE: DNA
<213> ORGANISM: Artificial Sequence
<220> FEATURE:
<223> OTHER INFORMATION: Primer

<400> SEQUENCE: 46
ttcctcttgg ggtaggaaag                                                  20

<210> SEQ ID NO 47
<211> LENGTH: 20
<212> TYPE: DNA
<213> ORGANISM: Artificial Sequence
<220> FEATURE:
<223> OTHER INFORMATION: Primer

<400> SEQUENCE: 47
tcctgaggag aaaagctgga                                                  20

<210> SEQ ID NO 48
<211> LENGTH: 20
<212> TYPE: DNA
<213> ORGANISM: Artificial Sequence
<220> FEATURE:
<223> OTHER INFORMATION: Primer

<400> SEQUENCE: 48
cgtgggcatt gtacaaccag                                                  20

<210> SEQ ID NO 49
<211> LENGTH: 22
<212> TYPE: DNA
<213> ORGANISM: Artificial Sequence
<220> FEATURE:
<223> OTHER INFORMATION: Primer

<400> SEQUENCE: 49
cgattaagag aaaaggttgg aa                                               22

<210> SEQ ID NO 50
<211> LENGTH: 25
<212> TYPE: DNA
<213> ORGANISM: Artificial Sequence
<220> FEATURE:
<223> OTHER INFORMATION: Primer

<400> SEQUENCE: 50
gagatttgat gaaattgctc atgta                                            25

<210> SEQ ID NO 51
<211> LENGTH: 20
<212> TYPE: DNA
<213> ORGANISM: Artificial Sequence
<220> FEATURE:
<223> OTHER INFORMATION: Primer -continued

<400> SEQUENCE: 51
ttgtgcctgc tgggagtaat                                          20

<210> SEQ ID NO 52
<211> LENGTH: 23
<212> TYPE: DNA
<213> ORGANISM: Artificial Sequence
<220> FEATURE:
<223> OTHER INFORMATION: Primer

<400> SEQUENCE: 52
atcctatggc tgaattcttt aca                                      23

<210> SEQ ID NO 53
<211> LENGTH: 20
<212> TYPE: DNA
<213> ORGANISM: Artificial Sequence
<220> FEATURE:
<223> OTHER INFORMATION: Probe

<400> SEQUENCE: 53
ctgtgtggcc accttgctga                                          20

<210> SEQ ID NO 54
<211> LENGTH: 20
<212> TYPE: DNA
<213> ORGANISM: Artificial Sequence
<220> FEATURE:
<223> OTHER INFORMATION: Probe

<400> SEQUENCE: 54
ctgtgtggcc acctcgctga                                          20

<210> SEQ ID NO 55
<211> LENGTH: 2846
<212> TYPE: DNA
<213> ORGANISM: Homo sapiens
<220> FEATURE:
<221> NAME/KEY: misc_feature
<223> OTHER INFORMATION: H3C1779.1
<220> FEATURE:
<221> NAME/KEY: CDS
<222> LOCATION: (260)..(1459)

<400> SEQUENCE: 55
aaagctttgc agtgcgcagg cgcatcaatg aggtactgca atgtcccgga ccgtatagtt     60
tccaggacgt ctcgccgcgc gcatgcgcag aaacactggg cacaggggga ggtaactgca    120
gtaagtcccg cttggccctg gagtccacgc ggattttcga agctggggct ggcaagaggc    180
cgctggacac cacgctccag tcgtcagccc acttcctagc tgaacagcgc gaggcggcgg    240
cagcgagccg ggtcccacc atg gcc gcg aat tat tcc agt acc agt acc cgg    292
                     Met Ala Ala Asn Tyr Ser Ser Thr Ser Thr Arg
                      1               5                  10 aga gaa cat gtc aaa gtt aaa acc agc tcc cag cca ggc ttc ctg gaa    340
Arg Glu His Val Lys Val Lys Thr Ser Ser Gln Pro Gly Phe Leu Glu
         15                  20                  25 cgg ctg agc gag acc tcg ggt ggg atg ttt gtg ggg ctc atg gcc ttc    388
Arg Leu Ser Glu Thr Ser Gly Gly Met Phe Val Gly Leu Met Ala Phe
     30                  35                  40 ctg ctc tcc ttc tac cta att ttc acc aat gag ggc cgc gca ttg aag    436
Leu Leu Ser Phe Tyr Leu Ile Phe Thr Asn Glu Gly Arg Ala Leu Lys
 45                  50                  55 acg gca acc tca ttg gct gag ggg ctc tcg ctt gtg gtg tct ccc gac    484

```
                Thr Ala Thr Ser Leu Ala Glu Gly Leu Ser Leu Val Ser Pro Asp
                60              65                  70                  75 agc atc cac agt gtg gct ccg gag aat gaa gga agg ctg gtc cac atc           532
Ser Ile His Ser Val Ala Pro Glu Asn Glu Gly Arg Leu Val His Ile
                    80                  85                  90 att ggc gcc tta cgg aca tcc aag ctt ttg tct gat cca aac tat ggg           580
Ile Gly Ala Leu Arg Thr Ser Lys Leu Leu Ser Asp Pro Asn Tyr Gly
                95                  100                 105 gtc cat ctt ccg gct gtg aaa ctg cgg agg cac gtg gag atg tac caa           628
Val His Leu Pro Ala Val Lys Leu Arg Arg His Val Glu Met Tyr Gln
            110                 115                 120 tgg gta gaa act gag gag tcc agg gag tac acc gag gat ggg cag gtg           676
Trp Val Glu Thr Glu Glu Ser Arg Glu Tyr Thr Glu Asp Gly Gln Val
        125                 130                 135 aag aag gag acg agg tat tcc tac aac act gaa tgg agg tca gaa atc           724
Lys Lys Glu Thr Arg Tyr Ser Tyr Asn Thr Glu Trp Arg Ser Glu Ile
140                 145                 150                 155 atc aac agc aaa aac ttc gac cga gag att ggc cac aaa aac ccc agt           772
Ile Asn Ser Lys Asn Phe Asp Arg Glu Ile Gly His Lys Asn Pro Ser
                    160                 165                 170 gcc atg gca gtg gag tca ttc atg gca aca gcc ccc ttt gtc caa att           820
Ala Met Ala Val Glu Ser Phe Met Ala Thr Ala Pro Phe Val Gln Ile
                175                 180                 185 ggc agg ttt ttc ctc tcg tca ggc ctc atc gac aaa gtc gac aac ttc           868
Gly Arg Phe Phe Leu Ser Ser Gly Leu Ile Asp Lys Val Asp Asn Phe
            190                 195                 200 aag tcc ctg agc cta tcc aag ctg gag gac cct cat gtg gac atc att           916
Lys Ser Leu Ser Leu Ser Lys Leu Glu Asp Pro His Val Asp Ile Ile
        205                 210                 215 cgc cgt gga gac ttt ttc tac cac agc gaa aat ccc aag tat cca gag           964
Arg Arg Gly Asp Phe Phe Tyr His Ser Glu Asn Pro Lys Tyr Pro Glu
220                 225                 230                 235 gtg gga gac ttg cgt gtc tcc ttt tcc tat gct gga ctg agc ggc gat          1012
Val Gly Asp Leu Arg Val Ser Phe Ser Tyr Ala Gly Leu Ser Gly Asp
                    240                 245                 250 gac cct gac ctg ggc cca gct cac gtg gtc act gtg att gcc cgg cag          1060
Asp Pro Asp Leu Gly Pro Ala His Val Val Thr Val Ile Ala Arg Gln
                255                 260                 265 cgg ggt gac cag cta gtc cca ttc tcc acc aag tct ggg gat acc tta          1108
Arg Gly Asp Gln Leu Val Pro Phe Ser Thr Lys Ser Gly Asp Thr Leu
            270                 275                 280 ctg ctc ctg cac cac ggg gac ttc tca gca gag gag gtg ttt cat aga          1156
Leu Leu Leu His His Gly Asp Phe Ser Ala Glu Glu Val Phe His Arg
        285                 290                 295 gaa cta agg agc aac tcc atg aag acc tgg ggc ctg cgg gca gct ggc          1204
Glu Leu Arg Ser Asn Ser Met Lys Thr Trp Gly Leu Arg Ala Ala Gly
300                 305                 310                 315 tgg atg gcc atg ttc atg ggc ctc aac ctt atg aca cgg atc ctc tac          1252
Trp Met Ala Met Phe Met Gly Leu Asn Leu Met Thr Arg Ile Leu Tyr
                    320                 325                 330 acc ttg gtg gac tgg ttt cct gtt ttc cga gac ctg gtc aac att ggc          1300
Thr Leu Val Asp Trp Phe Pro Val Phe Arg Asp Leu Val Asn Ile Gly
                335                 340                 345 ctg aaa gcc ttt gcc ttc tgt gtg gcc acc tcg ctg acc ctg ctg acc          1348
Leu Lys Ala Phe Ala Phe Cys Val Ala Thr Ser Leu Thr Leu Leu Thr
            350                 355                 360 gtg gcg gct ggc tgg ctc ttc tac cga ccc ctg tgg gcc ctc ctc att          1396
Val Ala Ala Gly Trp Leu Phe Tyr Arg Pro Leu Trp Ala Leu Leu Ile
        365                 370                 375
```

| | | |
|---|---|---|
| gcc ggc ctg gcc ctt gtg ccc atc ctt gtt gct cgg aca cgg gtg cca<br>Ala Gly Leu Ala Leu Val Pro Ile Leu Val Ala Arg Thr Arg Val Pro<br>380                            385                            390                            395 | | 1444 |
| gcc aaa aag ttg gag tgaaaagacc ctggcacccg cccgacacct gcgtgagccc<br>Ala Lys Lys Leu Glu<br>                     400 | | 1499 |
| taggatccag gtcctctctc acctctgacc cagctccatg ccagagcagg agccccggtc | | 1559 |
| aattttggac tctgcactcc ctctcctctt caggggccag acttggcagc atgtgcacca | | 1619 |
| ggttggtgtt caccagctca tgtcttcccc acatctcttc ttgccagtaa gcagctttgg | | 1679 |
| tgggcagcag cagctcatga atggcaagct gacagcttct cctgctgttt ccttcctctc | | 1739 |
| ttggactgag tgggtacggc cagccactca gcccattggc agctgacaac gcagacacgc | | 1799 |
| tctacggagg cctgctgata aagggctcag ccttgccgtg tgctgcttct catcactgca | | 1859 |
| cacaagtgcc atgctttgcc accaccacca agcacatctg tgatcctgaa gggcggccgt | | 1919 |
| tagtcattac tgctgagtcc tgggtcacca gcagacacac tgggcatgga cccctcaaag | | 1979 |
| caggcacacc caaaacacaa gtctgtggct agaacctgat gtggtgttta aagagaaga | | 2039 |
| aacactgaag atgtcctgag gagaaaagct ggacatatac tgggcttcac acttatctta | | 2099 |
| tggcttggca gaatctttgt agtgtgtggg atctctgaag gccctattta gttttctctt | | 2159 |
| cgttactttg ctgcttcatg tgtactttcc taccccaaga ggaagttttc tgaaataaga | | 2219 |
| tttaaaaaca aaacaaaaaa aacacttaat atttcagact gttacaggaa cacccttta | | 2279 |
| gtctgtcagt tgaattcaga gcactgaaag gtgttaaatt ggggtatgtg gtttgattga | | 2339 |
| taaaaagtta cctctcagta tttttgtgtca ctgagaagct ttacaatgga tgcttttgaa | | 2399 |
| acaagtatca gcaaaaggat ttgttttcac tctgggagga gagggtggag aaagcacttg | | 2459 |
| ctttcatcct ctggcatcgg aaactcccct atgcacttga agatggttta aaagattaaa | | 2519 |
| gaaacgatta agagaaaagg ttggaagctt tatactaaat gggctccttc atggtgacgc | | 2579 |
| cccgtcaacc acaatcaaga actgaggcct gaggctggtt gtacaatgcc cacgcctgcc | | 2639 |
| tggctgcttt cacctgggag tgctttcgat gtgggcacct gggcttccta gggctgcttc | | 2699 |
| tgagtggttc tttcacgtgt tgtgtccata gctttagtct tcctaaataa gatccaccca | | 2759 |
| cacctaagtc acagaatttc taagttcccc aactactctc acacccttt aaagataaag | | 2819 |
| tatgttgtaa ccaggatgtc ttaaatg | | 2846 |

<210> SEQ ID NO 56
<211> LENGTH: 400
<212> TYPE: PRT
<213> ORGANISM: Homo sapiens

<400> SEQUENCE: 56

Met Ala Ala Asn Tyr Ser Ser Thr Ser Thr Arg Arg Glu His Val Lys
1               5                    10                  15

Val Lys Thr Ser Ser Gln Pro Gly Phe Leu Glu Arg Leu Ser Glu Thr
                  20                    25                    30

Ser Gly Gly Met Phe Val Gly Leu Met Ala Phe Leu Leu Ser Phe Tyr
                  35                    40                    45

Leu Ile Phe Thr Asn Glu Gly Arg Ala Leu Lys Thr Ala Thr Ser Leu
    50                    55                    60

Ala Glu Gly Leu Ser Leu Val Val Ser Pro Asp Ser Ile His Ser Val
65                    70                    75                    80

Ala Pro Glu Asn Glu Gly Arg Leu Val His Ile Ile Gly Ala Leu Arg
                  85                    90                    95

-continued

```
Thr Ser Lys Leu Leu Ser Asp Pro Asn Tyr Gly Val His Leu Pro Ala
            100                 105                 110

Val Lys Leu Arg Arg His Val Glu Met Tyr Gln Trp Val Glu Thr Glu
        115                 120                 125

Glu Ser Arg Glu Tyr Thr Glu Asp Gly Gln Val Lys Lys Glu Thr Arg
    130                 135                 140

Tyr Ser Tyr Asn Thr Glu Trp Arg Ser Glu Ile Ile Asn Ser Lys Asn
145                 150                 155                 160

Phe Asp Arg Glu Ile Gly His Lys Asn Pro Ser Ala Met Ala Val Glu
                165                 170                 175

Ser Phe Met Ala Thr Ala Pro Phe Val Gln Ile Gly Arg Phe Phe Leu
            180                 185                 190

Ser Ser Gly Leu Ile Asp Lys Val Asp Asn Phe Lys Ser Leu Ser Leu
        195                 200                 205

Ser Lys Leu Glu Asp Pro His Val Asp Ile Ile Arg Arg Gly Asp Phe
    210                 215                 220

Phe Tyr His Ser Glu Asn Pro Lys Tyr Pro Glu Val Gly Asp Leu Arg
225                 230                 235                 240

Val Ser Phe Ser Tyr Ala Gly Leu Ser Gly Asp Asp Pro Asp Leu Gly
                245                 250                 255

Pro Ala His Val Val Thr Val Ile Ala Arg Gln Arg Gly Asp Gln Leu
            260                 265                 270

Val Pro Phe Ser Thr Lys Ser Gly Asp Thr Leu Leu Leu His His
        275                 280                 285

Gly Asp Phe Ser Ala Glu Glu Val Phe His Arg Glu Leu Arg Ser Asn
    290                 295                 300

Ser Met Lys Thr Trp Gly Leu Arg Ala Ala Gly Trp Met Ala Met Phe
305                 310                 315                 320

Met Gly Leu Asn Leu Met Thr Arg Ile Leu Tyr Thr Leu Val Asp Trp
                325                 330                 335

Phe Pro Val Phe Arg Asp Leu Val Asn Ile Gly Leu Lys Ala Phe Ala
            340                 345                 350

Phe Cys Val Ala Thr Ser Leu Thr Leu Leu Thr Val Ala Ala Gly Trp
        355                 360                 365

Leu Phe Tyr Arg Pro Leu Trp Ala Leu Leu Ile Ala Gly Leu Ala Leu
    370                 375                 380

Val Pro Ile Leu Val Ala Arg Thr Arg Val Pro Ala Lys Lys Leu Glu
385                 390                 395                 400
```

<210> SEQ ID NO 57
<211> LENGTH: 2243
<212> TYPE: DNA
<213> ORGANISM: Homo sapiens
<220> FEATURE:
<221> NAME/KEY: misc_feature
<223> OTHER INFORMATION: H3C1779.2
<220> FEATURE:
<221> NAME/KEY: CDS
<222> LOCATION: (260)..(1459)

<400> SEQUENCE: 57

```
aaagctttgc agtgcgcagg cgcatcaatg aggtactgca atgtcccgga ccgtatagtt      60
tccaggacgt ctcgccgcgc gcatgcgcag aaacactggg cacaggggga ggtaactgca     120
gtaagtcccg cttggccctg gagtccacgc ggattttcga agctgggct  ggcaagaggc     180 cgctggacac cacgctccag tcgtcagccc acttcctagc tgaacagcgc gaggcggcgg     240
```

```
cagcgagccg gtcccacc atg gcc gcg aat tat tcc agt acc agt acc cgg      292
                    Met Ala Ala Asn Tyr Ser Ser Thr Ser Thr Arg
                     1               5                  10 aga gaa cat gtc aaa gtt aaa acc agc tcc cag cca ggc ttc ctg gaa      340
Arg Glu His Val Lys Val Lys Thr Ser Ser Gln Pro Gly Phe Leu Glu
            15                  20                  25 cgg ctg agc gag acc tcg ggt ggg atg ttt gtg ggg ctc atg gcc ttc      388
Arg Leu Ser Glu Thr Ser Gly Gly Met Phe Val Gly Leu Met Ala Phe
         30                  35                  40 ctg ctc tcc ttc tac cta att ttc acc aat gag ggc cgc gca ttg aag      436
Leu Leu Ser Phe Tyr Leu Ile Phe Thr Asn Glu Gly Arg Ala Leu Lys
     45                  50                  55 acg gca acc tca ttg gct gag ggg ctc tcg ctt gtg gtg tct ccc gac      484
Thr Ala Thr Ser Leu Ala Glu Gly Leu Ser Leu Val Val Ser Pro Asp
 60              65                  70                  75 agc atc cac agt gtg gct ccg gag aat gaa gga agg ctg gtg cac atc      532
Ser Ile His Ser Val Ala Pro Glu Asn Glu Gly Arg Leu Val His Ile
                 80                  85                  90 att ggc gcc tta cgg aca tcc aag ctt ttg tct gat cca aac tat ggg      580
Ile Gly Ala Leu Arg Thr Ser Lys Leu Leu Ser Asp Pro Asn Tyr Gly
             95                 100                 105 gtc cat ctt ccg gct gtg aaa ctg cgg agg cac gtg gag atg tac caa      628
Val His Leu Pro Ala Val Lys Leu Arg Arg His Val Glu Met Tyr Gln
         110                 115                 120 tgg gta gaa act gag gag tcc agg gag tac acc gag gat ggg cag gtg      676
Trp Val Glu Thr Glu Glu Ser Arg Glu Tyr Thr Glu Asp Gly Gln Val
     125                 130                 135 aag aag gag acg agg tat tcc tac aac act gaa tgg agg tca gaa atc      724
Lys Lys Glu Thr Arg Tyr Ser Tyr Asn Thr Glu Trp Arg Ser Glu Ile
140                 145                 150                 155 atc aac agc aaa aac ttc gac cga gag att ggc cac aaa aac ccc agt      772
Ile Asn Ser Lys Asn Phe Asp Arg Glu Ile Gly His Lys Asn Pro Ser
                 160                 165                 170 gcc atg gca gtg gag tca ttc atg gca aca gcc ccc ttt gtc caa att      820
Ala Met Ala Val Glu Ser Phe Met Ala Thr Ala Pro Phe Val Gln Ile
             175                 180                 185 ggc agg ttt ttc ctc tcg tca ggc ctc atc gac aaa gtc gac aac ttc      868
Gly Arg Phe Phe Leu Ser Ser Gly Leu Ile Asp Lys Val Asp Asn Phe
         190                 195                 200 aag tcc ctg agc cta tcc aag ctg gag gac cct cat gtg gac atc att      916
Lys Ser Leu Ser Leu Ser Lys Leu Glu Asp Pro His Val Asp Ile Ile
     205                 210                 215 cgc cgt gga gac ttt ttc tac cac agc gaa aat ccc aag tat cca gag      964
Arg Arg Gly Asp Phe Phe Tyr His Ser Glu Asn Pro Lys Tyr Pro Glu
220                 225                 230                 235 gtg gga gac ttg cgt gtc tcc ttt tcc tat gct gga ctg agc ggc gat     1012
Val Gly Asp Leu Arg Val Ser Phe Ser Tyr Ala Gly Leu Ser Gly Asp
                 240                 245                 250 gac cct gac ctg ggc cca gct cac gtg gtc act gtg att gcc cgg cag     1060
Asp Pro Asp Leu Gly Pro Ala His Val Val Thr Val Ile Ala Arg Gln
             255                 260                 265 cgg ggt gac cag cta gtc cca ttc tcc acc aag tct ggg gat acc tta     1108
Arg Gly Asp Gln Leu Val Pro Phe Ser Thr Lys Ser Gly Asp Thr Leu
         270                 275                 280 ctg ctc ctg cac cac ggg gac ttc tca gca gag gag gtg ttt cat aga     1156
Leu Leu Leu His His Gly Asp Phe Ser Ala Glu Glu Val Phe His Arg
     285                 290                 295 gaa cta agg agc aac tcc atg aag acc tgg ggc ctg cgg gca gct ggc     1204
Glu Leu Arg Ser Asn Ser Met Lys Thr Trp Gly Leu Arg Ala Ala Gly
```

```
                300           305           310           315
tgg atg gcc atg ttc atg ggc ctc aac ctt atg aca cgg atc ctc tac    1252
Trp Met Ala Met Phe Met Gly Leu Asn Leu Met Thr Arg Ile Leu Tyr
                320                       325                330 acc ttg gtg gac tgg ttt cct gtt ttc cga gac ctg gtc aac att ggc    1300
Thr Leu Val Asp Trp Phe Pro Val Phe Arg Asp Leu Val Asn Ile Gly
            335                       340                   345 ctg aaa gcc ttt gcc ttc tgt gtg gcc acc tcg ctg acc ctg ctg acc    1348
Leu Lys Ala Phe Ala Phe Cys Val Ala Thr Ser Leu Thr Leu Leu Thr
        350                       355                   360 gtg gcg gct ggc tgg ctc ttc tac cga ccc ctg tgg gcc ctc ctc att    1396
Val Ala Ala Gly Trp Leu Phe Tyr Arg Pro Leu Trp Ala Leu Leu Ile
    365                       370                   375 gcc ggc ctg gcc ctt gtg ccc atc ctt gtt gct cgg aca cgg gtg cca    1444
Ala Gly Leu Ala Leu Val Pro Ile Leu Val Ala Arg Thr Arg Val Pro
380                       385                   390                   395 gcc aaa aag ttg gag tgaaaagacc ctggcacccg cccgacacct gcgtgagcct    1499
Ala Lys Lys Leu Glu
                400 gaggctggtt gtacaatgcc cacgcctgcc tggctgcttt cacctgggag tgctttcgat    1559 gtgggcacct gggcttccta gggctgcttc tgagtggttc tttcacgtgt tgtgtccata    1619 gctttagtct tcctaaataa gatccaccca cacctaagtc acagaatttc taagttcccc    1679 aactactctc acacccttttt aaagataaag tatgttgtaa ccaggatgtc ttaaatgatt    1739 ctttgtgtac cttttctgtc atattcagaa accgttttgt gcctgctggg agtaattcct    1799 ttagcaatta agtatttggt agctgaataa ggggtcagaa cttctgaaac cagagatctg    1859 taatcatctc tattggcctg gggtgcctgt gctataaatg agtttcttca catgaaaaac    1919 acagccagcc caagatgact tatctgggtt taggattcaa tagtattcac taactgctta    1979 ttacatgagc aatttcatca aatctccaaa ctcttaaagg atgctttcgg aaaacacgct    2039 gtatacctag atgatgacta aatgcaaaat ccttgggctt tggttttttt ctagtaagga    2099 ttttaaataa ctgccgactt caaaagtgtt cttaaaacga agataatgt taagaaaaat    2159 ttgaaagctt tggaaaacca aatttgtaat atcattgtat ttttattaa aagttttgta    2219 ataaatttct aaattatctt ctgg                                           2243
```

<210> SEQ ID NO 58
<211> LENGTH: 400
<212> TYPE: PRT
<213> ORGANISM: Homo sapiens

<400> SEQUENCE: 58

Met Ala Ala Asn Tyr Ser Ser Thr Ser Thr Arg Arg Glu His Val Lys
1               5                   10                  15

Val Lys Thr Ser Ser Gln Pro Gly Phe Leu Glu Arg Leu Ser Glu Thr
            20                  25                  30

Ser Gly Gly Met Phe Val Gly Leu Met Ala Phe Leu Leu Ser Phe Tyr
        35                  40                  45

Leu Ile Phe Thr Asn Glu Gly Arg Ala Leu Lys Thr Ala Thr Ser Leu
    50                  55                  60

Ala Glu Gly Leu Ser Leu Val Val Ser Pro Asp Ser Ile His Ser Val
65                  70                  75                  80

Ala Pro Glu Asn Glu Gly Arg Leu Val His Ile Ile Gly Ala Leu Arg
                85                  90                  95

Thr Ser Lys Leu Leu Ser Asp Pro Asn Tyr Gly Val His Leu Pro Ala

```
                100                 105                 110
        Val Lys Leu Arg Arg His Val Glu Met Tyr Gln Trp Val Glu Thr Glu
                115                 120                 125

Glu Ser Arg Glu Tyr Thr Glu Asp Gly Gln Val Lys Lys Glu Thr Arg
            130                 135                 140

Tyr Ser Tyr Asn Thr Glu Trp Arg Ser Glu Ile Ile Asn Ser Lys Asn
        145                 150                 155                 160

Phe Asp Arg Glu Ile Gly His Lys Asn Pro Ser Ala Met Ala Val Glu
                        165                 170                 175

Ser Phe Met Ala Thr Ala Pro Phe Val Gln Ile Gly Arg Phe Phe Leu
                    180                 185                 190

Ser Ser Gly Leu Ile Asp Lys Val Asp Asn Phe Lys Ser Leu Ser Leu
                195                 200                 205

Ser Lys Leu Glu Asp Pro His Val Asp Ile Ile Arg Arg Gly Asp Phe
            210                 215                 220

Phe Tyr His Ser Glu Asn Pro Lys Tyr Pro Glu Val Gly Asp Leu Arg
        225                 230                 235                 240

Val Ser Phe Ser Tyr Ala Gly Leu Ser Gly Asp Asp Pro Asp Leu Gly
                        245                 250                 255

Pro Ala His Val Val Thr Val Ile Ala Arg Gln Arg Gly Asp Gln Leu
                    260                 265                 270

Val Pro Phe Ser Thr Lys Ser Gly Asp Thr Leu Leu Leu His His
                275                 280                 285

Gly Asp Phe Ser Ala Glu Glu Val Phe His Arg Glu Leu Arg Ser Asn
            290                 295                 300

Ser Met Lys Thr Trp Gly Leu Arg Ala Ala Gly Trp Met Ala Met Phe
        305                 310                 315                 320

Met Gly Leu Asn Leu Met Thr Arg Ile Leu Tyr Thr Leu Val Asp Trp
                        325                 330                 335

Phe Pro Val Phe Arg Asp Leu Val Asn Ile Gly Leu Lys Ala Phe Ala
                    340                 345                 350

Phe Cys Val Ala Thr Ser Leu Thr Leu Leu Thr Val Ala Ala Gly Trp
                355                 360                 365

Leu Phe Tyr Arg Pro Leu Trp Ala Leu Leu Ile Ala Gly Leu Ala Leu
            370                 375                 380

Val Pro Ile Leu Val Ala Arg Thr Arg Val Pro Ala Lys Lys Leu Glu
        385                 390                 395                 400

<210> SEQ ID NO 59
<211> LENGTH: 3353
<212> TYPE: DNA
<213> ORGANISM: Homo sapiens
<220> FEATURE:
<221> NAME/KEY: misc_feature
<223> OTHER INFORMATION: H3C1779.3
<220> FEATURE:
<221> NAME/KEY: CDS
<222> LOCATION: (260)..(1459)

<400> SEQUENCE: 59
aaagctttgc agtgcgcagg cgcatcaatg aggtactgca atgtcccgga ccgtatagtt      60
tccaggacgt ctcgccgcgc gcatgcgcag aaacactggg cacaggggga ggtaactgca     120
gtaagtcccg cttggccctg gagtccacgg gatttttcga agctggggct ggcaagaggc     180
cgctggacac cacgctccag tcgtcagccc acttcctagc tgaacagcgc gaggcggcgg     240
cagcgagccg ggtcccacc atg gcc gcg aat tat tcc agt acc agt acc cgg     292
```

```
                    Met Ala Ala Asn Tyr Ser Ser Thr Ser Thr Arg
                     1               5                  10 aga gaa cat gtc aaa gtt aaa acc agc tcc cag cca ggc ttc ctg gaa        340
Arg Glu His Val Lys Val Lys Thr Ser Ser Gln Pro Gly Phe Leu Glu
             15                  20                  25 cgg ctg agc gag acc tcg ggt ggg atg ttt gtg ggg ctc atg gcc ttc        388
Arg Leu Ser Glu Thr Ser Gly Gly Met Phe Val Gly Leu Met Ala Phe
         30                  35                  40 ctc ctc tcc ttc tac cta att ttc acc aat gag ggc cgc gca ttg aag        436
Leu Leu Ser Phe Tyr Leu Ile Phe Thr Asn Glu Gly Arg Ala Leu Lys
     45                  50                  55 acg gca acc tca ttg gct gag ggg ctc tcg ctt gtg gtg tct ccc gac        484
Thr Ala Thr Ser Leu Ala Glu Gly Leu Ser Leu Val Val Ser Pro Asp
 60                  65                  70                  75 agc atc cac agt gtg gct ccg gag aat gaa gga agg ctg gtg cac atc        532
Ser Ile His Ser Val Ala Pro Glu Asn Glu Gly Arg Leu Val His Ile
                 80                  85                  90 att ggc gcc tta cgg aca tcc aag ctt ttg tct gat cca aac tat ggg        580
Ile Gly Ala Leu Arg Thr Ser Lys Leu Leu Ser Asp Pro Asn Tyr Gly
             95                 100                 105 gtc cat ctt ccg gct gtg aaa ctg cgg agg cac gtg gag atg tac caa        628
Val His Leu Pro Ala Val Lys Leu Arg Arg His Val Glu Met Tyr Gln
         110                 115                 120 tgg gta gaa act gag gag tcc agg gag tac acc gag gat ggg cag gtg        676
Trp Val Glu Thr Glu Glu Ser Arg Glu Tyr Thr Glu Asp Gly Gln Val
     125                 130                 135 aag aag gag acg agg tat tcc tac aac act gaa tgg agg tca gaa atc        724
Lys Lys Glu Thr Arg Tyr Ser Tyr Asn Thr Glu Trp Arg Ser Glu Ile
140                 145                 150                 155 atc aac agc aaa aac ttc gac cga gag att ggc cac aaa aac ccc agt        772
Ile Asn Ser Lys Asn Phe Asp Arg Glu Ile Gly His Lys Asn Pro Ser
                 160                 165                 170 gcc atg gca gtg gag tca ttc atg gca aca gcc ccc ttt gtc caa att        820
Ala Met Ala Val Glu Ser Phe Met Ala Thr Ala Pro Phe Val Gln Ile
             175                 180                 185 ggc agg ttt ttc ctc tcg tca ggc ctc atc gac aaa gtc gac aac ttc        868
Gly Arg Phe Phe Leu Ser Ser Gly Leu Ile Asp Lys Val Asp Asn Phe
         190                 195                 200 aag tcc ctg agc cta tcc aag ctg gag gac cct cat gtg gac atc att        916
Lys Ser Leu Ser Leu Ser Lys Leu Glu Asp Pro His Val Asp Ile Ile
     205                 210                 215 cgc cgt gga gac ttt ttc tac cac agc gaa aat ccc aag tat cca gag        964
Arg Arg Gly Asp Phe Phe Tyr His Ser Glu Asn Pro Lys Tyr Pro Glu
220                 225                 230                 235 gtg gga gac ttg cgt gtc tcc ttt tcc tat gct gga ctg agc ggc gat       1012
Val Gly Asp Leu Arg Val Ser Phe Ser Tyr Ala Gly Leu Ser Gly Asp
                 240                 245                 250 gac cct gac ctg ggc cca gct cac gtg gtc act gtg att gcc cgg cag       1060
Asp Pro Asp Leu Gly Pro Ala His Val Val Thr Val Ile Ala Arg Gln
             255                 260                 265 cgg ggt gac cag cta gtc cca ttc tcc acc aag tct ggg gat acc tta       1108
Arg Gly Asp Gln Leu Val Pro Phe Ser Thr Lys Ser Gly Asp Thr Leu
         270                 275                 280 ctg ctc ctg cac cac ggg gac ttc tca gca gag gag gtg ttt cat aga       1156
Leu Leu Leu His His Gly Asp Phe Ser Ala Glu Glu Val Phe His Arg
     285                 290                 295 gaa cta agg agc aac tcc atg aag acc tgg ggc ctg cgg gca gct ggc       1204
Glu Leu Arg Ser Asn Ser Met Lys Thr Trp Gly Leu Arg Ala Ala Gly
300                 305                 310                 315
```

```
tgg atg gcc atg ttc atg ggc ctc aac ctt atg aca cgg atc ctc tac     1252
Trp Met Ala Met Phe Met Gly Leu Asn Leu Met Thr Arg Ile Leu Tyr
            320                 325                 330 acc ttg gtg gac tgg ttt cct gtc ttc cga gac ctg gtc aac att ggc     1300
Thr Leu Val Asp Trp Phe Pro Val Phe Arg Asp Leu Val Asn Ile Gly
            335                 340                 345 ctg aaa gcc ttt gcc ttc tgt gtg gcc acc tcg ctg acc ctg ctg acc     1348
Leu Lys Ala Phe Ala Phe Cys Val Ala Thr Ser Leu Thr Leu Leu Thr
            350                 355                 360 gtg gcg gct ggc tgg ctc ttc tac cga ccc ctg tgg gcc ctc ctc att     1396
Val Ala Ala Gly Trp Leu Phe Tyr Arg Pro Leu Trp Ala Leu Leu Ile
365                 370                 375 gcc ggc ctg gcc ctt gtg ccc atc ctt gtt gct cgg aca cgg gtg cca     1444
Ala Gly Leu Ala Leu Val Pro Ile Leu Val Ala Arg Thr Arg Val Pro
380                 385                 390                 395 gcc aaa aag ttg gag tgaaaagacc ctggcacccg cccgacacct gcgtgagccc     1499
Ala Lys Lys Leu Glu
            400 taggatccag gtcctctctc acctctgacc cagctccatg ccagagcagg agccccggtc   1559 aattttggac tctgcactcc ctctcctctt caggggccag acttggcagc atgtgcacca   1619 ggttggtgtt caccagctca tgtcttcccc acatctcttc ttgccagtaa gcagctttgg   1679 tgggcagcag cagctcatga atggcaagct gacagcttct cctgctgttt ccttcctctc   1739 ttggactgag tgggtacggc cagccactca gcccattggc agctgacaac gcagacacgc   1799 tctacggagg cctgctgata aagggctcag ccttgccgtg tgctgcttct catcactgca   1859 cacaagtgcc atgctttgcc accaccacca agcacatctg tgatcctgaa gggcggccgt   1919 tagtcattac tgctgagtcc tgggtcacca gcagacacac tgggcatgga cccctcaaag   1979 caggcacacc caaaacacaa gtctgtggct agaacctgat gtggtgttta aaagagaaga   2039 aacactgaag atgtcctgag gagaaaagct ggacatatac tgggcttcac acttatctta   2099 tggcttggca gaatctttgt agtgtgtggg atctctgaag ccctatttta gttttctt     2159 cgttactttg ctgcttcatg tgtactttcc taccccaaga ggaagttttc tgaaataaga   2219 tttaaaaaca aaacaaaaaa aacacttaat atttcagact gttacaggaa acacccttta   2279 gtctgtcagt tgaattcaga gcactgaaag gtgttaaatt ggggtatgtg gtttgattga   2339 taaaaagtta cctctcagta ttttgtgtca ctgagaagct ttacaatgga tgcttttgaa   2399 acaagtatca gcaaaggat tgttttcac tctggagga gagggtggag aaagcacttg    2459 ctttcatcct ctggcatcgg aaactcccct atgcacttga agatggttta aaagattaaa   2519 gaaacgatta agagaaaagg ttggaagctt tatactaaat gggctccttc atggtgacgc   2579 cccgtcaacc acaatcaaga actgaggcct gaggctggtt gtacaatgcc cacgcctgcc   2639 tggctgcttt cacctgggag tgctttcgat gtgggcacct gggcttccta gggctgcttc   2699 tgagtggttc tttcacgtgt tgtgtccata gctttagtct tcctaaataa gatccaccca   2759 cacctaagtc acagaatttc taagttcccc aactactctc acacccttt aaagataaag   2819 tatgttgtaa ccaggatgtc ttaaatgatt ctttgtgtac cttttctgtc atattcagaa   2879 accgttttgt gcctgctggg agtaattcct ttagcaatta agtatttggt agctgaataa   2939 ggggtcagaa cttctgaaac cagagatctg taatcatctc tattggcctg gggtgcctgt   2999 gctataaatg agtttcttca catgaaaaac acagccagcc caagatgact tatctgggtt   3059 taggattcaa tagtattcac taactgctta ttacatgagc aatttcatca aatctcccaaa  3119 ctcttaaagg atgctttcgg aaaacacgct gtataccttag atgatgacta aatgcaaaat  3179
```

```
ccttgggctt tggtttttt ctagtaagga ttttaaataa ctgccgactt caaaagtgtt    3239
cttaaaacga aagataatgt taagaaaaat ttgaaagctt tggaaaacca aatttgtaat    3299
atcattgtat ttttattaa aagtttgta ataaatttct aaattatctt ctgg           3353
```

<210> SEQ ID NO 60
<211> LENGTH: 400
<212> TYPE: PRT
<213> ORGANISM: Homo sapiens

<400> SEQUENCE: 60

```
Met Ala Ala Asn Tyr Ser Ser Thr Ser Thr Arg Arg Glu His Val Lys
1               5                  10                  15

Val Lys Thr Ser Ser Gln Pro Gly Phe Leu Glu Arg Leu Ser Glu Thr
            20                  25                  30

Ser Gly Gly Met Phe Val Gly Leu Met Ala Phe Leu Leu Ser Phe Tyr
        35                  40                  45

Leu Ile Phe Thr Asn Glu Gly Arg Ala Leu Lys Thr Ala Thr Ser Leu
    50                  55                  60

Ala Glu Gly Leu Ser Leu Val Val Ser Pro Asp Ser Ile His Ser Val
65                  70                  75                  80

Ala Pro Glu Asn Glu Gly Arg Leu Val His Ile Ile Gly Ala Leu Arg
                85                  90                  95

Thr Ser Lys Leu Leu Ser Asp Pro Asn Tyr Gly Val His Leu Pro Ala
            100                 105                 110

Val Lys Leu Arg Arg His Val Glu Met Tyr Gln Trp Val Glu Thr Glu
        115                 120                 125

Glu Ser Arg Glu Tyr Thr Glu Asp Gly Gln Val Lys Lys Glu Thr Arg
    130                 135                 140

Tyr Ser Tyr Asn Thr Glu Trp Arg Ser Glu Ile Ile Asn Ser Lys Asn
145                 150                 155                 160

Phe Asp Arg Glu Ile Gly His Lys Asn Pro Ser Ala Met Ala Val Glu
                165                 170                 175

Ser Phe Met Ala Thr Ala Pro Phe Val Gln Ile Gly Arg Phe Phe Leu
            180                 185                 190

Ser Ser Gly Leu Ile Asp Lys Val Asp Asn Phe Lys Ser Leu Ser Leu
        195                 200                 205

Ser Lys Leu Glu Asp Pro His Val Asp Ile Ile Arg Arg Gly Asp Phe
    210                 215                 220

Phe Tyr His Ser Glu Asn Pro Lys Tyr Pro Glu Val Gly Asp Leu Arg
225                 230                 235                 240

Val Ser Phe Ser Tyr Ala Gly Leu Ser Gly Asp Asp Pro Asp Leu Gly
                245                 250                 255

Pro Ala His Val Val Thr Val Ile Ala Arg Gln Arg Gly Asp Gln Leu
            260                 265                 270

Val Pro Phe Ser Thr Lys Ser Gly Asp Thr Leu Leu Leu His His
        275                 280                 285

Gly Asp Phe Ser Ala Glu Glu Val Phe His Arg Glu Leu Arg Ser Asn
    290                 295                 300

Ser Met Lys Thr Trp Gly Leu Arg Ala Ala Gly Trp Met Ala Met Phe
305                 310                 315                 320

Met Gly Leu Asn Leu Met Thr Arg Ile Leu Tyr Thr Leu Val Asp Trp
                325                 330                 335

Phe Pro Val Phe Arg Asp Leu Val Asn Ile Gly Leu Lys Ala Phe Ala
```

```
                  340            345             350
Phe Cys Val Ala Thr Ser Leu Thr Leu Leu Thr Val Ala Ala Gly Trp
            355               360              365

Leu Phe Tyr Arg Pro Leu Trp Ala Leu Leu Ile Ala Gly Leu Ala Leu
        370               375              380

Val Pro Ile Leu Val Ala Arg Thr Arg Val Pro Ala Lys Lys Leu Glu
385               390              395              400

<210> SEQ ID NO 61
<211> LENGTH: 2163
<212> TYPE: DNA
<213> ORGANISM: Homo sapiens
<220> FEATURE:
<221> NAME/KEY: misc_feature
<223> OTHER INFORMATION: H3C1779.4
<220> FEATURE:
<221> NAME/KEY: CDS
<222> LOCATION: (260)..(1459)

<400> SEQUENCE: 61
aaagctttgc agtgcgcagg cgcatcaatg aggtactgca atgtcccgga ccgtatagtt    60
tccaggacgt ctcgccgcgc gcatgcgcag aaacactggg cacaggggga ggtaactgca   120
gtaagtcccg cttggccctg gagtccacgc ggattttcga agctggggct ggcaagaggc   180
cgctggacac cacgctccag tcgtcagccc acttcctagc tgaacagcgc gaggcggcgg   240
cagcgagccg gtcccacc atg gcc gcg aat tat tcc agt acc agt acc cgg    292
                   Met Ala Ala Asn Tyr Ser Ser Thr Ser Thr Arg
                    1               5                  10 aga gaa cat gtc aaa gtt aaa acc agc tcc cag cca ggc ttc ctg gaa    340
Arg Glu His Val Lys Val Lys Thr Ser Ser Gln Pro Gly Phe Leu Glu
            15                  20                  25 cgg ctg agc gag acc tcg ggt ggg atg ttt gtg ggg ctc atg gcc ttc    388
Arg Leu Ser Glu Thr Ser Gly Gly Met Phe Val Gly Leu Met Ala Phe
        30                  35                  40 ctc ctc tcc ttc tac cta att ttc acc aat gag ggc cgc gca ttg aag    436
Leu Leu Ser Phe Tyr Leu Ile Phe Thr Asn Glu Gly Arg Ala Leu Lys
    45                  50                  55 acg gca acc tca ttg gct gag ggg ctc tcg ctt gtg gtg tct ccc gac    484
Thr Ala Thr Ser Leu Ala Glu Gly Leu Ser Leu Val Val Ser Pro Asp
60                  65                  70                  75 agc atc cac agt gtg gct ccg gag aat gaa gga agg ctg gtg cac atc    532
Ser Ile His Ser Val Ala Pro Glu Asn Glu Gly Arg Leu Val His Ile
                80                  85                  90 att ggc gcc tta cgg aca tcc aag ctt ttg tct gat cca aac tat ggg    580
Ile Gly Ala Leu Arg Thr Ser Lys Leu Leu Ser Asp Pro Asn Tyr Gly
            95                 100                 105 gtc cat ctt ccg gct gtg aaa ctg cgg agg cac gtg gag atg tac caa    628
Val His Leu Pro Ala Val Lys Leu Arg Arg His Val Glu Met Tyr Gln
        110                 115                 120 tgg gta gaa act gag gag tcc agg gag tac acc gag gat ggg cag gtg    676
Trp Val Glu Thr Glu Glu Ser Arg Glu Tyr Thr Glu Asp Gly Gln Val
    125                 130                 135 aag aag gag acg agg tat tcc tac aac act gaa tgg agg tca gaa atc    724
Lys Lys Glu Thr Arg Tyr Ser Tyr Asn Thr Glu Trp Arg Ser Glu Ile
140                 145                 150                 155 atc aac agc aaa aac ttc gac cga gag att ggc cac aaa aac ccc agt    772
Ile Asn Ser Lys Asn Phe Asp Arg Glu Ile Gly His Lys Asn Pro Ser
                160                 165                 170 gcc atg gca gtg gag tca ttc atg gca aca gcc ccc ttt gtc caa att    820
Ala Met Ala Val Glu Ser Phe Met Ala Thr Ala Pro Phe Val Gln Ile
```

-continued

```
                     175                 180                 185
ggc agg ttt ttc ctc tcg tca ggc ctc atc gac aaa gtc gac aac ttc       868
Gly Arg Phe Phe Leu Ser Ser Gly Leu Ile Asp Lys Val Asp Asn Phe
        190                 195                 200 aag tcc ctg agc cta tcc aag ctg gag gac cct cat gtg gac atc att       916
Lys Ser Leu Ser Leu Ser Lys Leu Glu Asp Pro His Val Asp Ile Ile
205                 210                 215 cgc cgt gga gac ttt ttc tac cac agc gaa aat ccc aag tat cca gag       964
Arg Arg Gly Asp Phe Phe Tyr His Ser Glu Asn Pro Lys Tyr Pro Glu
220                 225                 230                 235 gtg gga gac ttg cgt gtc tcc ttt tcc tat gct gga ctg agc ggc gat      1012
Val Gly Asp Leu Arg Val Ser Phe Ser Tyr Ala Gly Leu Ser Gly Asp
        240                 245                 250 gac cct gac ctg ggc cca gct cac gtg gtc act gtg att gcc cgg cag      1060
Asp Pro Asp Leu Gly Pro Ala His Val Val Thr Val Ile Ala Arg Gln
        255                 260                 265 cgg ggt gac cag cta gtc cca ttc tcc acc aag tct ggg gat acc tta      1108
Arg Gly Asp Gln Leu Val Pro Phe Ser Thr Lys Ser Gly Asp Thr Leu
        270                 275                 280 ctg ctc ctg cac cac ggg gac ttc tca gca gag gag gtg ttt cat aga      1156
Leu Leu Leu His His Gly Asp Phe Ser Ala Glu Glu Val Phe His Arg
285                 290                 295 gaa cta agg agc aac tcc atg aag acc tgg ggc ctg cgg gca gct ggc      1204
Glu Leu Arg Ser Asn Ser Met Lys Thr Trp Gly Leu Arg Ala Ala Gly
300                 305                 310                 315 tgg atg gcc atg ttc atg ggc ctc aac ctt atg aca cgg atc ctc tac      1252
Trp Met Ala Met Phe Met Gly Leu Asn Leu Met Thr Arg Ile Leu Tyr
        320                 325                 330 acc ttg gtg gac tgg ttt cct gtt ttc cga gac ctg gtc aac att ggc      1300
Thr Leu Val Asp Trp Phe Pro Val Phe Arg Asp Leu Val Asn Ile Gly
        335                 340                 345 ctg aaa gcc ttt gcc ttc tgt gtg gcc acc tcg ctg acc ctg ctg acc      1348
Leu Lys Ala Phe Ala Phe Cys Val Ala Thr Ser Leu Thr Leu Leu Thr
        350                 355                 360 gtg gcg gct ggc tgg ctc ttc tac cga ccc ctg tgg gcc ctc ctc att      1396
Val Ala Ala Gly Trp Leu Phe Tyr Arg Pro Leu Trp Ala Leu Leu Ile
365                 370                 375 gcc ggc ctg gcc ctt gtg ccc atc ctt gtt gct cgg aca cgg gtg cca      1444
Ala Gly Leu Ala Leu Val Pro Ile Leu Val Ala Arg Thr Arg Val Pro
380                 385                 390                 395 gcc aaa aag ttg gag tgaaaagacc ctggcacccg cccgacacct gggcttccta     1499
Ala Lys Lys Leu Glu
            400 gggctgcttc tgagtggttc tttcacgtgt tgtgtccata gctttagtct tcctaaataa   1559 gatccaccca cacctaagtc acagaatttc taagttcccc aactactctc acacccttt   1619 aaagataaag tatgttgtaa ccaggatgtc ttaaatgatt cttttgtgtac cttttctgtc  1679 atattcagaa accgttttgt gcctgctggg agtaattcct ttagcaatta agtatttggt   1739 agctgaataa ggggtcagaa cttctgaaac cagagatctg taatcatctc tattggcctg   1799 gggtgcctgt gctataaatg agtttcttca catgaaaaac acagccagcc caagatgact   1859 tatctgggtt taggattcaa tagtattcac taactgctta ttacatgagc aatttcatca   1919 aatctccaaa ctcttaaagg atgctttcgg aaaacacgct gtatacctag atgatgacta   1979 aatgcaaaat ccttgggctt tggttttttt ctagtaagga ttttaaataa ctgccgactt   2039 caaaagtgtt cttaaaacga aagataatgt taagaaaaat ttgaaagctt tggaaaacca   2099 aatttgtaat atcattgtat tttttattaa aagttttgta ataaatttct aaattatctt   2159
```

```
ctgg                                                                            2163
```

<210> SEQ ID NO 62
<211> LENGTH: 400
<212> TYPE: PRT
<213> ORGANISM: Homo sapiens

<400> SEQUENCE: 62

```
Met Ala Ala Asn Tyr Ser Ser Thr Ser Thr Arg Arg Glu His Val Lys
1               5                   10                  15

Val Lys Thr Ser Ser Gln Pro Gly Phe Leu Glu Arg Leu Ser Glu Thr
            20                  25                  30

Ser Gly Gly Met Phe Val Gly Leu Met Ala Phe Leu Leu Ser Phe Tyr
        35                  40                  45

Leu Ile Phe Thr Asn Glu Gly Arg Ala Leu Lys Thr Ala Thr Ser Leu
    50                  55                  60

Ala Glu Gly Leu Ser Leu Val Val Ser Pro Asp Ser Ile His Ser Val
65                  70                  75                  80

Ala Pro Glu Asn Glu Gly Arg Leu Val His Ile Ile Gly Ala Leu Arg
                85                  90                  95

Thr Ser Lys Leu Leu Ser Asp Pro Asn Tyr Gly Val His Leu Pro Ala
            100                 105                 110

Val Lys Leu Arg Arg His Val Glu Met Tyr Gln Trp Val Glu Thr Glu
        115                 120                 125

Glu Ser Arg Glu Tyr Thr Glu Asp Gly Gln Val Lys Lys Glu Thr Arg
    130                 135                 140

Tyr Ser Tyr Asn Thr Glu Trp Arg Ser Glu Ile Ile Asn Ser Lys Asn
145                 150                 155                 160

Phe Asp Arg Glu Ile Gly His Lys Asn Pro Ser Ala Met Ala Val Glu
                165                 170                 175

Ser Phe Met Ala Thr Ala Pro Phe Val Gln Ile Gly Arg Phe Phe Leu
            180                 185                 190

Ser Ser Gly Leu Ile Asp Lys Val Asp Asn Phe Lys Ser Leu Ser Leu
        195                 200                 205

Ser Lys Leu Glu Asp Pro His Val Asp Ile Ile Arg Arg Gly Asp Phe
    210                 215                 220

Phe Tyr His Ser Glu Asn Pro Lys Tyr Pro Glu Val Gly Asp Leu Arg
225                 230                 235                 240

Val Ser Phe Ser Tyr Ala Gly Leu Ser Gly Asp Asp Pro Asp Leu Gly
                245                 250                 255

Pro Ala His Val Val Thr Val Ile Ala Arg Gln Arg Gly Asp Gln Leu
            260                 265                 270

Val Pro Phe Ser Thr Lys Ser Gly Asp Thr Leu Leu Leu His His
    275                 280                 285

Gly Asp Phe Ser Ala Glu Glu Val Phe His Arg Glu Leu Arg Ser Asn
290                 295                 300

Ser Met Lys Thr Trp Gly Leu Arg Ala Ala Gly Trp Met Ala Met Phe
305                 310                 315                 320

Met Gly Leu Asn Leu Met Thr Arg Ile Leu Tyr Thr Leu Val Asp Trp
                325                 330                 335

Phe Pro Val Phe Arg Asp Leu Val Asn Ile Gly Leu Lys Ala Phe Ala
            340                 345                 350

Phe Cys Val Ala Thr Ser Leu Thr Leu Leu Thr Val Ala Ala Gly Trp
        355                 360                 365
```

```
Leu Phe Tyr Arg Pro Leu Trp Ala Leu Leu Ile Ala Gly Leu Ala Leu
    370                 375                 380

Val Pro Ile Leu Val Ala Arg Thr Arg Val Pro Ala Lys Lys Leu Glu
385                 390                 395                 400

<210> SEQ ID NO 63
<211> LENGTH: 482
<212> TYPE: DNA
<213> ORGANISM: Homo sapiens
<220> FEATURE:
<221> NAME/KEY: misc_feature
<223> OTHER INFORMATION: H3C1779.5
<220> FEATURE:
<221> NAME/KEY: CDS
<222> LOCATION: (178)..(375)

<400> SEQUENCE: 63
atgcgcagaa acactgggca caggggagg taactgcagt aagtcccgct tggccctgga      60
gtccacgcgg attttcgaag ctggggctgg caagaggccg ctggacacca cgctccagtc    120
gtcagcccac ttcctagctg aacagcgcga ggcggcggca gcgagccggg tcccacc       177 atg gcc gcg aat cca aaa cct gga agc tgt caa gat acc cat cca ctg      225
Met Ala Ala Asn Pro Lys Pro Gly Ser Cys Gln Asp Thr His Pro Leu
1               5                   10                  15 acg aat gat tca gca cac tgt ggt ata gtc ata aat gga ata cta ctc      273
Thr Asn Asp Ser Ala His Cys Gly Ile Val Ile Asn Gly Ile Leu Leu
            20                  25                  30 agc cat gaa aag gaa caa att cct gat aaa cac cac aac atg aat gaa      321
Ser His Glu Lys Glu Gln Ile Pro Asp Lys His His Asn Met Asn Glu
        35                  40                  45 ttg caa aag cag tgc tct gag tcc aag aag ctg ggc aga aag gag ttg      369
Leu Gln Lys Gln Cys Ser Glu Ser Lys Lys Leu Gly Arg Lys Glu Leu
    50                  55                  60 gtg ccc tgattccatt tttctcaagt tgtagaagaa acaaactaat ctacgtattc       425
Val Pro
65 cagtaccagt acccggagag aacatgtcaa agttaaaacc agctcccagc caggctt        482

<210> SEQ ID NO 64
<211> LENGTH: 66
<212> TYPE: PRT
<213> ORGANISM: Homo sapiens

<400> SEQUENCE: 64

Met Ala Ala Asn Pro Lys Pro Gly Ser Cys Gln Asp Thr His Pro Leu
1               5                   10                  15

Thr Asn Asp Ser Ala His Cys Gly Ile Val Ile Asn Gly Ile Leu Leu
            20                  25                  30

Ser His Glu Lys Glu Gln Ile Pro Asp Lys His His Asn Met Asn Glu
        35                  40                  45

Leu Gln Lys Gln Cys Ser Glu Ser Lys Lys Leu Gly Arg Lys Glu Leu
    50                  55                  60

Val Pro
65

<210> SEQ ID NO 65
<211> LENGTH: 699
<212> TYPE: DNA
<213> ORGANISM: Homo sapiens
<220> FEATURE:
<221> NAME/KEY: misc_feature
```

<223> OTHER INFORMATION: H3C1779.6
<220> FEATURE:
<221> NAME/KEY: CDS
<222> LOCATION: (178)..(369)

<400> SEQUENCE: 65

| | |
|---|---|
| atgcgcagaa acactgggca caggggagg taactgcagt aagtcccgct tggccctgga | 60 |
| gtccacgcgg atttttcgaag ctggggctgg caagaggccg ctggacacca cgctccagtc | 120 |
| gtcagcccac ttcctagctg aacagcgcga ggcggcggca gcgagccggg tcccacc | 177 |

| atg gcc gcg aat tat tcc agt acc agt acc cgg aga gaa cat gtc aaa | 225 |
|---|---|
| Met Ala Ala Asn Tyr Ser Ser Thr Ser Thr Arg Arg Glu His Val Lys | |
| 1               5                   10                  15 | |

| gtt aaa acc agc tcc cag cca ggc ttc ctg gaa cgg ctg agc gag acc | 273 |
|---|---|
| Val Lys Thr Ser Ser Gln Pro Gly Phe Leu Glu Arg Leu Ser Glu Thr | |
|             20                  25                  30 | |

| tcg ggt ggg atg ttt gtg ggg ctc atg gcc ttc ctg ctc tcc ttc tac | 321 |
|---|---|
| Ser Gly Gly Met Phe Val Gly Leu Met Ala Phe Leu Leu Ser Phe Tyr | |
|         35                  40                  45 | |

| cta att ttc acc aat gag gta aaa tgt ctg ggg tct tcc tgt gca gag | 369 |
|---|---|
| Leu Ile Phe Thr Asn Glu Val Lys Cys Leu Gly Ser Ser Cys Ala Glu | |
|     50                  55                  60 | |

| | |
|---|---|
| tgagagtccc caccatgtca gagagcaaag gcgatgaacc cggaggctgg atttggtaat | 429 |
| caagggccta gattttaaaa agagaaagga ggatactgag ttaatcacag ttctttccat | 489 |
| tgtgatccat cccacagctg atgtgagcag gaaggggagt agatcagttc acacacctga | 549 |
| atatccaggg gttagcacct gcctcaggcg tagttggatc caggtgttca tgctgggtca | 609 |
| ccaggaatct ccatttcttc atcttttgcc tgttttctc tattatggtg tttttcttgg | 669 |
| gcaggcactt catctgtgat ggcaaatgtg | 699 |

<210> SEQ ID NO 66
<211> LENGTH: 64
<212> TYPE: PRT
<213> ORGANISM: Homo sapiens

<400> SEQUENCE: 66

Met Ala Ala Asn Tyr Ser Ser Thr Ser Thr Arg Arg Glu His Val Lys
1               5                   10                  15

Val Lys Thr Ser Ser Gln Pro Gly Phe Leu Glu Arg Leu Ser Glu Thr
            20                  25                  30

Ser Gly Gly Met Phe Val Gly Leu Met Ala Phe Leu Leu Ser Phe Tyr
        35                  40                  45

Leu Ile Phe Thr Asn Glu Val Lys Cys Leu Gly Ser Ser Cys Ala Glu
    50                  55                  60

<210> SEQ ID NO 67
<211> LENGTH: 1861
<212> TYPE: DNA
<213> ORGANISM: Homo sapiens
<220> FEATURE:
<221> NAME/KEY: misc_feature
<223> OTHER INFORMATION: H3C1779.7
<220> FEATURE:
<221> NAME/KEY: CDS
<222> LOCATION: (178)..(474)

<400> SEQUENCE: 67

| | |
|---|---|
| atgcgcagaa acactgggca caggggagg taactgcagt aagtcccgct tggccctgga | 60 |
| gtccacgcgg atttttcgaag ctggggctgg caagaggccg ctggacacca cgctccagtc | 120 |

```
gtcagcccac ttcctagctg aacagcgcga ggcggcggca gcgagccggg tcccacc          177 atg gcc gcg aat tat tcc agt acc agt acc cgg aga gaa cat gtc aaa        225
Met Ala Ala Asn Tyr Ser Ser Thr Ser Thr Arg Arg Glu His Val Lys
1               5                   10                  15 gtt aaa acc agc tcc cag cca ggc ttc ctg gaa cgg ctg agc gag acc        273
Val Lys Thr Ser Ser Gln Pro Gly Phe Leu Glu Arg Leu Ser Glu Thr
            20                  25                  30 tcg ggt ggg atg ttt gtg ggg ctc atg gcc ttc ctg ctc tcc ttc tac        321
Ser Gly Gly Met Phe Val Gly Leu Met Ala Phe Leu Leu Ser Phe Tyr
        35                  40                  45 cta att ttc acc aat gag ggc cgc gca ttg aag acg gca acc tca ttg        369
Leu Ile Phe Thr Asn Glu Gly Arg Ala Leu Lys Thr Ala Thr Ser Leu
    50                  55                  60 gct gag ggg ctc ttc tac cga ccc ctg tgg gcc ctc ctc att gcc ggc        417
Ala Glu Gly Leu Phe Tyr Arg Pro Leu Trp Ala Leu Leu Ile Ala Gly
65              70                  75                  80 ctg gcc ctt gtg ccc atc ctt gtt gct cgg aca cgg gtg cca gcc aaa        465
Leu Ala Leu Val Pro Ile Leu Val Ala Arg Thr Arg Val Pro Ala Lys
                85                  90                  95 aag ttg gag tgaaaagacc ctggcacccg cccgacacct gcgtgagccc                514
Lys Leu Glu taggatccag gtcctctctc acctctgacc cagctccatg ccagagcagg agccccggtc      574
aattttggac tctgcactcc ctctcctctt caggggccag acttggcagc atgtgcacca      634
ggttggtgtt caccagctca tgtcttcccc acatctcttc ttgccagtaa gcagctttgg      694
tgggcagcag cagctcatga atggcaagct gacagcttct cctgctgttt ccttcctctc      754
ttggactgag tgggtacggc cagccactca gcccattggc agctgacaac gcagacacgc      814
tctacggagg cctgctgata aagggctcag ccttgccgtg tgctgcttct catcactgca      874
cacaagtgcc atgctttgcc accaccacca agcacatctg tgatcctgaa gggcggccgt      934
tagtcattac tgctgagtcc tgggtcacca gcagacacac tgggcatgga cccctcaaag      994
caggcacacc caaaacacaa gtctgtggct agaacctgat gtggtgttta aaagagaaga     1054
aacactgaag atgtcctgag gagaaaagct ggacatatac tgggcttcac acttatctta     1114
tggcttggca gaatctttgt agtgtgtggg atctctgaag gccctattta agttttttctt    1174 cgttactttg ctgcttcatg tgtactttcc taccccaaga ggaagttttc tgaaataaga     1234
tttaaaaaca aaacaaaaaa aacacttaat atttcagact gttacaggaa acacccttta     1294
gtctgtcagt tgaattcaga gcactgaaag gtgttaaatt ggggtatgtg gtttgattga     1354
taaaaagtta cctctcagta ttttgtgtca ctgagaagct ttacaatgga tgcttttgaa     1414
acaagtatca gcaaaaggat ttgttttcac tctgggagga gagggtggag aaagcacttg     1474
ctttcatcct ctggcatcgg aaactcccct atgcacttga agatggttta aaagattaaa     1534
gaaacgatta agagaaaagg ttggaagctt tatactaaat gggctccttc atggtgacgc     1594
cccgtcaacc acaatcaaga actgaggcct gaggctggtt gtacaatgcc cacgcctgcc     1654
tggctgcttt cacctgggag tgctttcgat gtgggcacct gggcttccta gggctgcttc     1714
tgagtggttc tttcacgtgt tgtgtccata gctttagtct tcctaaataa gatccaccca     1774
cacctaagtc acagaatttc taagttcccc aactactctc acacccttt aaagataaag     1834 tatgttgtaa ccaggatgtc ttaaatg                                          1861

<210> SEQ ID NO 68
<211> LENGTH: 99
<212> TYPE: PRT
```

<213> ORGANISM: Homo sapiens

<400> SEQUENCE: 68

```
Met Ala Ala Asn Tyr Ser Ser Thr Ser Thr Arg Arg Glu His Val Lys
1               5                   10                  15

Val Lys Thr Ser Ser Gln Pro Gly Phe Leu Glu Arg Leu Ser Glu Thr
            20                  25                  30

Ser Gly Gly Met Phe Val Gly Leu Met Ala Phe Leu Leu Ser Phe Tyr
        35                  40                  45

Leu Ile Phe Thr Asn Glu Gly Arg Ala Leu Lys Thr Ala Thr Ser Leu
    50                  55                  60

Ala Glu Gly Leu Phe Tyr Arg Pro Leu Trp Ala Leu Leu Ile Ala Gly
65                  70                  75                  80

Leu Ala Leu Val Pro Ile Leu Val Ala Arg Thr Arg Val Pro Ala Lys
                85                  90                  95

Lys Leu Glu
```

<210> SEQ ID NO 69
<211> LENGTH: 2368
<212> TYPE: DNA
<213> ORGANISM: Homo sapiens
<220> FEATURE:
<221> NAME/KEY: misc_feature
<223> OTHER INFORMATION: H3C1779.8
<220> FEATURE:
<221> NAME/KEY: CDS
<222> LOCATION: (178)..(474)

<400> SEQUENCE: 69

```
atgcgcagaa acactgggca caggggagg taactgcagt aagtcccgct tggccctgga      60
gtccacgcgg attttcgaag ctggggctgg caagaggccg ctggacacca cgctccagtc    120
gtcagcccac ttcctagctg aacagcgcga ggcggcggca gcgagccggg tcccacc       177 atg gcc gcg aat tat tcc agt acc agt acc cgg aga gaa cat gtc aaa     225
Met Ala Ala Asn Tyr Ser Ser Thr Ser Thr Arg Arg Glu His Val Lys
1               5                   10                  15 gtt aaa acc agc tcc cag cca ggc ttc ctg gaa cgg ctg agc gag acc     273
Val Lys Thr Ser Ser Gln Pro Gly Phe Leu Glu Arg Leu Ser Glu Thr
            20                  25                  30 tcg ggt ggg atg ttt gtg ggg ctc atg gcc ttc ctg ctc tcc ttc tac     321
Ser Gly Gly Met Phe Val Gly Leu Met Ala Phe Leu Leu Ser Phe Tyr
        35                  40                  45 cta att ttc acc aat gag ggc cgc gca ttg aag acg gca acc tca ttg     369
Leu Ile Phe Thr Asn Glu Gly Arg Ala Leu Lys Thr Ala Thr Ser Leu
    50                  55                  60 gct gag ggg ctc ttc tac cga ccc ctg tgg gcc ctc ctc att gcc ggc     417
Ala Glu Gly Leu Phe Tyr Arg Pro Leu Trp Ala Leu Leu Ile Ala Gly
65                  70                  75                  80 ctg gcc ctt gtg ccc atc ctt gtt gct cgg aca cgg gtg cca gcc aaa     465
Leu Ala Leu Val Pro Ile Leu Val Ala Arg Thr Arg Val Pro Ala Lys
                85                  90                  95 aag ttg gag tgaaaagacc ctggcacccg cccgacacct gcgtgagccc             514
Lys Leu Glu taggatccag gtcctctctc acctctgacc cagctccatg ccagagcagg agccccggtc    574
aattttggac tctgcactcc ctctcctctt caggggccag acttggcagc atgtgcacca    634
ggttggtgtt caccagctca tgtcttcccc acatctcttc ttgccagtaa gcagctttgg    694
tgggcagcag cagctcatga atggcaagct gacagcttct cctgctgttt ccttcctctc    754
```

| | |
|---|---|
| ttggactgag tgggtacggc cagccactca gcccattggc agctgacaac gcagacacgc | 814 |
| tctacggagg cctgctgata aagggctcag ccttgccgtg tgctgcttct catcactgca | 874 |
| cacaagtgcc atgctttgcc accaccacca agcacatctg tgatcctgaa gggcggccgt | 934 |
| tagtcattac tgctgagtcc tgggtcacca gcagacacac tgggcatgga cccctcaaag | 994 |
| caggcacacc caaaacacaa gtctgtggct agaacctgat gtggtgttta aagagaaga | 1054 |
| aacactgaag atgtcctgag gagaaaagct ggacatatac tggcttcac acttatctta | 1114 |
| tggcttggca gaatctttgt agtgtgtggg atctctgaag ccctattta gttttttctt | 1174 |
| cgttactttg ctgcttcatg tgtactttcc tacccaaga ggaagttttc tgaaataaga | 1234 |
| tttaaaaaca aacaaaaaa aacacttaat atttcagact gttacaggaa acacccttta | 1294 |
| gtctgtcagt tgaattcaga gcactgaaag gtgttaaatt ggggtatgtg gtttgattga | 1354 |
| taaaaagtta cctctcagta ttttgtgtca ctgagaagct ttacaatgga tgcttttgaa | 1414 |
| acaagtatca gcaaaaggat ttgttttcac tctgggagga gagggtggag aaagcacttg | 1474 |
| ctttcatcct ctggcatcgg aaactcccct atgcacttga agatggttta aaagattaaa | 1534 |
| gaaacgatta agagaaaagg ttggaagctt tatactaaat gggctccttc atggtgacgc | 1594 |
| cccgtcaacc acaatcaaga actgaggcct gaggctggtt gtacaatgcc cacgcctgcc | 1654 |
| tggctgcttt cacctgggag tgctttcgat gtgggcacct gggcttccta gggctgcttc | 1714 |
| tgagtggttc tttcacgtgt tgtgtccata gctttagtct tcctaaataa gatccaccca | 1774 |
| cacctaagtc acagaatttc taagttcccc aactactctc acacccttt aaagataaag | 1834 |
| tatgttgtaa ccaggatgtc ttaaatgatt ctttgtgtac cttttctgtc atattcagaa | 1894 |
| accgttttgt gcctgctggg agtaattcct ttagcaatta agtatttggt agctgaataa | 1954 |
| ggggtcagaa cttctgaaac cagagatctg taatcatctc tattggcctg gggtgcctgt | 2014 |
| gctataaatg agtttcttca catgaaaaac acagccagcc caagatgact tatctgggtt | 2074 |
| taggattcaa tagtattcac taactgctta ttacatgagc aatttcatca aatctccaaa | 2134 |
| ctcttaaagg atgctttcgg aaaacacgct gtatacctag atgatgacta aatgcaaaat | 2194 |
| ccttgggctt tggtttttt ctagtaagga ttttaaataa ctgccgactt caaaagtgtt | 2254 |
| cttaaaacga aagataatgt taagaaaaat ttgaaagctt tggaaaacca aatttgtaat | 2314 |
| atcattgtat ttttattaa aagttttgta ataaatttct aaattatctt ctgg | 2368 |

<210> SEQ ID NO 70
<211> LENGTH: 99
<212> TYPE: PRT
<213> ORGANISM: Homo sapiens

<400> SEQUENCE: 70

```
Met Ala Ala Asn Tyr Ser Ser Thr Ser Thr Arg Arg Glu His Val Lys
1               5                   10                  15

Val Lys Thr Ser Ser Gln Pro Gly Phe Leu Glu Arg Leu Ser Glu Thr
            20                  25                  30

Ser Gly Gly Met Phe Val Gly Leu Met Ala Phe Leu Leu Ser Phe Tyr
        35                  40                  45

Leu Ile Phe Thr Asn Glu Gly Arg Ala Leu Lys Thr Ala Thr Ser Leu
    50                  55                  60

Ala Glu Gly Leu Phe Tyr Arg Pro Leu Trp Ala Leu Leu Ile Ala Gly
65                  70                  75                  80

Leu Ala Leu Val Pro Ile Leu Val Ala Arg Thr Arg Val Pro Ala Lys
                85                  90                  95
```

Lys Leu Glu

```
<210> SEQ ID NO 71
<211> LENGTH: 2718
<212> TYPE: DNA
<213> ORGANISM: Homo sapiens
<220> FEATURE:
<221> NAME/KEY: misc_feature
<223> OTHER INFORMATION: H3C1779.9
<220> FEATURE:
<221> NAME/KEY: CDS
<222> LOCATION: (1047)..(1331)

<400> SEQUENCE: 71
```

| | |
|---|---:|
| atgtaggaag ctggccaggc atgactgcag gcaatcgttg taggcagagc aaacccacgc | 60 |
| gcagatacac aggcgagagg cacttgacc tggactgggg acagcagcca gcagggtcag | 120 |
| ggcactggca gcagggtcgg tgtccggggg gtgtggcagg gctctggcag gtgactgtgt | 180 |
| ggagaacaca gagtgggtga tagaagcagg gccagtgagg ctcctgcggg cagacagtgg | 240 |
| taagagactc gggaatatgt ggcctggact ggatggggtg gtaggggagg agcgagccat | 300 |
| gtctttccca tagatgtgag tgggtgggtg gtgtgccat gtgctgagat ggagaaggcg | 360 |
| ccagtgtcag cactagacag gctgagatgt caagtggaaa tgtcaaggag gtggtggagg | 420 |
| tggtgggagc tgcagggctg tgaggcccgg gagagggcca gagctgcagc tttaaattgg | 480 |
| agggtcacgg catgtggagg ccaaggaagc agatgggatg tccggggaga gagtatggac | 540 |
| tgaagcagct aaagaattgc agcatctaat ggacaggaag aggggcagcg acagcgatgg | 600 |
| agcctgagaa ggagggtgca gtgtccccaa gccatgtgga gaggttctga gattaaacag | 660 |
| atcacacaca tagcgcagag catgctgccc agcagacatc ctccaacctg ctcaggggtg | 720 |
| gtgggcaggg tcctgctcat tccaggtgag accgtgggct gagggctcca ggtgctggca | 780 |
| ggctctgagc tgaggaaggc ccgtacgttc cacagagatc tcatgccttg ccctgtgctc | 840 |
| tgccagatgg gcagaaggac ttagcccctat aggaggcttg cccccactcc gtctggcctg | 900 |
| ttcagaaatg gccaacagct cccgagttgg tacagccccc tcaggacctg ccctgccgac | 960 |
| tgggtacgcc actggccctc agcatcctga cctgccccca ccttgtcctg caggaggtgt | 1020 |

| | | | | | | | | | |
|---|---|---|---|---|---|---|---|---|---:|
| ttcatagaga actaaggagc aactcc atg aag acc tgg ggc ctg cgg gca gct | | | | | | | | | 1073 |
| | | | | Met Lys Thr Trp Gly Leu Arg Ala Ala | | | | | |
| | | | | 1 | 5 | | | | |

| | | | | | | | | | | | | | | | | |
|---|---|---|---|---|---|---|---|---|---|---|---|---|---|---|---|---:|
| ggc | tgg | atg | gcc | atg | ttc | atg | ggc | ctc | aac | ctt | atg | aca | cgg | atc | ctc | 1121 |
| Gly | Trp | Met | Ala | Met | Phe | Met | Gly | Leu | Asn | Leu | Met | Thr | Arg | Ile | Leu | |
| 10 | | | | 15 | | | | 20 | | | | 25 | | | | |

| | | | | | | | | | | | | | | | | |
|---|---|---|---|---|---|---|---|---|---|---|---|---|---|---|---|---:|
| tac | acc | ttg | gtg | gac | tgg | ttt | cct | gtt | ttc | cga | gac | ctg | gtc | aac | att | 1169 |
| Tyr | Thr | Leu | Val | Asp | Trp | Phe | Pro | Val | Phe | Arg | Asp | Leu | Val | Asn | Ile | |
| | | | | 30 | | | | 35 | | | | 40 | | | | |

| | | | | | | | | | | | | | | | | |
|---|---|---|---|---|---|---|---|---|---|---|---|---|---|---|---|---:|
| ggc | ctg | aaa | gcc | ttt | gcc | ttc | tgt | gtg | gcc | acc | tcg | ctg | acc | ctg | ctg | 1217 |
| Gly | Leu | Lys | Ala | Phe | Ala | Phe | Cys | Val | Ala | Thr | Ser | Leu | Thr | Leu | Leu | |
| | | 45 | | | | 50 | | | | 55 | | | | | | |

| | | | | | | | | | | | | | | | | |
|---|---|---|---|---|---|---|---|---|---|---|---|---|---|---|---|---:|
| acc | gtg | gcg | gct | ggc | tgg | ctc | ttc | tac | cga | ccc | ctg | tgg | gcc | ctc | ctc | 1265 |
| Thr | Val | Ala | Ala | Gly | Trp | Leu | Phe | Tyr | Arg | Pro | Leu | Trp | Ala | Leu | Leu | |
| | | | 60 | | | | 65 | | | | 70 | | | | | |

| | | | | | | | | | | | | | | | | |
|---|---|---|---|---|---|---|---|---|---|---|---|---|---|---|---|---:|
| att | gcc | ggc | ctg | gcc | ctt | gtg | ccc | atc | ctt | gtt | gct | cgg | aca | cgg | gtg | 1313 |
| Ile | Ala | Gly | Leu | Ala | Leu | Val | Pro | Ile | Leu | Val | Ala | Arg | Thr | Arg | Val | |
| | | 75 | | | | 80 | | | | 85 | | | | | | |

| | | | | | | |
|---|---|---|---|---|---|---:|
| cca | gcc | aaa | aag | ttg | gag | tgaaaagacc ctggcacccg cccgacacct | 1361 |
| Pro | Ala | Lys | Lys | Leu | Glu | |
| 90 | | | | 95 | | |

```
gcgtgagccc taggatccag gtcctctctc acctctgacc cagctccatg ccagagcagg    1421
agccccggtc aattttggac tctgcactcc ctctcctctt caggggccag acttggcagc    1481
atgtgcacca ggttggtgtt caccagctca tgtcttcccc acatctcttc ttgccagtaa    1541
gcagctttgg tgggcagcag cagctcatga atggcaagct gacagcttct cctgctgttt    1601
ccttcctctc ttggactgag tgggtacggc cagccactca gcccattggc agctgacaac    1661
gcagacacgc tctacggagg cctgctgata aagggctcag ccttgccgtg tgctgcttct    1721
catcactgca cacaagtgcc atgctttgcc accaccacca agcacatctg tgatcctgaa    1781
gggcggccgt tagtcattac tgctgagtcc tgggtcacca gcagacacac tgggcatgga    1841
cccctcaaag caggcacacc caaaacacaa gtctgtggct agaacctgat gtggtgttta    1901
aaagagaaga aacactgaag atgtcctgag gagaaaagct ggacatatac tgggcttcac    1961
acttatctta tggcttggca gaatctttgt agtgtgtggg atctctgaag gccctattta    2021 agttttctt cgttactttg ctgcttcatg tgtactttcc tacccaaga ggaagttttc    2081 tgaaataaga tttaaaaaca aaacaaaaaa aacacttaat atttcagact gttacaggaa    2141
acacccttta gtctgtcagt tgaattcaga gcactgaaag gtgttaaatt ggggtatgtg    2201
gtttgattga taaaaagtta cctctcagta ttttgtgtca ctgagaagct ttacaatgga    2261
tgcttttgaa acaagtatca gcaaaaggat ttgttttcac tctgggagga gagggtggag    2321
aaagcacttg ctttcatcct ctggcatcgg aaactcccct atgcacttga agatggttta    2381
aaagattaaa gaaacgatta agagaaaagg ttggaagctt tatactaaat gggctccttc    2441
atggtgacgc cccgtcaacc acaatcaaga actgaggcct gaggctggtt gtacaatgcc    2501
cacgcctgcc tggctgcttt cacctgggag tgctttcgat gtgggcacct gggcttccta    2561
gggctgcttc tgagtggttc tttcacgtgt tgtgtccata gctttagtct tcctaaaataa    2621 gatccaccca cacctaagtc acagaatttc taagttcccc aactactctc acacccttt    2681 aaagataaag tatgttgtaa ccaggatgtc ttaaatg                              2718
```

<210> SEQ ID NO 72
<211> LENGTH: 95
<212> TYPE: PRT
<213> ORGANISM: Homo sapiens

<400> SEQUENCE: 72

Met Lys Thr Trp Gly Leu Arg Ala Ala Gly Trp Met Ala Met Phe Met
1               5                   10                  15

Gly Leu Asn Leu Met Thr Arg Ile Leu Tyr Thr Leu Val Asp Trp Phe
            20                  25                  30

Pro Val Phe Arg Asp Leu Val Asn Ile Gly Leu Lys Ala Phe Ala Phe
        35                  40                  45

Cys Val Ala Thr Ser Leu Thr Leu Leu Thr Val Ala Ala Gly Trp Leu
    50                  55                  60

Phe Tyr Arg Pro Leu Trp Ala Leu Leu Ile Ala Gly Leu Ala Leu Val
65                  70                  75                  80

Pro Ile Leu Val Ala Arg Thr Arg Val Pro Ala Lys Lys Leu Glu
                85                  90                  95

<210> SEQ ID NO 73
<211> LENGTH: 2718
<212> TYPE: DNA
<213> ORGANISM: Homo sapiens
<220> FEATURE:
<221> NAME/KEY: misc_feature
<223> OTHER INFORMATION: H3C1779.10
<220> FEATURE:
<221> NAME/KEY: CDS
<222> LOCATION: (1047)..(1331)

<400> SEQUENCE: 73

| | |
|---|---:|
| atgtaggaag ctggccaggc atgactgcag gcaatcgttg taggcagagc aaacccacgc | 60 |
| gcagatacac aggcgagagg acacttgacc tggactgggg acagcagcca gcagggtcag | 120 |
| ggcactggca gcagggtcgg tgtccggggg gtgtggcagg gctctggcag gtgactgtgt | 180 |
| ggagaacaca gagtgggtga tagaagcagg gccagtgagg ctcctgcggg cagacagtgg | 240 |
| taagagactc gggaatatgt ggcctggact ggatggggtg gtaggggagg agcgagccat | 300 |
| gtctttccca tagatgtgag tgggtgggtg gtgtgccat gtgctgagat ggagaaggcg | 360 |
| ccagtgtcag cactagacag gctgagatgt caagtggaaa tgtcaaggag gtggtggagg | 420 |
| tggtgggagc tgcagggctg tgaggcccgg gagagggcca gagctgcagc tttaaattgg | 480 |
| agggtcacgg catgtggagg ccaaggaagc agatgggatg tccggggaga gagtatggac | 540 |
| tgaagcagct aaagaattgc agcatctaat ggacaggaag aggggcagcg acagcgatgg | 600 |
| agcctgagaa ggagggtgca gtgtccccaa gccatgtgga gaggttctga gattaaacag | 660 |
| atcacacaca tagcgcagag catgctgccc agcagacatc ctccaacctg ctcagggggtg | 720 |
| gtgggcaggg tcctgctcat tccaggtgag accgtgggct gagggctcca ggtgctggca | 780 |
| ggctctgagc tgaggaaggc ccgtacgttc cacagagatc tcatgccttg ccctgtgctc | 840 |
| tgccagatgg gcagaaggac ttagccctat aggaggcttg cccccactcc gtctggcctg | 900 |
| ttcagaaatg gccaacagct cccgagttgg tacagccccc tcaggacctg ccctgccgac | 960 |
| tgggtacgcc actggccctc agcatcctga cctgccccca ccttgtcctg caggaggtgt | 1020 |
| ttcatagaga actaaggagc aactcc atg aag acc tgg ggc ctg cgg gca gct<br>                                                  Met Lys Thr Trp Gly Leu Arg Ala Ala<br>                                                  1               5 | 1073 |
| ggc tgg atg gcc atg ttc atg ggc ctc aac ctt atg aca cgg atc ctc<br>Gly Trp Met Ala Met Phe Met Gly Leu Asn Leu Met Thr Arg Ile Leu<br>10               15                   20                    25 | 1121 |
| tac acc ttg gtg gac tgg ttt cct gtt ttc cga gac ctg gtc aac att<br>Tyr Thr Leu Val Asp Trp Phe Pro Val Phe Arg Asp Leu Val Asn Ile<br>                     30                          35                          40 | 1169 |
| ggc ctg aaa gcc ttt gcc ttc tgt gtg gcc acc tcg ctg acc ctg ctg<br>Gly Leu Lys Ala Phe Ala Phe Cys Val Ala Thr Ser Leu Thr Leu Leu<br>                         45                          50                          55 | 1217 |
| acc gtg gcg gct ggc tgg ctc ttc tac cga ccc ctg tgg gcc ctc ctc<br>Thr Val Ala Ala Gly Trp Leu Phe Tyr Arg Pro Leu Trp Ala Leu Leu<br>                 60                          65                          70 | 1265 |
| att gcc ggc ctg gcc ctt gtg ccc atc ctt gtt gct cgg aca cgg gtg<br>Ile Ala Gly Leu Ala Leu Val Pro Ile Leu Val Ala Arg Thr Arg Val<br>75               80                   85 | 1313 |
| cca gcc aaa aag ttg gag tgaaaagacc ctggcacccg cccgacacct<br>Pro Ala Lys Lys Leu Glu<br>90               95 | 1361 |
| gcgtgagccc taggatccag gtcctctctc acctctgacc cagctccatg ccagagcagg | 1421 |
| agccccggtc aattttggac tctgcactcc ctctcctctt caggggccag acttggcagc | 1481 |
| atgtgcacca ggttggtgtt caccagctca tgtcttcccc acatctcttc ttgccagtaa | 1541 |
| gcagctttgg tgggcagcag cagctcatga atggcaagct gacagcttct cctgctgttt | 1601 |
| ccttcctctc ttggactgag tgggtacggc cagccactca gcccattggc agctgacaac | 1661 |

```
gcagacacgc tctacggagg cctgctgata aagggctcag ccttgccgtg tgctgcttct    1721
catcactgca cacaagtgcc atgctttgcc accaccacca agcacatctg tgatcctgaa    1781
gggcggccgt tagtcattac tgctgagtcc tgggtcacca gcagacacac tgggcatgga    1841
cccctcaaag caggcacacc caaaacacaa gtctgtggct agaacctgat gtggtgttta    1901
aaagagaaga aacactgaag atgtcctgag gagaaaagct ggacatatac tgggcttcac    1961
acttatctta tggcttggca gaatctttgt agtgtgtggg atctctgaag ccctatttta    2021 agttttctt cgttactttg ctgcttcatg tgtactttcc taccccaaga ggaagttttc     2081
tgaaataaga tttaaaaaca aaacaaaaaa aacacttaat atttcagact gttacaggaa    2141
acacccttta gtctgtcagt tgaattcaga gcactgaaag gtgttaaatt ggggtatgtg    2201
gtttgattga taaaaagtta cctctcagta ttttgtgtca ctgagaagct ttacaatgga    2261
tgcttttgaa acaagtatca gcaaaaggat ttgttttcac tctgggagga gagggtggag    2321
aaagcacttg ctttcatcct ctggcatcgg aaactcccct atgcacttga agatggttta    2381
aaagattaaa gaaacgatta agagaaaagg ttggaagctt tatactaaat gggctccttc    2441
atggtgacgc cccgtcaacc acaatcaaga actgaggcct gaggctggtt gtacaatgcc    2501
cacgcctgcc tggctgcttt cacctgggag tgctttcgat gtgggcacct gggcttccta    2561
gggctgcttc tgagtggttc tttcacgtgt tgtgtccata gctttagtct tcctaaataa    2621
gatccaccca cacctaagtc acagaatttc taagttcccc aactactctc acacccttt    2681 aaagataaag tatgttgtaa ccaggatgtc ttaaatg                             2718
```

<210> SEQ ID NO 74
<211> LENGTH: 95
<212> TYPE: PRT
<213> ORGANISM: Homo sapiens

<400> SEQUENCE: 74

Met Lys Thr Trp Gly Leu Arg Ala Ala Gly Trp Met Ala Met Phe Met
1               5                   10                  15

Gly Leu Asn Leu Met Thr Arg Ile Leu Tyr Thr Leu Val Asp Trp Phe
            20                  25                  30

Pro Val Phe Arg Asp Leu Val Asn Ile Gly Leu Lys Ala Phe Ala Phe
        35                  40                  45

Cys Val Ala Thr Ser Leu Thr Leu Leu Thr Val Ala Ala Gly Trp Leu
    50                  55                  60

Phe Tyr Arg Pro Leu Trp Ala Leu Leu Ile Ala Gly Leu Ala Leu Val
65                  70                  75                  80

Pro Ile Leu Val Ala Arg Thr Arg Val Pro Ala Lys Lys Leu Glu
                85                  90                  95

<210> SEQ ID NO 75
<211> LENGTH: 3225
<212> TYPE: DNA
<213> ORGANISM: Homo sapiens
<220> FEATURE:
<221> NAME/KEY: misc_feature
<223> OTHER INFORMATION: H3C1779.11
<220> FEATURE:
<221> NAME/KEY: CDS
<222> LOCATION: (1047)..(1331)

<400> SEQUENCE: 75

```
atgtaggaag ctggccaggc atgactgcag gcaatcgttg taggcagagc aaacccacgc      60
gcagatacac aggcgagagg acacttgacc tggactgggg acagcagcca gcagggtcag     120
```

```
ggcactggca gcagggtcgg tgtccggggg gtgtggcagg gctctggcag gtgactgtgt    180
ggagaacaca gagtgggtga tagaagcagg gccagtgagg ctcctgcggg cagacagtgg    240
taagagactc gggaatatgt ggcctggact ggatggggtg gtaggggagg agcgagccat    300
gtctttccca tagatgtgag tggtgggtg ggtgtgccat gtgctgagat ggagaaggcg     360
ccagtgtcag cactagacag gctgagatgt caagtggaaa tgtcaaggag gtggtggagg    420
tggtgggagc tgcagggctg tgaggcccgg gagagggcca gagctgcagc tttaaattgg    480
agggtcacgg catgtggagg ccaaggaagc agatgggatg tccggggaga gagtatggac    540
tgaagcagct aaagaattgc agcatctaat ggacaggaag aggggcagcg acagcgatgg    600
agcctgagaa ggagggtgca gtgtccccaa gccatgtgga gaggttctga gattaaacag    660
atcacacaca tagcgcagag catgctgccc agcagacatc ctccaacctg ctcaggggtg    720
gtgggcaggg tcctgctcat tccaggtgag accgtgggct gagggctcca ggtgctggca    780
ggctctgagc tgaggaaggc ccgtacgttc cacagagatc tcatgccttg ccctgtgctc    840
tgccagatgg gcagaaggac ttagccctat aggaggcttg ccccactcc gtctggcctg     900
ttcagaaatg gccaacagct cccgagttgg tacagccccc tcaggacctg ccctgccgac    960
tgggtacgcc actggccctc agcatcctga cctgccccca ccttgtcctg caggaggtgt   1020
ttcatagaga actaaggagc aactcc atg aag acc tgg ggc ctg cgg gca gct   1073
                               Met Lys Thr Trp Gly Leu Arg Ala Ala
                                1               5
ggc tgg atg gcc atg ttc atg ggc ctc aac ctt atg aca cgg atc ctc   1121
Gly Trp Met Ala Met Phe Met Gly Leu Asn Leu Met Thr Arg Ile Leu
 10              15                  20                  25
tac acc ttg gtg gac tgg ttt cct gtt ttc cga gac ctg gtc aac att   1169
Tyr Thr Leu Val Asp Trp Phe Pro Val Phe Arg Asp Leu Val Asn Ile
             30                  35                  40
ggc ctg aaa gcc ttt gcc ttc tgt gtg gcc acc tcg ctg acc ctg ctg   1217
Gly Leu Lys Ala Phe Ala Phe Cys Val Ala Thr Ser Leu Thr Leu Leu
         45                  50                  55
acc gtg gcg gct ggc tgg ctc ttc tac cga ccc ctg tgg gcc ctc ctc   1265
Thr Val Ala Ala Gly Trp Leu Phe Tyr Arg Pro Leu Trp Ala Leu Leu
     60                  65                  70
att gcc ggc ctg gcc ctt gtg ccc atc ctt gtt gct cgg aca cgg gtg   1313
Ile Ala Gly Leu Ala Leu Val Pro Ile Leu Val Ala Arg Thr Arg Val
 75                  80                  85
cca gcc aaa aag ttg gag tgaaaagacc ctggcacccg cccgacacct           1361
Pro Ala Lys Lys Leu Glu
 90              95
gcgtgagccc taggatccag gtcctctctc acctctgacc cagctccatg ccagagcagg   1421
agccccggtc aattttggac tctgcactcc ctctcctctt caggggccag acttggcagc   1481
atgtgcacca ggttggtgtt caccagctca tgtcttcccc acatctcttc ttgccagtaa   1541
gcagctttgg tgggcagcag cagctcatga atggcaagct gacagcttct cctgctgttt   1601
ccttcctctc ttggactgag tgggtacggc cagccactca gcccattggc agctgacaac   1661
gcagacacgc tctacggagg cctgctgata aagggctcag ccttgccgtg tgctgcttct   1721
catcactgca cacaagtgcc atgctttgcc accaccacca agcacatctg tgatcctgaa   1781
gggcggccgt tagtcattac tgctgagtcc tgggtcacca gcagacacac tgggcatgga   1841
cccctcaaag caggcacacc caaaacacaa gtctgtggct agaacctgat gtggtgttta   1901
aaagagaaga aacactgaag atgtcctgag gagaaaagct ggacatatac tgggcttcac   1961
```

```
acttatctta tggcttggca gaatctttgt agtgtgtggg atctctgaag gccctattta  2021
agtttttctt cgttactttg ctgcttcatg tgtactttcc tacccccaaga ggaagttttc  2081 tgaaataaga tttaaaaaca aaacaaaaaa aacacttaat atttcagact gttacaggaa  2141
acacccttta gtctgtcagt tgaattcaga gcactgaaag gtgttaaatt ggggtatgtg  2201
gtttgattga taaaaagtta cctctcagta ttttgtgtca ctgagaagct ttacaatgga  2261
tgcttttgaa acaagtatca gcaaaaggat ttgttttcac tctggggagga gagggtggag  2321 aaagcacttg ctttcatcct ctggcatcgg aaactcccct atgcacttga agatggttta  2381
aaagattaaa gaaacgatta agagaaaagg ttggaagctt tatactaaat gggctccttc  2441
atggtgacgc cccgtcaacc acaatcaaga actgaggcct gaggctggtt gtacaatgcc  2501
cacgcctgcc tggctgcttt cacctgggag tgctttcgat gtgggcacct gggcttccta  2561
gggctgcttc tgagtggttc tttcacgtgt tgtgtccata gctttagtct tcctaaataa  2621
gatccaccca cacctaagtc acagaatttc taagttcccc aactactctc acacccttt  2681 aaagataaag tatgttgtaa ccaggatgtc ttaaatgatt ctttgtgtac cttttctgtc  2741
atattcagaa accgttttgt gcctgctggg agtaattcct ttagcaatta agtatttggt  2801
agctgaataa ggggtcagaa cttctgaaac cagagatctg taatcatctc tattggcctg  2861
gggtgcctgt gctataaatg agtttcttca catgaaaaac acagccagcc caagatgact  2921
tatctgggtt taggattcaa tagtattcac taactgctta ttcatgagc aatttcatca  2981 aatctccaaa ctcttaaagg atgctttcgg aaaacacgct gtatacctag atgatgacta  3041
aatgcaaaat ccttgggctt tggttttttt ctagtaagga ttttaaataa ctgccgactt  3101
caaaagtgtt cttaaaacga aagataatgt taagaaaaat ttgaaagctt tggaaaacca  3161
aatttgtaat atcattgtat tttttattaa aagttttgta ataaatttct aaattatctt  3221
ctgg                                                               3225
```

<210> SEQ ID NO 76
<211> LENGTH: 95
<212> TYPE: PRT
<213> ORGANISM: Homo sapiens

<400> SEQUENCE: 76

```
Met Lys Thr Trp Gly Leu Arg Ala Ala Gly Trp Met Ala Met Phe Met
1               5                   10                  15

Gly Leu Asn Leu Met Thr Arg Ile Leu Tyr Thr Leu Val Asp Trp Phe
            20                  25                  30

Pro Val Phe Arg Asp Leu Val Asn Ile Gly Leu Lys Ala Phe Ala Phe
        35                  40                  45

Cys Val Ala Thr Ser Leu Thr Leu Leu Thr Val Ala Ala Gly Trp Leu
    50                  55                  60

Phe Tyr Arg Pro Leu Trp Ala Leu Leu Ile Ala Gly Leu Ala Leu Val
65                  70                  75                  80

Pro Ile Leu Val Ala Arg Thr Arg Val Pro Ala Lys Lys Leu Glu
                85                  90                  95
```

DIAGNOSTIC TEST FOR CARDIOMYOPATHY

RELATED APPLICATIONS

This application is a continuation of U.S. application Ser. No. 12/339,877, filed on Dec. 19, 2008, which claims the benefit under 35 USC §119 of U.S. provisional application Ser. No. 61/016,226 filed Dec. 21, 2007, all of which are incorporated herein by reference in their entirety.

INCORPORATION OF SEQUENCE LISTING

A computer readable form of the Sequence Listing "P2882U.S.02 Sequence Listing.txt" (129,405 bytes), submitted via EFS-WEB and created on Mar. 14, 2013, is herein incorporated by reference.

FIELD

The disclosure relates to methods and compositions for diagnosing and treating cardiomyopathy and particularly to methods and compositions for diagnosing and treating arrhythmogenic right ventricular dysplasia/cardiomyopathy (ARVD/C).

BACKGROUND

Arrhythmogenic right ventricular cardiomyopathy (ARVC) causes ventricular tachyarrhythmias, heart failure and sudden cardiac death (SCD), with fibro-fatty replacement of the ventricular myocardium. Diagnosis relies upon descriptive diagnostic criteria[1], and remains difficult because gene carriers manifest different phenotypes (variable expressivity) and may show no signs of disease (reduced penetrance). This recognized clinical heterogeneity[2] makes the potential use of genetic diagnosis (either by linkage or mutation analysis), to determine those at risk prior to malignant clinical sequalea, extremely important. ARVC is also genetically heterogeneous, with eleven ARVC mapped loci and seven identified genes to date,[3-7] several coding for desmosomal proteins (desmoplakin, plakophilin, desmoglein and plakoglobin) that are predicted to succumb to mechanical stress.[5, 7]

A novel locus for ARVC (ARVD5) was mapped to chromosome 3p in 1998 as the result of a genome-wide scan in an extended family from Newfoundland, Canada with an autosomal dominant form of ARVC.[8] Since then, 14 additional Newfoundland families have been identified where a disease-associated haplotype (ARVD5 haplotype) is shared with the family used to map the ARVD5 locus. This ARVD5 haplotype has been used to predict disease risk status, allowing prophylactic treatment with implantable cardioverter defibrillator (ICD) therapy that greatly improved survival.[9]

Identification of the ARVD5 gene would allow improved diagnosis and therapeutic treatment of individuals with ARVD/C.

SUMMARY

The inventors have identified a minimal critical region of the ARVD5 haplotype associated with the cardiomyopathy, ARVD/C and have further identified a gene, TMEM43, disease associated variants of which are diagnostic of ARVD/C. The inventors have found that various markers that map to the ARVD5 region are useful for predicting if an individual is affected when other family members are available for testing. These include microsatellite markers: D3S3610, D3S2403, D3S1516, D3S3608, D3S2385, D3S3602, D3S1585, D3S1554, D3S3595, D3S3613. In addition the inventors have shown that detection of TMEM43 disease associated variants is useful for diagnosing individuals with ARVD/C and for prognosing individuals at risk of developing ARVD/C. Early detection is advantageous as the inventors have previously shown that improved survival occurs in patients with an implantable cardioverter defibrillator (ICD). The inventors disclose that at risk families are readily screened for TMEM43 disease associated variants through, for example, genetic mutation analysis.

The inventors have further demonstrated that a serine to leucine substitution in amino acid 358 of TMEM43 at locus ARVD5 is the cause of ARVD/C in 15 families analyzed. Both arrhythmiogenic and cardiomyopathic disease occurs, leading to early death and heart failure, particularly in males. Pre-symptomatic diagnosis by molecular testing facilitates early recognition of subjects within the population at risk for sudden death, and allows for therapeutic intervention.

Accordingly, an aspect of the disclosure provides a method of screening for, diagnosing or detecting a risk of developing cardiomyopathy in a subject by detecting the presence of a transmembrane protein 43 (TMEM43) disease associated variant in a sample of the subject, where the presence of the TMEM43 disease associated variant is indicative that the subject has cardiomyopathy or an increased risk of developing cardiomyopathy compared to an individual not having the TMEM43 disease associated variant. In an embodiment, the cardiomyopathy is ARVD/C. In another embodiment, the cardiomyopathy is ARVD/C, associated with ARVD5.

Another aspect provides a method of screening for, diagnosing or detecting a risk of developing arrhythmogenic right ventricular dysplasia/cardiomyopathy (ARVD/C) in a subject by detecting the presence of a transmembrane protein 43 (TMEM43) disease associated variant in a sample of the subject, where the presence of the TMEM43 disease associated variant is indicative that the subject has ARVD/C or an increased risk of developing ARVD/C compared to an individual not having the TMEM43 disease associated variant.

A further aspect provides a method of identifying subjects with an increased risk of and/or predisposition for developing cardiomyopathy, by detecting the presence of a TMEM43 disease associated variant in a sample of the subject, where the presence of the TMEM43 disease associated is indicative that the subject has an increased risk of developing cardiomyopathy. In an embodiment, the cardiomyopathy is ARVD/C. In another embodiment, the cardiomyopathy is ARVD/C, associated with ARVD5.

In an embodiment the TMEM43 disease associated variant detected has a gene mutation.

A gene mutation is optionally detected in genomic sequence. Accordingly, in one embodiment the gene mutation is mutation of a nucleotide corresponding to genome position 14158166. In another embodiment the mutation is the nucleotide corresponding to genome position 14158166 and is a missense mutation. In another embodiment the missense mutation at this position is a mutation to thymidine (nucleotide 171, SEQ ID NO:4). In yet another embodiment the gene mutation is 14158166C>T.

A gene mutation is optionally detected in nucleic acid gene products. Accordingly, in one embodiment the gene mutation detected is mutation of a nucleotide corresponding to position 1073 in TMEM43 mRNA. In one embodiment the mutation of the nucleotide corresponding to position 1073 in TMEM43 mRNA is a missense mutation. In another embodiment the missense mutation at this position is mutation to thymidine (nucleotide 1222, SEQ ID NO:5). In a further embodiment the gene mutation is 1073C>T.

A gene mutation is optionally detected in polypeptide gene products. Accordingly, in one embodiment the gene mutation encodes a mutation of an amino acid corresponding to position 358 in TMEM43 polypeptide. In one embodiment the amino acid corresponding to position 358 is leucine (SEQ ID NO:6). In a further embodiment the gene mutation encodes S358L.

In alternate embodiments the gene mutation is a deletion mutation that results in deletion of: a nucleotide corresponding to genome position 14158166, a nucleotide corresponding to position 1073 in TMEM43 mRNA, or an amino acid corresponding to position 358 in TMEM43 polypeptide.

In certain embodiments the TMEM43 disease associated variant is detected in a sample of a subject where the sample contains blood. In other embodiments, the sample contains white blood cells. In yet other embodiments, the sample contains cardiac tissue.

The methods are useful for screening for, diagnosing or detecting a risk of developing ARVD/C in pre-symptomatic subjects and in subjects having a relative with an ARVD5 haplotype associated with ARVD/C.

In certain embodiments, the methods employ isolated nucleic acids and antibodies described herein. In other embodiments, the methods employ genotyping, PCR and RT-PCR, and/or use of microarrays.

Another aspect provides an isolated nucleic acid molecule comprising a nucleic acid sequence comprising a TMEM43 gene or transcript disease associated variant.

Another aspect provides a reagent for detecting a TMEM43 disease associated variant, such as an isolated nucleic acid primer or probe. In an embodiment, the isolated nucleic acid molecule comprises:
 a) any one of SEQ ID NOs: 1-54 and/or combinations thereof; and/or
 b) a nucleic acid molecule with at least 80%, 90%, 95%, or 99% sequence identity to a), characterized in that the nucleic acid molecule is capable of binding TMEM43 under moderately stringent conditions. In an embodiment, the nucleic acid with at least 80%, 90%, 95%, or 99% sequence identity to a) binds TMEM43 under moderately stringent conditions and is capable of priming strand synthesis. Isolated nucleic acid molecules including for example SEQ ID NOs: 1-52 are useful as primers to amplify TMEM43. In an embodiment, the isolated nucleic acid molecule is an amplified which is produced by amplification of a TMEM43 disease associated variant containing template. Isolated nucleic acid molecules including for example SEQ ID NO: 53 and/or 54, are useful for as probes to detect TMEM43 disease associated variants.

Another aspect provides a composition comprising at least one isolated nucleic acid sequence that hybridizes to:
 a) a RNA product of TMEM43;
 b) a nucleic acid complementary to a); and/or
 c) a nucleic acid corresponding to a);
where the composition is used to detect a TMEM43 disease associated variant. In an embodiment, a) comprises a TMEM43 disease associated variant. In an embodiment, a nucleic acid complementary to a) and/or corresponding to a) comprises genomic TMEM43. In certain embodiments, the isolated nucleic acid is a probe. In one embodiment the probe comprises SEQ ID NO: 53 or 54. In other embodiments the isolated nucleic acid is a primer optionally a primer pair useful for amplifying a TMEM43 disease associated variant. In certain embodiments the primers comprise SEQ ID NO:43 and/or SEQ ID NO:44.

The disclosure also describes kits containing one or more isolated nucleic acids and/or antibodies useful for detecting a TMEM43 disease associated variant and instructions for use.

A further aspect relates to a commercial package comprising one or more isolated nucleic acids and/or antibodies useful for detecting a TMEM43 disease associated variant and instructions for use.

Yet a further aspect relates to identifying TMEM43 disease associated variants comprising amplifying a TMEM43, gene or transcript or part thereof from a sample of a subject, comparing the amplified region to a control population, wherein a mutation that is detected in the sample and is rare or undetected in the control population is a TMEM43 disease associated variant.

Another aspect relates to a screening assay for identifying agents that target and/or bind a TMEM43 disease associated variant.

Other features and advantages of the disclosure will become apparent from the following detailed description. It should be understood, however, that the description and the specific examples while indicating preferred embodiments are given by way of illustration only, since various changes and modifications within the spirit and scope of the disclosure will become apparent to those skilled in the art from this description of various embodiments.

DRAWINGS

Embodiments are described below in relation to the drawings in which:

FIG. 1 is a schematic demonstrating that ARVC families are linked to 3p25. Panel A shows the pedigrees of 15 autosomal dominant ARVC families from Newfoundland linked to ARVD5 on 3p25. Patients diagnosed with ARVC are indicated by blackened squares (male) and circles (female). Panel B is the photomicrographs of paraffin-embedded post mortem right ventricular myocardium stained with masson trichrome showing fibrofatty replacement of myocytes where darker staining is the normal myocardium, lighter grey is fiber and white is fat, from a male teenager who had a SCD (left: ×40 magnification) and his second degree blood relative who also died suddenly in his 8th decade (right: ×20 magnification).

FIG. 2 is a schematic showing workflow and mutation status of subjects born at a priori 50% risk of ARVC.

FIG. 3 is a physical map of the ARVD5 critical region. Panel A shows a summary of recombinant ARVD5 haplotypes identified in patients across 15 ARVC families from Newfoundland. Eighteen microsatellite markers across the top, and summary family haplotypes on the side. Numbers in cells are alleles in base pairs. Panel B is the physical map of the ARVD5 critical region. Physical distances were captured from the March 2006 freeze of The UCSC Genome Browser. Arrows show the direction of transcription of each annotated gene in the ARVD5 critical region on chromosome 3p.

FIG. 4 is a comparison of TMEM43 cDNA in myocardium and leukocytes. (Panel A) Gene structure of TMEM43. (Panel B) Coverage of primers designed to amplify cDNA showing position of PCR primer pairs: Exons 1-4 (darkest grey), Exons 4-9 (light grey), Exons 9-12 (lighter grey); Exons 1-10 (medium grey) 5-12 (white). (Panel C) PCR products amplified from cDNA of EBV transfected B cells of affected subjects from the mutation screening panel (Affected AR1 & Affected AR15) and unaffected (control) subjects and cDNA of heart tissue from the left and right ventricle of an affected subject (Affected Left Ventricle and Affected Right Ventricle) and heart biopsy from a control subject. (Panel D&E) Sequencing traces of genomic and complimentary DNA including amino acid translations (top) and both forward and reverse traces (output from Mutation Surveyor) of an affected subject (Family AR13).

FIG. 5 is a haplotype analysis of the rare sequencing variants in ARVC families identified with key recombinations to the ARVD5 ancestral haplotype. Only one variant, TMEM43 1073 C>T, is retained on the ARVD5-ancestral haplotype (white) in subjects with primary affection status from families AR2 and AR10. Haplotypes consist of both microsatellite markers (D names) and the five rare variants (gene named followed by the variant description).

FIG. 6 is a schematic showing multiple alignment of the TMEM43 gene with eight other vertebrate and invertebrate homologous sequences Panel A: Large light grey box outlines the DUF1625 domain and black boxes outline predicted transmembrane domains. Completely conserved residues are in lightest grey, strongly similar residues are in gray and weakly similar residues are in dark grey. The mutation in ARVC families is shown highlighted in black. Panel B: shows the alignment of Eukaryotic species in Web logo format, where the third transmembrane domain is outlined (black box). The white arrow gives the position of the S358L mutation. Clustal W align was used to align orthologues from *Homo sapiens* (NP_077310)(SEQ ID NO:3), *Pan troglodytes* (XP_516299)(SEQ ID NO:7), *Canis familiaris* (XP_541751)(SEQ ID NO:8), *Mus musculus* (NP_083042)(SEQ ID NO:9), *Gallus gallus* (XP_414378)(SEQ ID NO:10), *Zenopus tropicalis* (UP10004D5297)(SEQ ID NO:11), *Tetraodon nigroviridis* (Q4RXL8)(SEQ ID NO:12), *Drosophila melanogaster* (NP_64162)(SEQ ID NO:13), *Rhizobium loti* (Q98HF3)(SEQ ID NO:14).[11]

FIG. 7 is a schematic showing the predicted topography of the TMEM43 protein showing four transmembrane domains (white) with predicted phoshorylation sites (pale grey), transactivation domain (medium grey), YingOYang sites (pale grey) SUMO attachment (dark grey), and the O-glycosylation sites (open grey), S358L mutation (black). The extracellular and cytoplasmic regions can switched for there is equal evidence supporting either orientation.

FIG. 8 is an analysis of clinical data in affected and non-affected individuals. A) Cumulative incidence of PVC's>1000 in 24 hours in: A1) Affected n=11 and unaffected n=18 males without >1000 PVC's at baseline. A2) Affected n=24 and unaffected n=21 females without >1000 PVC's at baseline. A3) Affected males vs. affected females without >1000 PVC's at baseline. B) Cumulative incidence of Heart Failure in: B1) Affected n=89 and unaffected n=71 males without heart failure at baseline. B2) Affected n=87 and unaffected n=68 females without heart failure at baseline. B3) Affected males vs. affected females without heart failure at baseline. C) Cumulative incidence of death in: C1) Affected n=148 and unaffected n=77 males. C2) Affected n=109 and unaffected 74=X females. C3) Affected males vs. affected females.

FIG. 9 is a schematic showing sequence variants identified through sequencing using the Mutation Screening Panel. All sequencing variants (n=240) identified in the 20 ARVD5 candidate genes. 19 variants were found exclusively in subjects with primary affection status.

FIG. 11 is schematic showing that clinically unaffected subjects from two ARVC families share distal regions of the ARVD5 ancestral haplotype that do not include the TMEM43 gene.

DESCRIPTION OF VARIOUS EMBODIMENTS

Figure 1A:
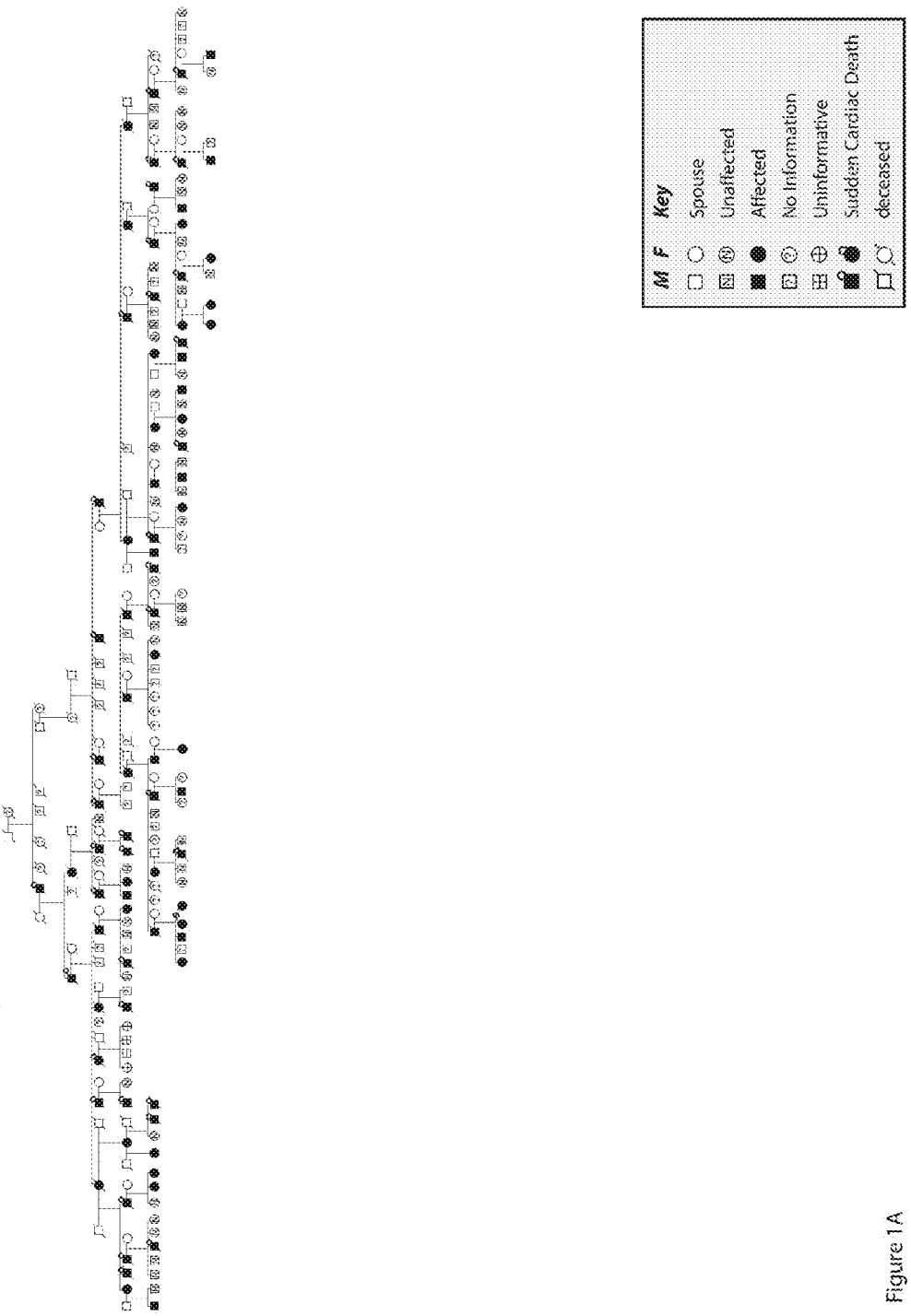
Figure 1A:
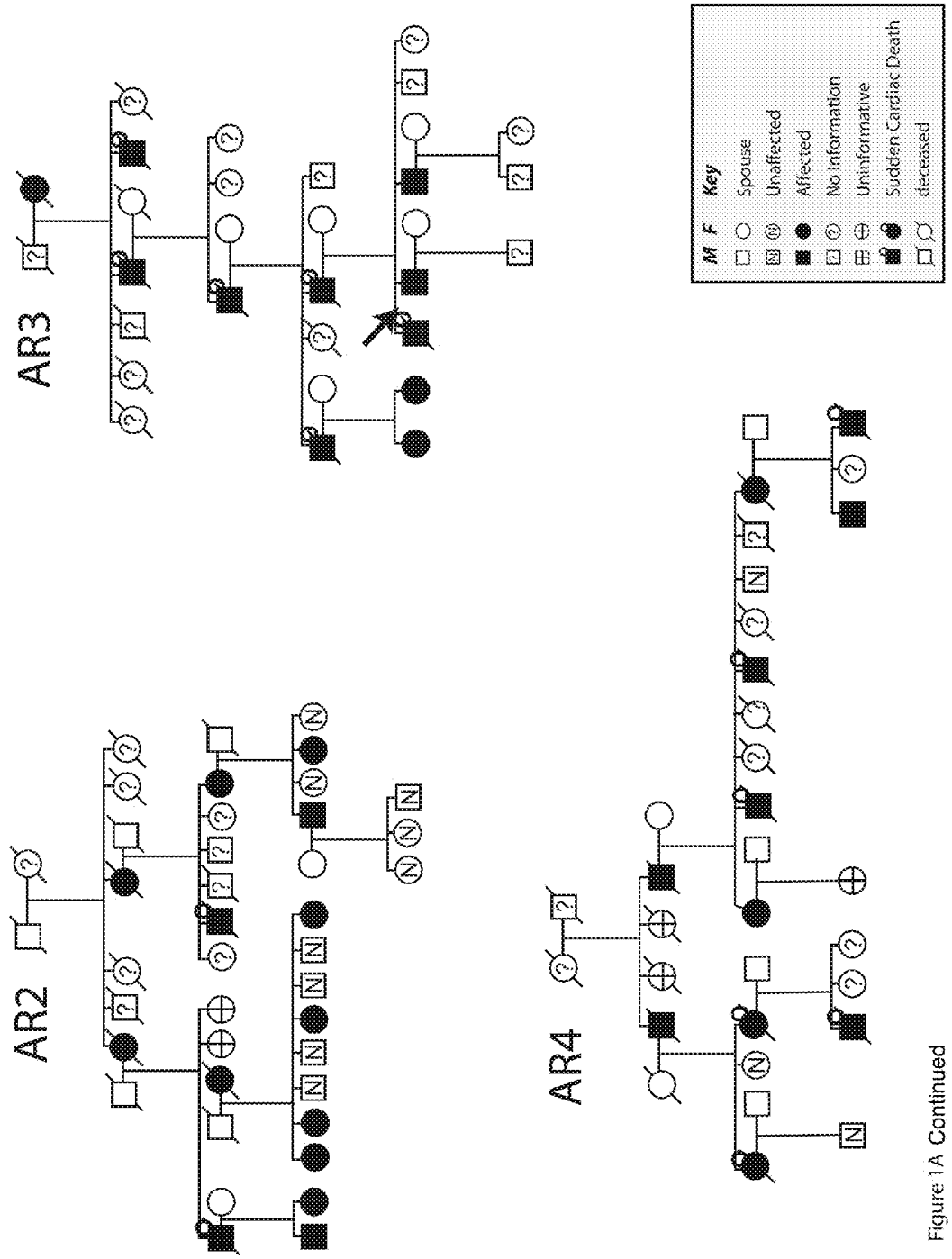
Figure 1A:
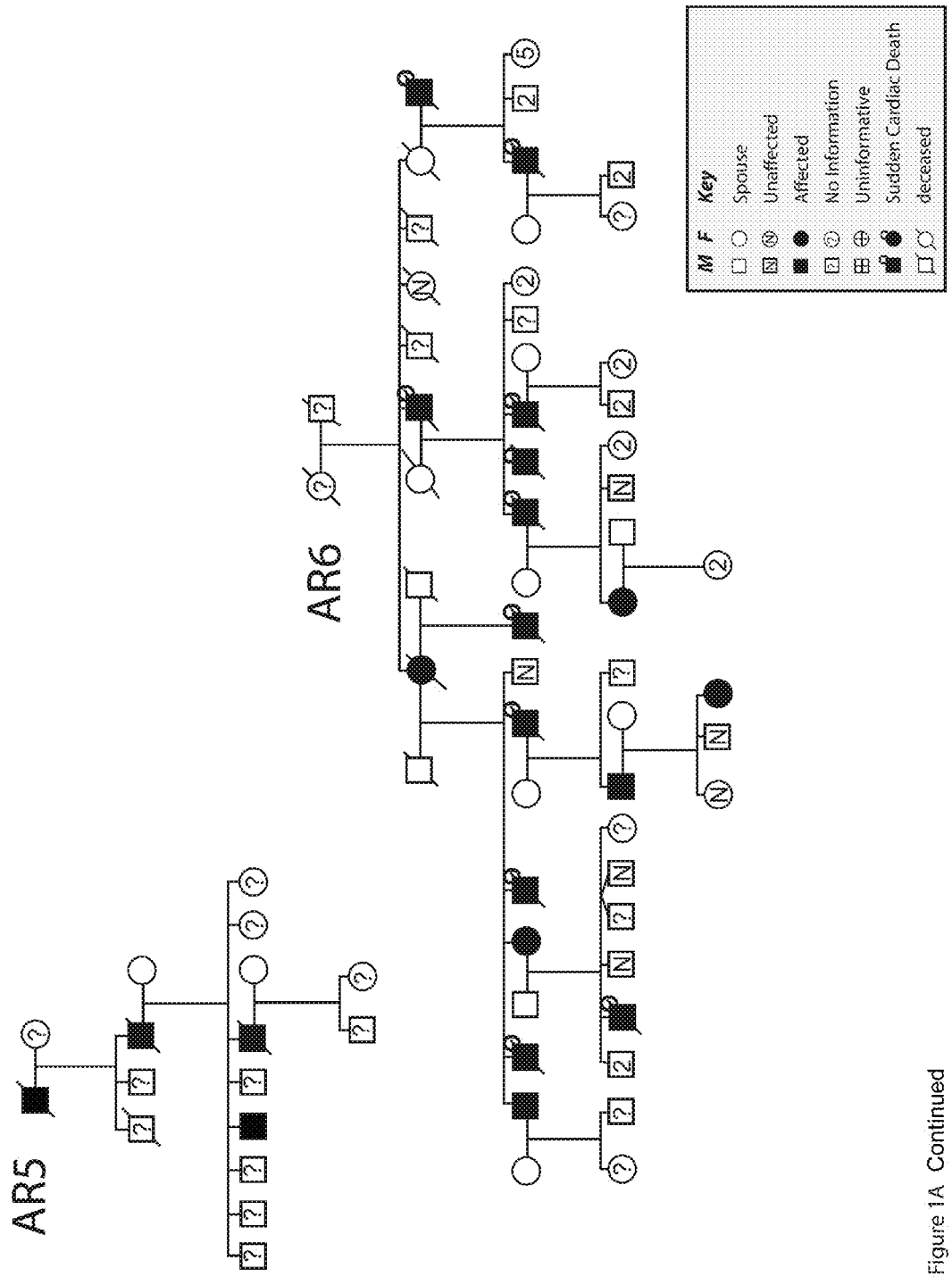
Figure 1A:
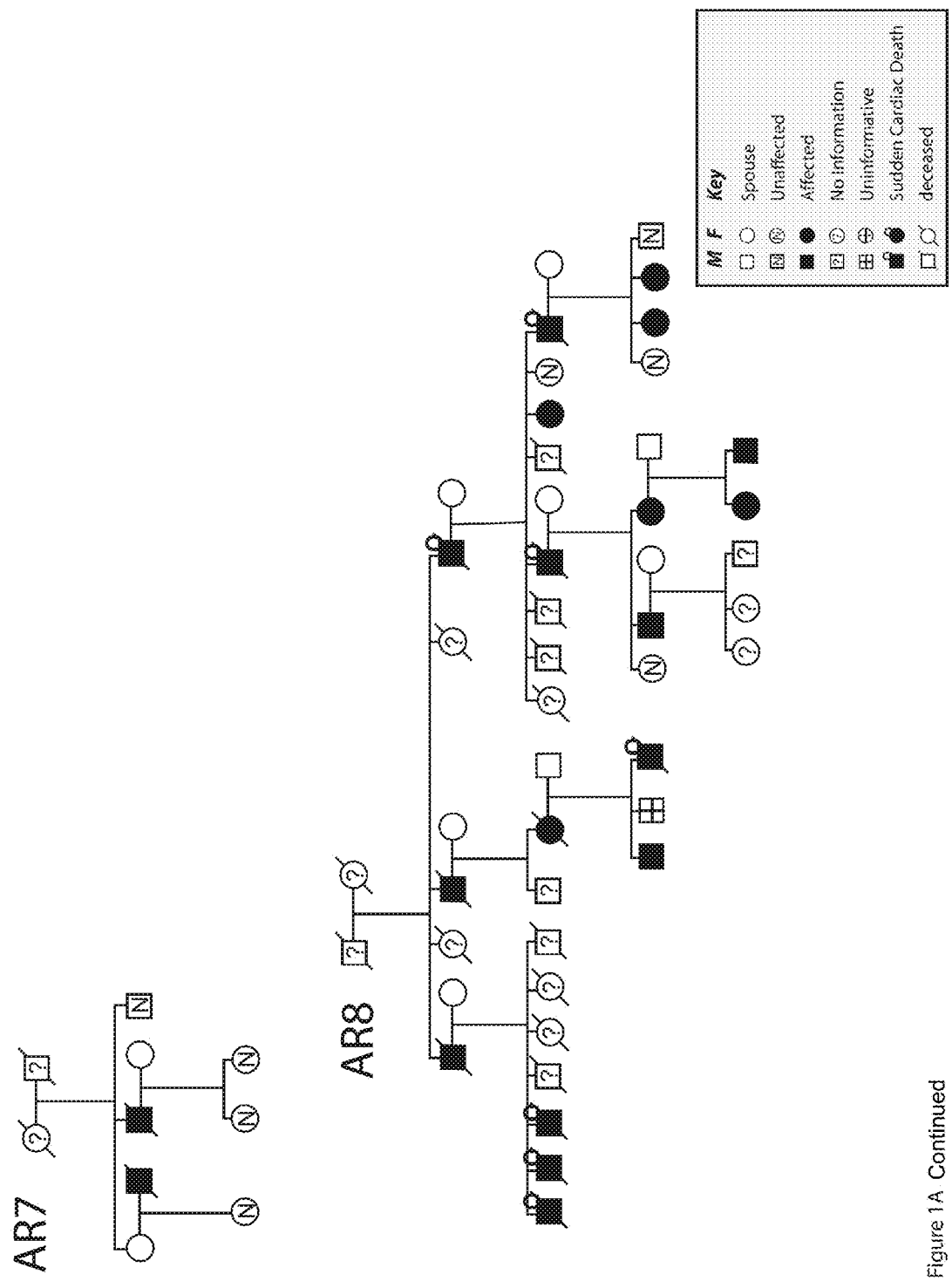
Figure 1A:
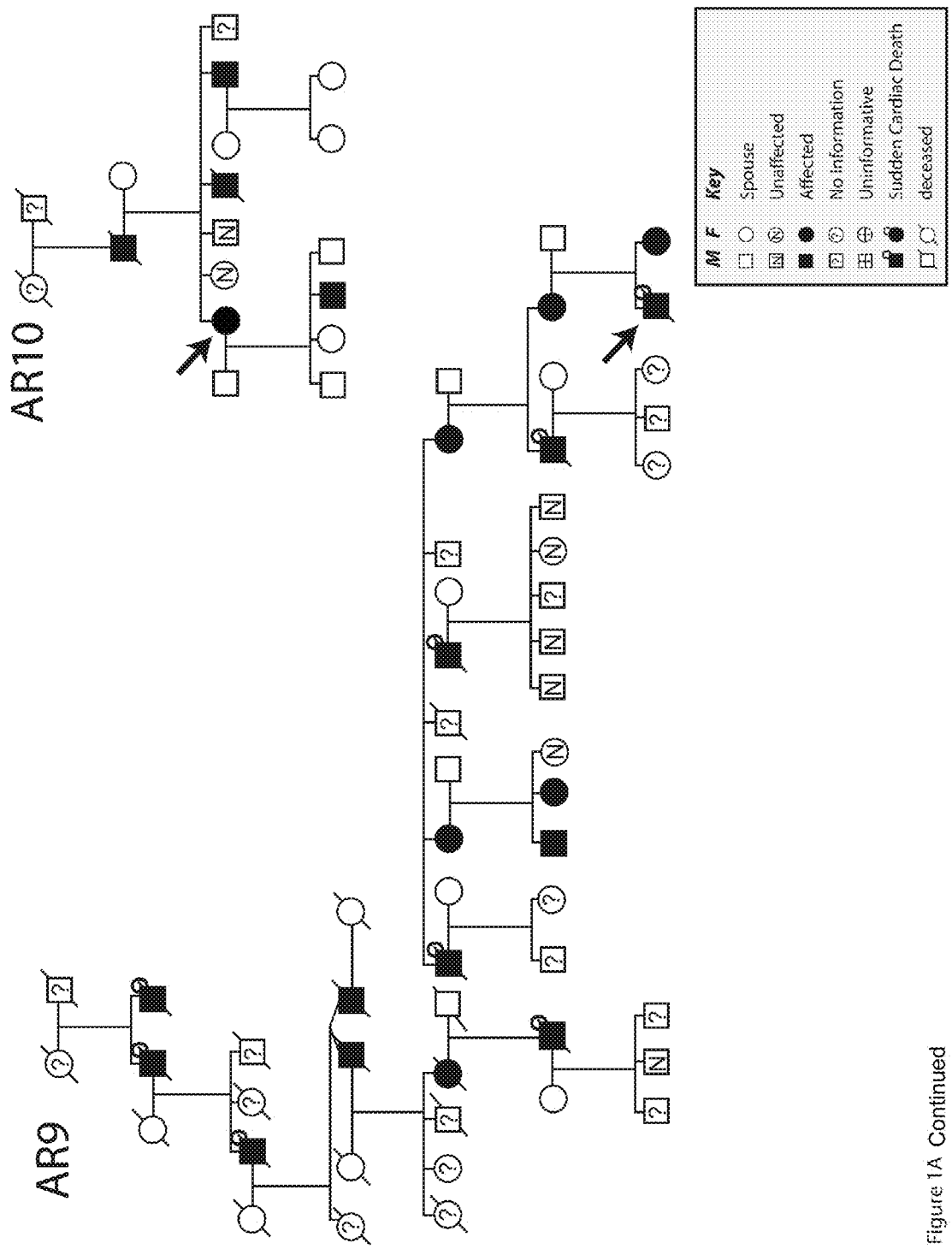
Figure 1A:
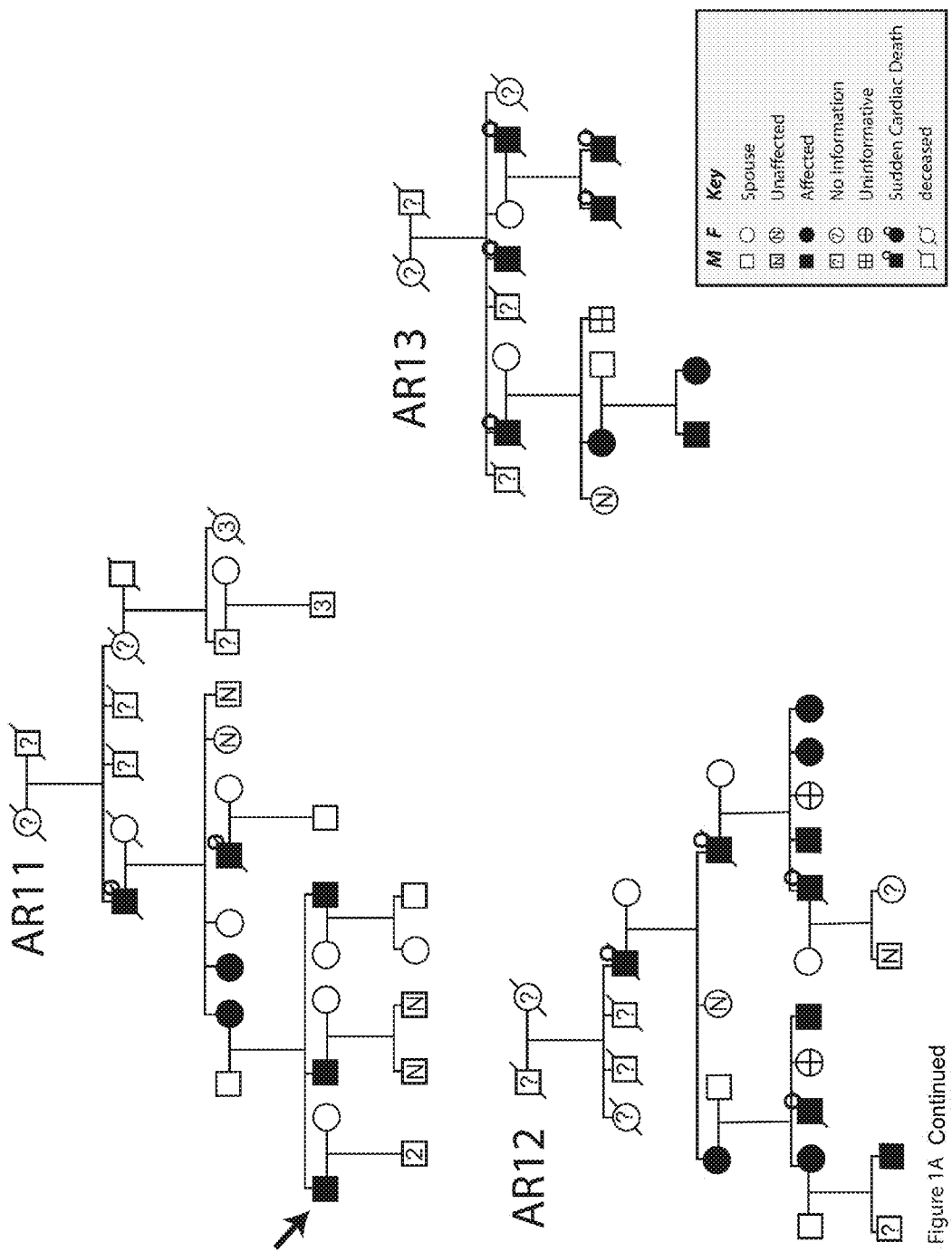
Figure 1A:
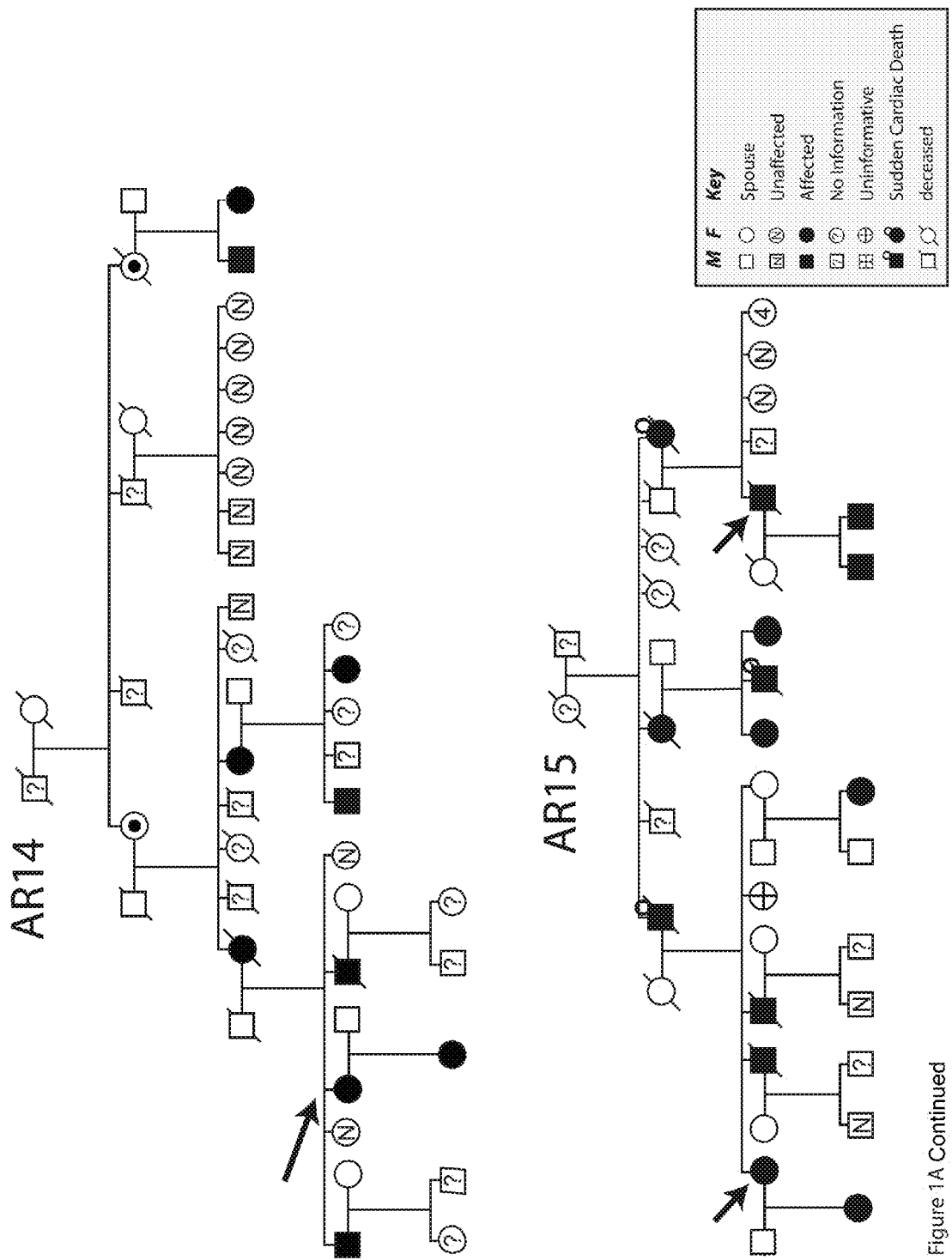

Arrhythmogenic right ventricular dysplasia/cardiomyopathy (ARVD/C) in its most severe presentation, causes sudden cardiac death and early death due to arrhythmias and heart failure. This is seen particularly in males. Clinical diagnosis of ARVD/C is difficult. Various loci including the ARVD5 locus have previously been identified. The inventors have identified a reduced minimal critical region of the ARVD5 haplotype associated with ARVD/C and have further identified a gene, TMEM43, disease associated variants of which are diagnostic of ARVD/C. For example a modification of serine to leucine at position 358 (S358L) was found in all affected individuals and in less than 1% of the population at large, indicating that detection of TMEM43 disease associated variants, such as S358L is diagnostic for ARVD/C and/or developing ARVD/C. At risk families are readily screened for TMEM43 disease associated variants through for example genetic mutation analysis. Detection of TMEM43 disease associated variants is useful for diagnosing individuals with ARVD/C and for prognosing individuals at risk of developing ARVD/C. Early detection is advantageous as the inventors have previously shown that improved survival occurs in patients with an implantable cardioverter defibrillator (ICD).

Accordingly, an aspect of the disclosure provides a method of screening for, diagnosing and/or detecting cardiomyopathy or an increased risk of developing cardiomyopathy in a subject comprising detecting the presence of a TMEM43 disease associated variant in a sample of the subject, wherein the presence of the TMEM43 disease associated variant is indicative of cardiomyopathy and/or an increased risk or developing cardiomyopathy.

Another embodiment provides a method of diagnosing ARVD/C comprising detecting the presence of a TMEM43 disease associated variant in a sample of the subject, wherein the presence of the TMEM43 disease associated variant is indicative of ARVD/C. In an embodiment, the subject has at least one clinical feature associated with cardiomyopathy, for example arrhythmias. In another embodiment, the subject has been diagnosed with a cardiomyopathy.

In another embodiment, the disclosure provides a method of screening for, diagnosing or detecting ARVD/C and/or an increased risk of developing ARVD/C in a subject comprising detecting the presence of a TMEM43 disease associated variant in a sample of the subject, wherein the presence of the TMEM43 disease associated variant is indicative of ARVD/C and/or an increased risk of developing ARVD/C.

A further embodiment provides a method of diagnosing a predisposition for ARVD/C in a subject comprising detecting the presence of a TMEM43 disease associated variant in a sample of the subject, wherein the presence of the TMEM43 disease associated variant is indicative of a predisposition for ARVD/C. Another embodiment provides a method of identifying a subject with an increased risk of and/or predisposition for ARVD/C comprising detecting in a sample from the subject, a TMEM43 disease associated variant, wherein the presence of the TMEM43 disease associated variant is indicative of an increased risk of ARVD/C. The presence of a TMEM43 disease associated variant is indicative that the subject has ARVD/C or an increased risk of developing ARVD/C compared to an individual not having the TMEM43 disease associated variant.

As used herein the phrase "screening for, diagnosing or detecting ARVD/C" refers to a method or process of determining if a subject has ARVD/C.

As used herein the phrase "screening for, diagnosing or detecting a risk of developing ARVD/C" refers to a method or process of determining if a subject has an increased risk of developing ARVD/C.

As used herein "cardiomyopathy" refers to diseases of the heart muscle and includes ARVD/C including ARVD/C, associated with ARVD5.

As used herein "ARVD/C" or arrhythmogenic right ventricular dysplasia/cardiomyopathy refers to a cardiomyopathy in which normal myocardium appears to be replaced by fibrofatty tissue. Although ARVD/C was initially described as a disease of the right ventricle it is also a biventricular disorder. ARVD/C has a genetic component. Hence the methods, compositions and kits described are useful for identifying presymptomatic subjects and/or subjects with an increased risk of and/or predisposition for developing ARVD/C as well as diagnosing subjects with ARVD/C. Symptoms associated with ARVD/C may include palpitations ventricular tachycardia, pre-syncope or light headedness, syncope or fainting, which are all vague symptoms found in the general population. A final outcome can include heart failure and sudden death. ARVD/C is alternatively referred to as ARVC or arrhythmic cardiomyopathy.

As used herein "ARVD/C associated with ARDV5" refers to ARVD/C associated with and/or caused by mutations in the ARVD5 locus. For example, the methods, compositions and kits described herein are useful for identifying subjects who are negative for mutations associated with loci other than ARVD5 e.g. in desmosomal genes such as mutations in desmoplakin, plakophilin, desmoglein and/or plakoglobin not associated with ARVD5. A person skilled in the art would recognize that ARVD/C associated with may be related to deficiencies in desmosomal pathways, eg through functional interactions.

As used herein "TMEM43" or "transmembrane protein 43" refers to a TMEM43 gene including gene introns and its gene products including transcribed nucleic acids and translated polypeptides (such as TMEM43 gene, TMEM43 transcripts, TMEM43 polypeptides). TMEM43 is also known as LUMA and has been suggested to reside in the inner nuclear membrane and ER[43]. TMEM43 optionally refers to the full sequence or a portion thereof which retains TMEM43 activity. In a preferred embodiment TMEM43 refers to human TMEM43.

"Wild-type TMEM43 gene" or "wild-type TMEM43 gene products" as used herein refers to common naturally occurring forms of the TMEM43 gene or gene products that are not associated with disease. In one embodiment, wild type TMEM43 has the genomic sequence (SEQ ID NO:1) wherein nucleotide at genomic position 14158166 is cytosine. In one embodiment, wild type TMEM43 has the nucleic acid sequence identified by Genbank Accession number NM_024334 (SEQ ID NO:2). In another embodiment wild type TMEM43 has the protein sequence identified by Genbank Accession number NP_077310 protein (SEQ ID NO:3). Protein and polypeptide are used herein interchangeably. Various isoforms of TMEM43 exist.

In addition, the inventors have conducted extensive database analysis using ECGene Model and EMBL-EBI databases. ECGene Model with alternative splicing reports 953 sequences corresponding to TMEM43 that include 1 RefSeq, 12 mRNA, 940 EST sequences. According to ECgene bioinformatic analysis, this gene produces 34 transcript variants encoding 18 distinct proteins for human TMEM43 The transcript variants include Transcript ID's: H3C1779.1, H3C1779.2, H3C1779.3#R, H3C1779.4, H3C1779.5, H3C1779.6, H3C1779.7, H3C1779.8, H3C1779.9, H3C1779.10, H3C1779.11, H3C1779.12, H3C1779.13, H3C1779.14, H3C1779.15, H3C1779.16, H3C1779.17, H3C1779.18, H3C1779.19, H3C1779.20, H3C1779.21, H3C1779.22, H3C1779.23, and H3C1779.24. Searches in EMBL-EBI database reports 6 transcripts. A person skilled in the art will recognize that the TMEM43 disease associated variants are readily detected in any of the above variants and/or in any of the encoded polypeptides.

The Ensembl data base EBI IDs are identified by searching for ENSG00000170876743.

As used herein "TMEM43 disease associated variant" means any TMEM43 molecule, nucleic acid, including an allele, or polypeptide that comprises at least one modification and/or alteration compared to wild-type TMEM43 that is associated with or useful for screening, diagnosing or detecting an increased risk of developing ARVD/C. The modification and/or alteration is optionally a TMEM43 gene mutation, for example a germline mutation. As used herein, a "TMEM43 gene mutation" refers to a nucleotide change (and/or nucleotide changes) in the TMEM43 gene allele or alleles that is/are reflected in nucleic acid and polypeptide gene products that is/are not present in wild-type TMEM43 gene or gene products which are not associated with disease. The gene mutation is in one embodiment inherited e.g. a germline mutation. In another embodiment, the gene mutation is sporadic (eg. a somatic mutation). TMEM43 gene mutations include without limitation, missense mutations, deletion mutations, point mutations, and/or insertion mutations. Accordingly TMEM43 gene mutations include nucleotide polymorphisms such as single nucleotide polymorphisms associated with disease.

In an embodiment, the TMEM43 disease associated variants comprise TMEM43 polypeptide mutated at serine 358, TMEM43 transcripts mutated at cytosine 1073 and/or TMEM43 gene mutated at cytosine at genomic position 14158166, including missense mutations, deletions, and insertions.

In another embodiment, the TMEM43 disease associated variants consist of TMEM43 polypeptide mutated at serine 358, TMEM43 transcripts mutated at cytosine 1073 and/or TMEM43 gene mutated at cytosine at genomic position 14158166, including missense mutations, deletions, and insertions.

In an embodiment, the TMEM43 disease associated variants comprise S358L, 1073 C>T, and/or 14158166 C>T.

In another embodiment, the TMEM43 disease associated variants is selected from S358L, 1073 C>T and 14158166 C>T. In another embodiment, the TMEM43 disease associated variant comprises a S358L mutation. In a further embodiment, the TMEM43 disease associated variant comprises a 1073 C>T mutation. In yet a further embodiment, the TMEM43 disease associated variant comprises a 14158166 C>T mutation.

A person skilled in the art would recognize that the genomic mutation, 14158166 C>T is optionally detected in the opposite DNA strand. A person skilled in the art will understand that primers probes and other reagents can be designed to detect the corresponding mutation in the non-coding allele.

TMEM43 gene mutations are readily detected by analyzing the TMEM43 gene or its gene products. For example nucleic acids and/or polypeptides corresponding to a TMEM43 gene are optionally sequenced and compared to corresponding wild-type sequences. Gene mutations are optionally detected by analyzing genomic sequence.

In the general population, the predominant nucleotide found at genome position 14158166 in subjects without ARVD/C or an increased risk of developing ARVD/C is cytosine (for example, see position 171 in SEQ ID NO:1 and SEQ ID NO:4). The inventors have shown that the nucleotide corresponding to genome position 14158166 is modified in subjects with ARVD/C or an increased risk of developing ARVD/C from cytosine (C) to thymidine (T).

In an embodiment, the TMEM43 disease associated variant is a germline mutation. In an embodiment, the germline mutation comprises 14158166 C>T. In another embodiment, detecting a TMEM43 disease associated variant comprises determining whether there is a germline alteration in the TMEM43 gene and/or TMEM43 gene regulatory sequence. The inventors have further shown that the gene mutation that results in thymidine at the nucleotide corresponding to genome position 14158166 is typically a missense mutation.

A "missense mutation" as used herein refers to a mutation in a nucleotide that changes a codon for one amino acid into a codon for a different amino acid. The TMEM43 disease associated variant comprising this gene mutation is optionally referred to as 14158166C>T and it changes the coded for amino acid from serine to leucine in the TMEM43 polypeptide. Accordingly, in an embodiment the TMEM43 disease associated variant comprises a gene mutation of a nucleotide corresponding to genome position 14158166 (genome build NCBI Build 36.1 (May 2006) accessed online through Genome Browser http://genome.ucsc.edu/). In another embodiment, the gene mutation of the nucleotide corresponding to genome position 14158166 is a missense mutation. In another embodiment, the missense mutation is mutation to thymidine (T) (for example, see position 1073 in SEQ ID NO:4). In yet a further embodiment the TMEM43 disease associated variant is 14158166C>T.

The term "corresponding to" as used herein means situated in a different sequence position but having sequence characteristics in common, including identical, or substantially identical, nucleotide sequence flanking the mutation (eg. substantial identity is optionally at least 75% identity over four or more contiguous nucleotides). For example, "a nucleotide corresponding to genome position 14158166" refers to a nucleotide that is equivalently situated in terms of flanking sequence and relative position number in TMEM43 but that may be identified by a different genome position in another build (eg the related context). Similarly, "corresponding to position 1073 in TMEM43 mRNA" refers to a nucleotide that is equivalently situated in terms of flanking sequence and relative position in TMEM43 but that may be identified by a different nucleotide number in a different transcript. Further "corresponding to" can refer to derived from or related to, for example a nucleic acid corresponding to a gene refers to a nucleic acid derived from the gene such as a transcript and/or an amplified or synthetic copy related to the gene. Similarly, an amino acid sequence corresponding to a nucleic acid refers to an amino acid that is coded for by the nucleic acid.

A person skilled in the art will recognize that mutations at this position such as deletion of one or more nucleotides comprising the nucleotide at position 14158166 will also be associated with ARVD/C or an increased risk of developing ARVD/C. Similarly, it is expected that modification of this nucleotide to guanine or adenosine would also be associated with ARVD/C or an increased risk of developing ARVD/C. Accordingly in an embodiment, the gene mutation comprises a deletion of a nucleotide at genome position 14158166. In another embodiment, the nucleotide detected at genome position 14158166 is guanine or adenine.

Gene mutations are optionally detected by analyzing nucleic acids corresponding to the TMEM43 gene such as RNA transcripts e.g. mRNA or complementary DNA (cDNA). In the general population, the predominant nucleotide found in TMEM43 mRNA at position 1073 in subjects without ARVD/C or an increased risk of developing ARVD/C is cytosine (SEQ ID NO:2). The inventors have shown that the nucleotide found at position 1073 in TMEM43 mRNA (NM_0234334) is modified in subjects with ARVD/C or an increased risk of developing ARVD/C, from cytosine (C) to thymidine (T). The inventors have shown that this mutation is a missense mutation. The TMEM43 disease associated variant comprising this gene mutation is optionally referred to as 1073C>T (nucleotide 1222SEQ ID NO:5). Accordingly, in one embodiment the TMEM43 disease associated variant detected comprises a gene mutation in a nucleotide corresponding to position 1073 in TMEM43 mRNA. Position 10723 in TMEM43 mRNA corresponds to position 1222 of SEQ ID NO:5. In one embodiment the gene mutation is a missense mutation. In another embodiment, the nucleotide detected at position 1222 of SEQ ID NO:5 which corresponds to position 10723 in TMEM43 mRNA is thymidine. In yet a further embodiment, the TMEM43 diseases associated variant is 1073C>T. A person skilled in the art will recognize nucleotide mutations in mRNA can be detected using corresponding cDNA. Further a person skilled in the art will recognize that mutations at this position such as deletion of one or more nucleotides comprising the nucleotide at position 1073 will also be associated with ARVD/C or an increased risk of developing ARVD/C. Similarly, it is expected that modification of this nucleotide to guanine or adenosine would also be associated with ARVD/C or an increased risk of developing ARVD/C. Accordingly in one embodiment, the modification comprises a deletion of nucleotide at position 1073 in TMEM43 mRNA. In another embodiment, the nucleotide detected at 1073 is guanine or adenine.

Gene mutations are optionally detected by analyzing polypeptides corresponding to the TMEM43 gene. The inventors have shown that the amino acid found at position 358 in TMEM43 protein (NP_077310) (SEQ ID NO:3) is modified in subjects with ARVD/C or an increased risk of developing ARVD/C from serine (Ser) to leucine (Leu) (SEQ ID NO:6). The TMEM43 disease associated variant comprising this mutation is optionally referred to as Ser358Leu and or S358L. Accordingly, in an embodiment the TMEM43 disease associated variant detected comprises a modification in amino acid corresponding to position 358 in TMEM43 polypeptide. In another embodiment, the amino acid detected at position 358 is leucine (SEQ ID NO:6). In yet a further embodiment, the TMEM43 disease associated variant is S358L. A person skilled in the art will recognize that modifications at this position such as deletion of one or more amino acids comprising the amino acid at position 358 will also be associated with ARVD/C or an increased risk of developing ARVD/C. Similarly, it is expected that modification of this amino acid to other branched amino acids would also be associated with ARVD/C or an increased risk of developing ARVD/C. For example, it is shown that a nucleotide change in TMEM43 mRNA at position 1073 results in introduction of leucine (i.e nucleotide change to thymidine) as mentioned above, a stop codon (i.e. nucleotide change to adenine) or tryptophan (i.e. nucleotide change to guanine). A person skilled in the art will understand that additional amino acid changes result from changes in the first (i.e nucleotide 1072) and third (i.e. nucleotide 1074) nucleotides of the codon coding for the amino acid at position 358. Accordingly in one embodiment, the modification comprises a deletion of amino acid at position 358 in TMEM43 polypeptide. In another embodiment, the amino acid detected at a position 358 is tryptophan. In another embodiment the amino acid at 358 is replaced by a stop codon.

Other modifications can include post-translational modifications of serine 358 in TMEM43.

A person skilled in the art will understand that positions of mutations provided are relative to the particular accession numbers and SEQ ID NOS provided. A person skilled in the art would readily be able to determine corresponding position in any TMEM43 isoforms, TMEM43 homologues, TMEM43 sequence fragments or other related sequences.

The terms "risk" and "increased risk" as used herein refer to a subject having a predisposition to developing a disease e.g increased risk compared to the average risk of a population. The predisposition is optionally inherited, or optionally acquired (e.g sporadic mutation). The increased risk is relative to a subject not having a TMEM43 disease associated variant.

The term "sample" and "sample of a subject" as used herein refer to any sample of a subject that comprises nucleic acids or polypeptide and/or includes sequence or sequence data corresponding to TMEM43 gene, RNA or protein sequence. For example, a priori sequenced TMEM43 gene, RNA or protein sequence is optionally used to detect TMEM43 disease associated variants. In one embodiment, the sample comprises blood, whole blood or a fraction thereof. As the inventors have shown that TMEM43 is expressed in white blood cells, in one embodiment the sample is any fluid, cell preparation or tissue comprising white blood cells. In a further embodiment, the sample comprises B-lymphocytes. In another embodiment, the sample comprises cardiac tissue, and/or cardiac cells. In another embodiment, the sample is selected from the group consisting of fresh tissue such as a biopsy, frozen tissue and paraffin embedded tissue. In other embodiments, the sample comprises any nucleated cell from the human body and any cell lines generated to express TMEM43.

The term "subject" as used herein includes all members of the animal kingdom including multicellular organisms, including mammals, and preferably means humans.

As mentioned previously, ARVD/C is difficult to diagnose. The inventors have determined that the methods described herein identify individuals presymptomatically. Accordingly, in one embodiment, the individual is presymptomatic.

ARVD/C is associated with several known loci and cloned genes. The ARVD5 haplotype, which is associated with an autosomal dominant form of ARVD/C, maps to chromosome 3p. As used herein "ARVD5 haplotype" and/or "ARVD5 locus" means the allele or alleles of ARVD5 that are associated with ARVD/C. Given the severity of the ARVD/C, its variable presentation and penetrence, the methods described herein are useful, for example, for screening relatives of individuals known to have ARVD/C and/or known to be carriers of the ARVD5 haplotype.

As used herein, "a relative" or "blood relation" is a relative genetically related, or related by birth, and includes without limitation $1^{st}$, $2^{nd}$, $3^{rd}$, $4^{th}$, $5^{th}$, $6^{th}$, $7^{th}$, $8^{th}$, $9^{th}$ and $10^{th}$ degree relations, for example but not limited to parents, children, grandchildren, grandparents, cousins and/or $2^{nd}$ cousins related by blood.

Isolated Nucleic Acids and Compositions

TMEM43 disease associated variants are readily detected using isolated nucleic acids and/or compositions comprising isolated nucleic acids or polypeptides that are specific for a TMEM43 disease associated variant.

Accordingly in one aspect, the application provides compositions comprising isolated nucleic acids useful for detecting TMEM43 disease associated variants. Another aspect provides an isolated nucleic acid molecule comprising a nucleic acid sequence comprising a TMEM43 gene or transcript disease associated variant.

Another aspect provides a reagent for detecting a TMEM43 disease associated variant, such as an isolated nucleic acid primer or probe. In an embodiment, the isolated nucleic acid molecule comprises:

a) any one of SEQ ID NOs: 1-54, and/or combinations thereof; and/or b) a nucleic acid molecule with at least 80%, 90%, 95%, or 99% sequence identity to a), characterized in that the nucleic acid molecule is capable of binding TMEM43 under moderately stringent conditions. In an embodiment, the nucleic acid with at least 80%, 90%, 95%, or 99% sequence identity to a) binds TMEM43 under moderately stringent conditions and is capable of priming strand synthesis. Isolated nucleic acid molecules including for example SEQ ID NOs: 1-52 are useful as primers to amplify TMEM43. In an embodiment, the isolated nucleic acid molecule is an amplified which is produced by amplification of a TMEM43 disease associated variant containing template. Isolated nucleic acid molecules including for example SEQ ID NO: 53 and/or 54, are useful for as probes to detect TMEM43 disease associated variants.

The term "isolated nucleic acid sequence" and/or "oligonucleotide" as used herein refers to a nucleic acid substantially free of cellular material or culture medium when produced by recombinant DNA techniques, or chemical precursors, or other chemicals when chemically synthesized. The term "nucleic acid" and/or "oligonucleotide" as used herein refers to a sequence of nucleotide or nucleoside monomers consisting of naturally occurring bases, sugars, and intersugar (backbone) linkages, and is intended to include DNA and RNA which can be either double stranded or single stranded, represent the sense or antisense strand. The term also includes modified or substituted oligomers comprising non-naturally occurring monomers or portions thereof, which function similarly, which are referred to herein as "chemical analogues" and/or "oligonucleotide analogues" such as "peptide nucleic acids". Such modified or substituted nucleic acids may be preferred over naturally occurring forms because of properties such increased stability in the presence of nucleases.

One aspect of the application provides a composition comprising at least one isolated nucleic acid sequence, wherein the at least one isolated nucleic acid molecule hybridizes to:

a) a RNA product of TMEM43;

b) a nucleic acid sequence complementary to a); and/or c) a nucleic acid sequence corresponding to a);

wherein the composition is used to detect a TMEM43 disease associated variant. In an embodiment, a) comprises a TMEM43 disease associated variant. In an embodiment, the nucleic acid complementary to or corresponding a) comprises genomic sequence.

The term "hybridize" refers to the sequence specific non-covalent binding interaction with a complementary nucleic acid. One aspect of the application provides an isolated nucleotide sequence, which hybridizes to a RNA product of TMEM43 or a nucleic acid sequence which is complementary to an RNA product of a gene of TMEM43. In one embodiment the hybridization is conducted under at least moderately stringent conditions. In a preferred embodiment, the hybridization is under high stringency conditions. Appropriate stringency conditions which promote hybridization are known to those skilled in the art, or can be found in Current Protocols in Molecular Biology, John Wiley & Sons, N.Y. (1989), 6.3.1 6.3.6. For example, 6.0× sodium chloride/sodium citrate (SSC) at about 45° C. for 15 minutes, followed by a wash of 2.0×SSC at 50° C. for 15 minutes may be employed.

The stringency may be selected based on the conditions used in the wash step. For example, the salt concentration in the wash step can be selected from a high stringency of about 0.2×SSC at 50° C. for 15 minutes. In addition, the temperature in the wash step can be at high stringency conditions, at about 65° C. for 15 minutes.

By "at least moderately stringent hybridization conditions" it is meant that conditions are selected which promote selective hybridization between two complementary nucleic acid molecules in solution. Hybridization may occur to all or a portion of a nucleic acid sequence molecule. The hybridizing portion is typically at least 15 (e.g. 20, 25, 30, 40 or 50) nucleotides in length. Those skilled in the art will recognize that the stability of a nucleic acid duplex, or hybrids, is determined by the Tm, which in sodium containing buffers is a function of the sodium ion concentration and temperature (Tm=81.5° C.−16.6 (Log 10 [Na+])+0.41(%(G+C)−600/l), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a >95% sequence identity, the final wash temperature will be reduced by about 5° C. Based on these considerations those skilled in the art will be able to readily select appropriate hybridization conditions. In preferred embodiments, stringent hybridization conditions are selected. By way of example the following conditions may be employed to achieve stringent hybridization: hybridization at 5× sodium chloride/sodium citrate (SSC)/5×Denhardt's solution/1.0% SDS at Tm−5° C. based on the above equation, followed by a wash of 0.2×SSC/0.1% SDS at 60° C. for 15 minutes. Moderately stringent hybridization conditions include a washing step in 3×SSC at 42° C. for 15 minutes. It is understood, however, that equivalent stringencies may be achieved using alternative buffers, salts and temperatures. Additional guidance regarding hybridization conditions may be found in: Current Protocols in Molecular Biology, John Wiley & Sons, N.Y., 1989, 6.3.1-6.3.6 and in: Sambrook et al., Molecular Cloning, a Laboratory Manual, Cold Spring Harbor Laboratory Press, 2000, Third Edition.

The term "sequence identity" as used herein refers to the percentage of sequence identity between two polypeptide sequences or two nucleic acid sequences. To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions.times.100%). In one embodiment, the two sequences are the same length. The determination of percent identity between two sequences can also be accomplished using a mathematical algorithm. A preferred, non-limiting example of a mathematical algorithm utilized for the comparison of two sequences is the algorithm of Karlin and Altschul, 1990, Proc. Natl. Acad. Sci. U.S.A. 87:2264-2268, modified as in Karlin and Altschul, 1993, Proc. Natl. Acad. Sci. U.S.A. 90:5873-5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecules of the present application. BLAST protein searches can be performed with the XBLAST program parameters set, e.g., to score-50, wordlength=3 to obtain amino acid sequences homologous to a protein molecule described herein. To obtain gapped alignments for comparison purposes, Gapped BLAST can be utilized as described in Altschul et al., 1997, Nucleic Acids Res. 25:3389-3402. Alternatively, PSI-BLAST can be used to perform an iterated search which detects distant relationships between molecules (Id.). When utilizing BLAST, Gapped BLAST, and PSI-Blast programs, the default parameters of the respective programs (e.g., of XBLAST and NBLAST) can be used (see, e.g., the NCBI website). The percent identity between two sequences can be determined using techniques similar to those described above, with or without allowing gaps. In calculating percent identity, typically only exact matches are counted. In an embodiment, the isolated nucleic acids are useful as primers.

The term "primer" as used herein refers to a nucleic acid sequence, whether occurring naturally as in a purified restriction digest or produced synthetically, which is capable of acting as a point of synthesis when placed under conditions in which synthesis of a primer extension product, which is complementary to a nucleic acid strand is induced (e.g. in the presence of nucleotides and an inducing agent such as DNA polymerase and at a suitable temperature and pH). The primer must be sufficiently long to prime the synthesis of the desired extension product in the presence of the inducing agent. The exact length of the primer will depend upon factors, including temperature, sequences of the primer and the methods used. A primer typically contains 15-25 or more nucleotides, although it can contain less. The factors involved in determining the appropriate length of primer are readily known to one of ordinary skill in the art.

The inventors designed a number of primers useful for detecting whether TMEM43 gene changes. These primers were custom designed with the assistance of Primer3 primer design program.

TABLE A

| Primer Name | Primer Sequence | |
|---|---|---|
| TMEM43 primers | | |
| cDNA primers designed to cover the whole translated region | | |
| NM_024334cDNA-Ex1-4-F | GTCAGCCCACTTCCTAGCTG | SEQ ID NO: 15 |
| NM_024334cDNA-Ex1-4-R | CCTCGTCTCCTTCTTCACCT | SEQ ID NO: 16 |
| NM_024334-cDNA-Ex4-9-F | AGAATGAAGGAAGGCTGGTG | SEQ ID NO: 17 |

TABLE A-continued

TMEM43 primers

| Primer Name | Primer Sequence | |
|---|---|---|
| NM_024334-cDNA-Ex4-9-R | TGGTGGAGAATGGGACTAGC | SEQ ID NO: 18 |
| NM_024334-cDNA-Ex4-12-F | CGCCGTGGAGACTTTTTCTA | SEQ ID NO: 19 |
| NM_024334-cDNA-Ex9-12-R | ACCTGGATCCTAGGGCTCAC | SEQ ID NO: 20 |
| NM_024334-cDNA-Ex1-10-F | GTCAGCCCACTTCCTAGCTG | SEQ ID NO: 21 |
| NM_024334-cDNA-Ex1-10-R | CCCAGGTCTTCATGGAGTTG | SEQ ID NO: 22 |
| NM_024334-cDNA-Ex5-12-F | ATCTTCCGGCTGTGAAACTG | SEQ ID NO: 23 |
| NM_024334-cDNA-Ex5-12-R | AGAGGGAGTGCAGAGTCCAA | SEQ ID NO: 24 |

Genomic DNA primers designed to cover the 5' and 3' untranslated regions all exons, intron exon boundaries and some flanking intronic sequence.

| Primer Name | Primer Sequence | |
|---|---|---|
| NM_024334-Ex1-F | CAATGTCCCGGACCGTATAG | SEQ ID NO: 25 |
| NM_024334-Ex1-R | GGCGAAATGGACCTAGAGGA | SEQ ID NO: 26 |
| NM_024334-Ex2-F | AGTTTTCATTCTGTTACTGTTTCTTTT | SEQ ID NO: 27 |
| NM_024334-Ex2-R | GGCCCTTGATTACCAAATCC | SEQ ID NO: 28 |
| NM_024334-Ex3-F | AACTGTACGGTGGGGAGATG | SEQ ID NO: 29 |
| NM_024334-Ex3-R | ATCACTCCCATGTGTGACCA | SEQ ID NO: 30 |
| NM_024334-Ex4-F | AAGAACCTGGGACAGGGAGT | SEQ ID NO: 31 |
| NM_024334-Ex4-R | CTCCTGGAGCCACTCTTCAC | SEQ ID NO: 32 |
| NM_024334-Ex5&6-F | TGATCTGGTAGCCCTGAGGT | SEQ ID NO: 33 |
| NM_024334-Ex5&6-R | CACGAGGCAGGATTAACTCAA | SEQ ID NO: 34 |
| NM_024334-Ex7-F | CCTGGGCTAATCTGGACTTG | SEQ ID NO: 35 |
| NM_024334-Ex7-R | CTGATCCTGTGCCTTTAGCC | SEQ ID NO: 36 |
| NM_024334-Ex8&9-F | CGTGGACGAGACAGAGTCAG | SEQ ID NO: 37 |
| NM_024334-Ex8&9-R | CGCTCCTGACATTGACCAAG | SEQ ID NO: 38 |
| NM_024334-Ex10-F | GGGTTTCTGTGCTCACTTCC | SEQ ID NO: 39 |
| NM_024334-Ex10-R | TGCCTCATTCACTGGCTATG | SEQ ID NO: 40 |
| NM_024334-Ex11-F | TGTTCAGAAATGGCCAACAG | SEQ ID NO: 41 |
| NM_024334-Ex11-R | CTCATCCCAAGGCTATGGAG | SEQ ID NO: 42 |
| NM_024334-Ex12a-F | CCCATCCTCATCTAGGGACA | SEQ ID NO: 43 |
| NM_024334-Ex12a-R | GGAAACAGCAGGAGAAGCTG | SEQ ID NO: 44 |
| NM_024334-Ex12b-F | TGGTGTTCACCAGCTCATGT | SEQ ID NO: 45 |
| NM_024334-Ex12b-R | TTCCTCTTGGGGTAGGAAAG | SEQ ID NO: 46 |
| NM_024334-Ex12c-F | TCCTGAGGAGAAAAGCTGGA | SEQ ID NO: 47 |
| NM_024334-Ex12c-R | CGTGGGCATTGTACAACCAG | SEQ ID NO: 48 |
| NM_024334-Ex12d-F | CGATTAAGAGAAAAGGTTGGAA | SEQ ID NO: 49 |
| NM_024334-Ex12d-R | GAGATTTGATGAAATTGCTCATGTA | SEQ ID NO: 50 |
| NM_024334-Ex12e-F | TTGTGCCTGCTGGGAGTAAT | SEQ ID NO: 51 |
| NM_024334-Ex12e-R | ATCCTATGGCTGAATTCTTTACA | SEQ ID NO: 52 |

In another aspect, the application describes probes that are useful for detecting a TMEM43 disease associated variant. Where the variation is only a single nucleotide change, for example 1073C>T shorter probes used at high stringency are useful. For example, oligonucleotide probes having a sequence length ranging from 16 to 20 nucleotides, comprising, within the sequence, for example, at the centre, a nucleotide specific for the alleleic variants of the gene coding for a TMEM43 disease associated variant, wherein the oligonucleotide probes hybridizes with the TMEM43 disease associated variant. In an embodiment the probe comprise ctgtgtggccacctTgctga (SEQ ID NO:53) to detect the disease variation. The normal variation is one embodiment detected using a probe comprising ctgtgtggccacctCgctga (SEQ ID NO:54)

A person skilled in the art will recognize that all or part of the above probes can be used.

The term "probe" as used herein refers to a nucleic acid sequence that will hybridize to a nucleic acid target sequence. In one example, the probe hybridizes to an RNA TMEM43 disease associated variant or a nucleic acid sequence complementary to the RNA TMEM43 disease associated variant. The length of probe depends on the hybridize conditions and the sequences of the probe and nucleic acid target sequence. In one embodiment, the probe is at least 8, 10, 15, 20, 25, 50, 75, 100, 150, 200, 250, 400, 500 or more nucleotides in length.

In certain embodiments the isolated nucleic acid comprises a detectable label, such as a fluorescent or radioactive label.
Detection Methods for the Presence of a TMEM43 Mutation The presence of a TMEM43 disease associated variant are readily detected using methods that detect a gene mutation in a TMEM43 disease associated variant gene, RNA gene product, such as TMEM43 transcripts, and/or polypeptide gene product.
Detecting Nucleic Acid TMEM43 Disease Associated Variants A person skilled in the art will appreciate that a number of methods are useful for detect the presence of a TMEM43 disease associated variant in a TMEM43 nucleic acid.

For example a variety of techniques are known in the art for detecting a gene mutation or alteration within a sample, including genotyping, microarrays, Restriction Fragment Length Polymorphism, Southern Blots, SSCP, dHPLC, single nucleotide primer extension, allele-specific hybridization, allele-specific primer extension, oligonucleotide ligation assay, and invasive signal amplification, Matrix-assisted laser desorption/ionization time-of-flight (MALDI-TOF) mass spectrometry, and Fluorescence polarization (FP). Such methods optionally employ the isolated nucleic acid compositions of the disclosure. The TMEM43 disease associated variants, such as germline alterations, are readily detected by TMEM43 gene analysis. For example, this can be accomplished by gene amplification analysis such as polymerase chain reaction (PCR) analysis of TMEM43 or a part thereof, optionally followed by sequencing, and comparing the TMEM43 amplification profile or sequence to a wild-type TMEM43 amplification profile or wild-type TMEM43 sequence. In an embodiment, one or more TMEM43 exons are amplified by PCR, and analyzed for gene mutations, for example by single-strand conformation polymorphism (SSCP). In an embodiment, one or more TMEM43 exons are sequenced and analyzed for gene mutations, for example by comparing the sequence obtained from a sample of a subject, to wild-type TMEM43 sequence. The full exon or a part thereof, for example a part know to be associated with disease, for example a part comprising a nucleotide corresponding to the nucleotide shown at genome position 14158166, is optionally PCR amplified and/or sequenced. Detecting "T" at 14158166 is indicative of having ARVD/C or an increased risk of developing ARVD/C. In another embodiment, 2, 3, 4, 5, 6, 7, 8, 9, 10, 11, or 12 exons, or parts thereof, are PCR amplified and/or sequenced and the PCR profile and/or sequence analyzed for gene mutations. Accordingly, the presence of a TMEM43 gene mutation is detected in one embodiment by sequencing. Methods of sequencing are well known in the art. In one method, primers flanking a TMEM43 mutation are selected, for example primers which amplify exon 12 either in genomic sequence and/or corresponding transcripts, and used to amplify the gene region comprising a TMEM43 mutation. The amplified region is sequenced and analysed. In another embodiment the TMEM43 mutation comprises a thymidine corresponding to position 14158166 of genome build 36.1. In an embodiment the primers used to detect the mutation 14158166C>T or 1073 C>T mutation comprise:

| Primer Name | Primer Sequence | |
|---|---|---|
| NM_024334-Ex12a-F | CCCATCCTCATCTAGG GACA | (SEQ ID NO: 43) |
| NM_024334-Ex12a-R | GGAAACAGCAGGAGAA GCTG | (SEQ ID NO: 44) |

Gene mutations can be detected by detecting the presence of the mutation in the gene or in a corresponding transcribed sequence. A variety of techniques are known in the art that are suitable for detecting mutations in the gene or in a corresponding transcribed sequence.

For example, primers which span one or more exons that comprise the putative location of a TMEM43 disease associated variant, are useful to detect TMEM43 disease associated variants. In an embodiment, a composition comprising SEQ ID NO: 19 and SEQ ID NO:20 is used to detect mutations at 1073, such as 1073C>T. In another embodiment, a composition comprising SEQ ID NO:23 and SEQ ID NO:24 is used to detect mutations at 1073. A person skilled in the art readily designs and uses suitable additional primers based on the sequences provided herein.

In another embodiment, TMEM43 disease associated variants are readily detected by polymerase chain reaction (PCR), real time PCR, multiplex ligation dependent probe amplification (MLPA), nucleic acid sequence based amplification (NASBA) and/or real time NASBA. As used herein "NASBA" refers to a sensitive isothermal transcription-based amplification method used for example for RNA research. NASBA technology is optionally applied to single nucleotide polymorphism (SNP) analysis using human genomic DNA as a template. For example combination of DNA NASBA with multiplex hybridization of specific molecular beacons makes it possible to discriminate the presence of mutations of interest (Berard, C, Cazalis M A, Leissner P, Mougin B., DNA nucleic acid sequence-based amplification-based genotyping for polymorphism analysis. Biotechniques. 2004, 37:680-2, 684, 686).

In another embodiment, the method of detecting the presence of a TMEM43 disease associated variant comprises a probe that specifically hybridizes a TMEM43 disease associated variant. The probe optionally hybridizes to an mRNA sequence, corresponding complementary DNA or copy DNA (cDNA) or a genomic sequence. The probe can hybridize a TMEM43 mutation directly or an amplified product comprising the TMEM43 gene mutation. In another embodiment the probe binds upstream or downstream of a TMEM43 gene mutation. For example, in one embodiment an amplified region comprising a TMEM43 gene mutation is hybridized using a composition comprising a probe specific for the TMEM43 gene mutation (e.g. "T") under stringent hybridization conditions. In an embodiment the probe comprises all or part (e.g. 10-19 nucleotides, or any number in between) of ctgtgtggccacctTgctga (SEQ ID NO:53) to detect the disease variation. The normal variation is in an embodiment detected using a probe comprising all or part (e.g. 10-19 nucleotides, or any number in between) of ctgtgtggccacctCgctga (SEQ ID NO:54). A person skilled in the art would recognize that a probe that hybridizes to a sequence in the non-coding (and/or corresponding sequence such as cDNA) comprising the TMEM43 disease associated variant is also useful with the methods, compositions and kits described herein.

In one embodiment, PCR or RT-PCR is employed to detect the presence of a TMEM 43 mutation. For example, PCR and RT-PCR and primers flanking the mutation are employed to amplify TMEM43 gene sequence and transcript sequence respectively in a sample comprising DNA (for PCR) or RNA (for RT-PCR). The amplified products are optionally sequenced to determine if a TMEM43 disease associated variant is present in the sample.

In another embodiment, the method of detecting the presence of a TMEM43 mutation comprises use of a restriction enzyme. For example amplified products can be digested with a restriction enzyme that specifically recognizes sequence comprising a TMEM43 disease associated variant but does not recognize sequence corresponding to the wild-type or non-disease associated TMEM43.

ARVD/C is an inheritable disease. Where a genetically related family member has been determined to have a TMEM43 disease associated variant, the genetic relation is readily screened specifically for mutations at cytosine 1073 of a TMEM43 transcript, and/or cytosine 14158166 of a TMEM43 genome. For example the genetic relation is optionally screened for 1073C>T and/or 14158166 C>T. Accordingly, in an embodiment, the subject has a genetic relation having a TMEM43 disease associated variant, such as mutation at 1073 of a TMEM43 transcript, mutation at 14158166 of TMEM43 genomic sequence, such as 1073C>T and 14158166C>T. In an embodiment primers flanking TMEM43 1073, and/or flanking TMEM43 14158166, for example, which hybridize within 50, 60, 70, 80, 90, 100, 150, 200, 250, 300, 350, 400, 450, 500 nucleotides upstream and within 50, 60, 70, 80, 90, 100, 150, 200, 250, 300, 350, 400, 450, 500 nucleotides downstream, are used to detect mutations at TMEM43 1073 or TMEM43 14158166.

A TMEM43 disease associated variant can also be detected using a DNA microarray.

Detecting Polypeptide TMEM43 Disease Associated Variants

A person skilled in the art will recognize that there are several methods known in the art for detecting a polypeptide TMEM43 disease associated variant.

A polypeptide TMEM43 disease associated variant is optionally detected using a binding agent that specifically binds a TMEM43 disease associated variant polypeptide gene products and not wild type TMEM43 polypeptide gene products. In one embodiment, the binding agent is an isolated polypeptide.

The term "isolated polypeptide" as used herein refers to a proteinaceous agent, such as a peptide, polypeptide or protein, which is substantially free of cellular material or culture medium when produced recombinantly, or chemical precursors, or other chemicals, when chemically synthesized.

The phrase "bind to polypeptide products" as used herein refers to binding agents such as isolated polypeptides that specifically bind to TMEM43 disease associated variants described in the application. In an embodiment, isolated polypeptides are antibodies or antibody fragments.

The term "antibody" as used herein is intended to include monoclonal antibodies, polyclonal antibodies, and chimeric antibodies. The antibody may be from recombinant sources and/or produced in transgenic animals. The term "antibody fragment" as used herein is intended to include Fab, Fab', F(ab')$_2$, scFv, dsFv, ds-scFv, dimers, minibodies, diabodies, and multimers thereof and bispecific antibody fragments. Antibodies can be fragmented using conventional techniques. For example, F(ab')$_2$ fragments can be generated by treating the antibody with pepsin. The resulting F(ab')$_2$ fragment can be treated to reduce disulfide bridges to produce Fab' fragments. Papain digestion can lead to the formation of Fab fragments. Fab, Fab' and F(ab')$_2$, scFv, dsFv, ds-scFv, dimers, minibodies, diabodies, bispecific antibody fragments and other fragments can also be synthesized by recombinant techniques.

To produce human monoclonal antibodies, antibody producing cells (lymphocytes) can be harvested from a human having cancer and fused with myeloma cells by standard somatic cell fusion procedures thus immortalizing these cells and yielding hybridoma cells. Such techniques are well known in the art, (e.g. the hybridoma technique originally developed by Kohler and Milstein (Nature 256:495-497 (1975)) as well as other techniques such as the human B-cell hybridoma technique (Kozbor et al., Immunol. Today 4:72 (1983)), the EBV-hybridoma technique to produce human monoclonal antibodies (Cole et al., Methods Enzymol, 121: 140-67 (1986)), and screening of combinatorial antibody libraries (Huse et al., Science 246:1275 (1989)). Hybridoma cells can be screened immunochemically for production of antibodies specifically reactive with TMEM43 disease associated variants and the monoclonal antibodies can be isolated.

Specific antibodies, or antibody fragments, reactive against particular TMEM43 disease associated antigens, may also be generated by screening expression libraries encoding immunoglobulin genes, or portions thereof, expressed in bacteria with cell surface components. For example, complete Fab fragments, VH regions and FV regions can be expressed in bacteria using phage expression libraries (See for example Ward et al., Nature 341:544-546 (1989); Huse et al., Science 246:1275-1281 (1989); and McCafferty et al., Nature 348: 552-554 (1990)).

In one embodiment isolated polypeptides, antibodies or antibody fragments are used to detect a TMEM43 disease associated variant. In one embodiment the isolated polypeptides, antibodies or antibody fragments are labeled with a detectable marker.

The label is preferably capable of producing, either directly or indirectly, a detectable signal. For example, the label may be radio-opaque or a radioisotope, such as $^3$H, $^{13}$C, $^{32}$P, $^{35}$S, $^{123}$I, $^{125}$I, $^{131}$I; a fluorescent (fluorophore) or chemiluminescent (chromophore) compound, such as fluorescein isothiocyanate, rhodamine or luciferin; an enzyme, such as alkaline phosphatase, beta-galactosidase or horseradish peroxidase; an imaging agent; or a metal ion.

In another embodiment, the detectable signal is detectable indirectly. For example, a secondary antibody that is specific for the isolated protein described in the application and contains a detectable label is useful to detect the isolated polypeptide described in the application.

A person skilled in the art will appreciate that a number of methods can be used to detect a polypeptide TMEM43 disease associated variant, including immunoassays such as Western blots, ELISA, and immunoprecipitation followed by SDS-PAGE, as well as immunocytochemistry or immunohistochemistry.

The application also contemplates the use of "peptide mimetics" for detecting polypeptide TMEM43 gene products. Peptide mimetics are structures which serve as substitutes for peptides in interactions between molecules (See Morgan et al (1989), Ann. Reports Med. Chem. 24:243-252 for a review). Peptide mimetics include synthetic structures which may or may not contain amino acids and/or peptide bonds but retain the structural and functional features of the isolated proteins described in the application, such as its ability to bind to the polypeptide product of a TMEM43 disease associated variant described in the application. Peptide mimetics also include peptoids, oligopeptoids (Simon et al (1972) Proc. Natl. Acad, Sci USA 89:9367); and peptide libraries containing peptides of a designed length representing all possible sequences of amino acids corresponding to the cleavage recognition sequence described in the application.

Peptide mimetics may be designed based on information obtained by systematic replacement of L-amino acids by D-amino acids, replacement of side chains with groups having different electronic properties, and by systematic replacement of peptide bonds with amide bond replacements. Local conformational constraints can also be introduced to determine conformational requirements for activity of a candidate peptide mimetic. The mimetics may include isosteric amide bonds, or D-amino acids to stabilize or promote reverse turn conformations and to help stabilize the molecule. Cyclic amino acid analogues may be used to constrain amino acid residues to particular conformational states. The mimetics can also include mimics of inhibitor peptide secondary structures. These structures can model the 3-dimensional orientation of amino acid residues into the known secondary conformations of proteins. Peptoids may also be used which are oligomers of N-substituted amino acids and can be used as motifs for the generation of chemically diverse libraries of novel molecules.

ARVD/C is an inheritable disease. Where a genetically related family member has been determined to have a TMEM43 disease associated variant, the genetic relation is readily screened specifically for mutations at serine 358 of a TMEM43 polypeptide. Accordingly in an embodiment, the subject has a genetic relation comprising a TMEM43 disease associated variant, such as mutation at serine 358, such as S358L.

In an embodiment the binding agents are fixed to a solid support. In a further embodiment the solid support is an ELISA plate.

Polypeptide TMEM43 disease associated variants can also be detected using tissue arrays.

Microarrays

As mentioned, the presence of a TMEM43 disease associated variant can optionally be detected using arrays including DNA microarrays and tissue microarrays. A "microarray" as used herein refers to an ordered set of probes fixed to a solid surface that permits analysis such as gene analysis of a plurality of genes. A DNA microarray refers to an ordered set of DNA fragments fixed to the solid surface. For example, in one embodiment the microarray is a gene chip. A tissue microarray refers to an ordered set of tissue specimens fixed to a solid surface. For example, in one embodiment the tissue microarray comprises a slide comprising an array of arrayed tumor biopsy samples in paraffin. Tissue microarray technology optionally allows multiple specimens, such as biopsy samples, to be analysed in a single analysis at the DNA, RNA or protein level. Tissue microarrays are analysed by a number of techniques including immunohistochemistry, in situ hybridization, in situ PCR, RNA or DNA expression analysis and and/or morphological and clinical characterization or a combination of techniques. The specimens are optionally from the same subject or from a plurality of subjects. Methods of detecting gene expression using arrays are well known in the art. Such methods are optionally automated. In one embodiment, a sample of an ARVC/D subject is analyzed using a tissue microarray.

Kits

Another aspect of the disclosure is a kit for screening for, diagnosing the presence of, or detecting a risk of developing, ARVD/C. In one embodiment the kits comprise, one or more isolated nucleic acid molecules and/or compositions described herein and instructions for use.

In an embodiment the kit comprises an isolated nucleic acid molecule or composition that specifically hybridizes to a TMEM43 disease associated variant, e.g. a probe. In an embodiment the nucleic acid molecule comprises SEQ ID NO:53. In another embodiment, the nucleic acid molecule comprises a detectable label such as a fluorescent molecule. In a further embodiment, the kit comprises an isolated nucleic acid molecule useful as a primer. In an embodiment, the primer is selected from all or part of (e.g. at least 10 or 15 nucleotides, or any number in between) of SEQ ID NO: 1-52. In another embodiment the kit comprises at least two nucleic acids wherein one hybridizes to a wildtype or non-disease associated TMEM43 containing molecule, for example SEQ ID NO:54 and the other hybridizes to a TMEM43 disease associated variant containing molecule, for example SEQ ID NO:53. In another embodiment the at least two isolated nucleic acids are primers for amplifying a sequence comprising a TMEM43 disease associated variant. In an embodiment, the at least two isolated nucleic acid molecules comprise two or more of all or part of SEQ ID NOs: 1-52. In a further embodiment, the at least two nucleic acid molecules comprise all or part of a primer pair listed in Table A. In a further embodiment, the primers are selected from the group comprising SEQ ID NOS: 43-44.

As used herein "all or part of" of a probe or primer refers to the portion sufficient for in the case a probe, sufficient to specifically hybridize to the intended target and in the case of a primer, sufficient to prime amplification of the intended template.

In other embodiments the kit comprises a binding agent such as an antibody that specifically binds a TMEM43 disease associated variant polypeptide and instructions for use. In a further embodiment the kit comprises an isolated antibody specific for an epitope present in a TMEM43 disease associated variant that is not present in a non-disease associated or wild-type TMEM43.

In certain embodiments, the kit is a diagnostic kit for medical use. In other embodiments, the kit is a diagnostic kit for laboratory use.

In another aspect the disclosure provides a commercial package comprising an isolated nucleic acid or composition described herein and instructions for use.

Assay for Identifying Additional TMEM43 Disease Associated Variants

Other TMEM43 disease associated variants are identified by screening other populations for TMEM43 mutations that are infrequently or not present in non-diseased subjects, e.g. normal population without ARVD/C. For example the primers in Table A are useful to screen individuals known to have ARVD/C. Sequence comparison between subjects known to have ARVD/C and subjects known not have ARVD/C readily identify additional mutations. For example, a pedigree is typically established as described in Example 1.

Accordingly, in an embodiment, the disclosure provides a method for identifying TMEM43 disease associated variants comprising determining whether there is a germline alteration in the sequence of TMEM43 gene or a TMEM43 gene regulatory sequence in a sample of a subject, wherein the subject has or is suspected of having ARVD/C. In an embodiment, the sequences of the TMEM43 gene or TMEM43 gene regulatory sequence in the sample is compared with the sequence of one or more wild type TMEM43 gene sequences, for example as in SEQ ID NO: 1. In another embodiment, determining the germline mutation comprises determining the sequence of a TMEM43 gene transcript. In another embodiment, the sequence of the TMEM43 gene transcript is compared with the sequence of one or more wild type TMEM43 gene transcript sequences, such as in SEQ ID NO:2, and/or a transcript described herein. In an embodiment, the disclosure provides a method for identifying TMEM43 disease associated variants comprising amplifying a TMEM43, gene or transcript or part thereof from a sample of a subject, comparing the amplified region to a control population, wherein a mutation that is detected in the sample and is rare or undetected in the control population is a TMEM43 disease associated variant. In an embodiment, one or more of the nucleic acids of Table A are used to amplify a TMEM43 gene or transcript or part thereof. In another embodiment, the part thereof comprises or corresponds to an exon and/or exon/intron boundary. In another embodiment, the part thereof comprises intronic TMEM43 sequence.

The TMEM43 mutation is optionally a deletion mutation, a missense mutation, a point mutation, and/or a mutation that affects TMEM43 expression levels.

In an embodiment, the method for identifying TMEM43 disease associated variants comprises detecting the level and/or sequence of an expression product of TMEM43 in the sample.

In another embodiment, the disclosure provides a method for identifying a TMEM43 disease associated variant comprising determining whether there is an amino acid alteration in the TMEM43 polypeptide in the sample compared to the sequence of wild type TMEM43 polypeptide, for example SEQ ID NO:3.

Combination Testing

A person skilled in the art will recognize that the methods, isolated nucleic acids, compositions, and kits are optionally combined with methods, isolated nucleic acids, compositions and kits useful for detecting other forms of ARVD/C.

Screening Assay for Identifying Substances Useful for Treating ARVD/C

The application also includes screening assays for detecting substances that target or bind TMEM43. The application also includes screening assays for detecting substances that target or bind a TMEM43 disease associated variant, which are useful to treat ARVD/C. These assays may be in in vitro or in vivo format. In a suitable embodiment the application provides a cell based assay for evaluating whether a candidate compound is capable of binding a TMEM43 disease associated variant.

Accordingly, the application provides a method of identifying substances which bind a TMEM43 disease associated variant comprising:

a) contacting a TMEM43 disease associated variant with a test substance, under conditions which allow for formation of a complex between the TMEM43 disease associated variant and the test substance, and b) detecting for complexes between TMEM43 disease associated variant and the test substance, wherein the presence of complexes indicates that the test substance binds the TMEM43 disease associated variant.

Detecting is optionally done by chemically detecting complexes, free test substance or non-complexed TMEM43 disease associated variant. In one embodiment, the TMEM43 disease associated variant contacted with a test substance is a polypeptide. Test substance-protein complexes, free test substance or non-complexed TMEM43 disease associated variant polypeptides may be isolated by conventional isolation techniques, for example, salting out, chromatography, electrophoresis, gel filtration, fractionation, absorption, polyacrylamide gel electrophoresis, agglutination, or combinations thereof. To facilitate the assay of the components, antibody against a TMEM43 disease associated variant or the test substance, or a labelled TMEM43 disease associated variant, or a labelled test substance may be utilized. The antibodies, proteins, or substances may be labelled with a detectable substance as described elsewhere.

Binding to a TMEM43 disease associated variant is optionally assessed using a TMEM43 disease associated variant or test substance that is insolubilized. For example, TMEM43 disease associated variant or a test substance may be bound to a suitable carrier. Examples of suitable carriers are agarose, cellulose, dextran, Sephadex, Sepharose, carboxymethyl cellulose polystyrene, filter paper, ion-exchange resin, plastic film, plastic tube, glass beads, polyamine-methyl vinyl-ether-maleic acid copolymer, amino acid copolymer, ethylene-maleic acid copolymer, nylon, silk, etc. The carrier may be in the shape of, for example, a tube, test plate, beads, disc, sphere etc. The proteins or substance may also be expressed on the surface of a cell.

The insolubilized protein or substance may be prepared by reacting the material with a suitable insoluble carrier using known chemical or physical methods, for example, cyanogen bromide coupling.

Another aspect involves use of animal ARVD/C models and TMEM43 disease associated variant transgenic mice and *Drosophila melanogaster* for identifying and testing compound that target or bind TMEM43 disease associated variants. Nucleic acids, polypeptides or small organic molecules are optionally tested in these assays. The application includes all compounds that are identified with the screening methods of the application and which are suitable for administration to subjects in pharmaceutical compositions.

Treatment

The inventors have previously reported that implantable cardioverter defibrillator (ICD) therapy increases survival in autosomal dominant arrhythmogenic right ventricular cardiomopathy (including ARVD/C associated with ARVD5).

Accordingly an aspect provides a method of identifying subjects that would benefit from ICD therapy comprising detecting a TMEM43 disease associated variant in a subject according to a method described herein, wherein the presence of the TMEM43 disease associated variant identifies that the subject would benefit from ICD therapy.

The disclosure also provides a method of treatment for subjects with ARVD/C and/or a risk of developing ARVD/C comprising:
  a) detecting a TMEM43 disease associated variant in a subject according to a method described herein;
  b) providing ICD therapy for the subject having the TMEM43 disease associated variant.

In a further embodiment, the disclosure provides use of ICD therapy for a subject comprising a TMEM43 disease associated variant, detected according to a method described herein. ARVD/C patients are typically treated with drugs that are part of a group of antiarrhythmic agents. These drugs are outlined below. In this population these drugs may also be used in conjunction with an ICD. In this case, the ICD is used to prevent sudden death due to ventricular fibrillation, while the antiarrhythmic agents are use to suppress ventricular tachyarrhythmia's so that the ICD doesn't shock the patient as often There are five main classes in the Vaughan Williams classification which was introduced in 1970 and classifies a drug bases on the primary mechanism of its antiarryhythmic effect: a problem when many agents have multiple action mechanisms.
  Class I agents—interfere with the sodium (Na+) channel
    Class Ia—includes quinidin, procainamide and disopyramide
    Class Ib—includes lidocaine, mexiletine, tocainide and phenytoin
    Class Ic—includes encainide, flacainide, moricizine and propafenone
  Class II agents—act by selectively blocking the effects of catecholamines at the $\beta_1$-adrenergic receptors. All agents in this class are beta blockers and include esmolol, propranolol and metoprolol, where metoprolol is most commonly prescribed for ARVC.
  Class III agents predominantly block the potassium channels and prolong repolarization. These are generally prescribed for the treatment of refactory VT or VF or treatment of atrial or ventricular tachyarrhythmias and AV re-entrant arrhythmias. This class includes amiodarone, azimilide, bretylium, clofilium, dofetilide, tedisamil, ibutilide, sematilide and sotalol, where amiodarone and sotalol are the most commonly prescribed for ARVC.
  Class IV agents affect the AV node as they are slow calcium channel blockers and include verapamil and diltiazem.
  Class V agents work by other or unknown mechanisms and include digoxin (increase vagal activity via its action on the central nervous system, thus decreasing the conduction of electrical impulses throughout the AV node) and adenosine.

A "treatment" or "prevention" regime of a subject with a therapeutically effective amount of an agent, such as the drugs described herein may consist of a single administration, or alternatively comprise a series of applications. For example, the agent may be administered at least once a week. However, in another embodiment, the agent may be administered to the subject from about one time per week to about once daily for a given treatment. The length of the treatment period depends on a variety of factors, such as the severity of the disease, the age of the patient, the concentration and the activity of the agent, or a combination thereof. It will also be appreciated that the effective dosage of the agent used for the treatment or prophylaxis may increase or decrease over the course of a particular treatment or prophylaxis regime. Changes in dosage may result and become apparent by standard diagnostic assays known in the art. In some instances, chronic administration may be required.

It is to be understood that, as used herein "a", "an" and/or "the' includes one and/or more than one.

The following non-limiting examples are illustrative of the present disclosure:

EXAMPLES

Example 1

Arrhythmogenic right ventricular dysplasia/cardiomyopathy (ARVD/C) in its most severe presentation, causes sudden cardiac death. To date, there are 11 known loci and seven cloned genes. The ARVD5 locus was mapped to chromosome 3p in an extended Newfoundland family (AR1) in 1998. Subsequently, the inventors ascertained several other Newfoundland families that shared the ARVD5 haplotype with family AR1, and determined that improved survival occurred in patients with an implantable cardioverter defibrillator.

The inventors identified 15 ARVC families that shared the ARVD5 ancestral haplotype and used extensive genotyping and haplotype analyses to reduce the ARVD5 critical region on chromosome 3p. Twenty ARVD5 candidate genes were screened for mutations by direct sequencing. Once identified ARVD5 was identified, both retrospective and prospective clinical data from the past two decades was used to compare clinical outcomes in 257 affected versus 151 unaffected subjects.

Key recombinations to the ARVD5 haplotype reduced the minimal critical region from 9.98 Mb to 2.36 Mb (between markers D3S3610-D3S3613). Direct sequencing of 20 ARVD5 candidate genes revealed 240 variants. One of these, a missense mutation leading to an amino acid substitution in a highly conserved region of the novel protein TMEM43, was found exclusively in all patients across the 15 families, including key recombinants, and in no population controls. Affected and unaffected male and female subjects showed significant differences on first clinical testing for the presence of ectopy (multiple premature ventricular contractions and ventricular tachycardia), poor R wave progression, left ventricular enlargement and systolic dysfunction. A clear sex influence existed with males manifesting earlier clinical sequalea than females including arrhythmia (RR 5.5: 95% CI 1.7-16.8), heart failure (RR 3.4, 95% CI 1.4-8.6) and death (RR 6.8, 95% CI 1.3-10.9). Heart failure occurred in affected males at a later median age (63 years) than death (41 years) indicating that survivors of potentially lethal arrhythmias may develop heart failure.

ARVC at locus ARVD5 is caused by the substitution of a serine to a leucine in a highly conserved region of TMEM43. This founder mutation in the Newfoundland genetic isolate frequently leads to early death due to arrhythmias and heart failure particularly in males. As clinical diagnosis of ARVC is difficult, at-risk families can now be screened for TMEM43 through genetic mutation analysis. The mutation has been traced back for nine generations in some of the ARVC families. Accordingly the mutation likely predates the settling of Newfoundland and would be expected to be present in other populations.

Methods

Study Population

Figure 1B:
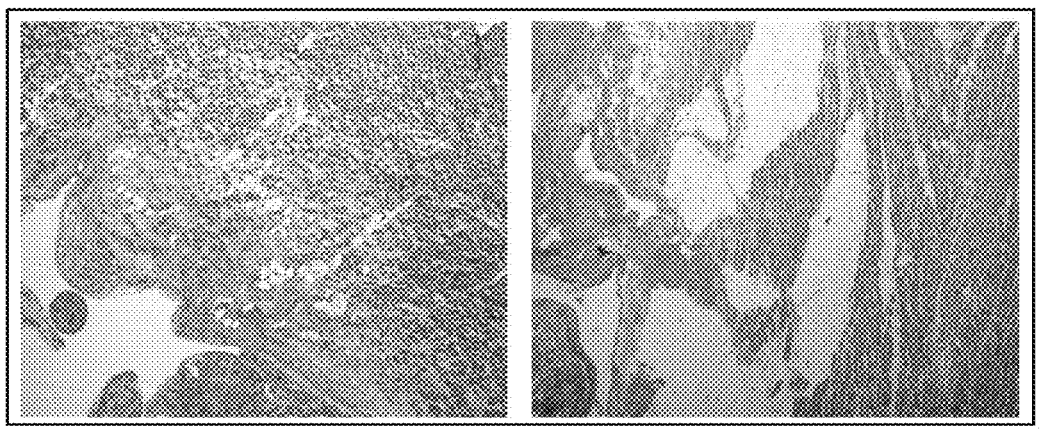
Figure 2:
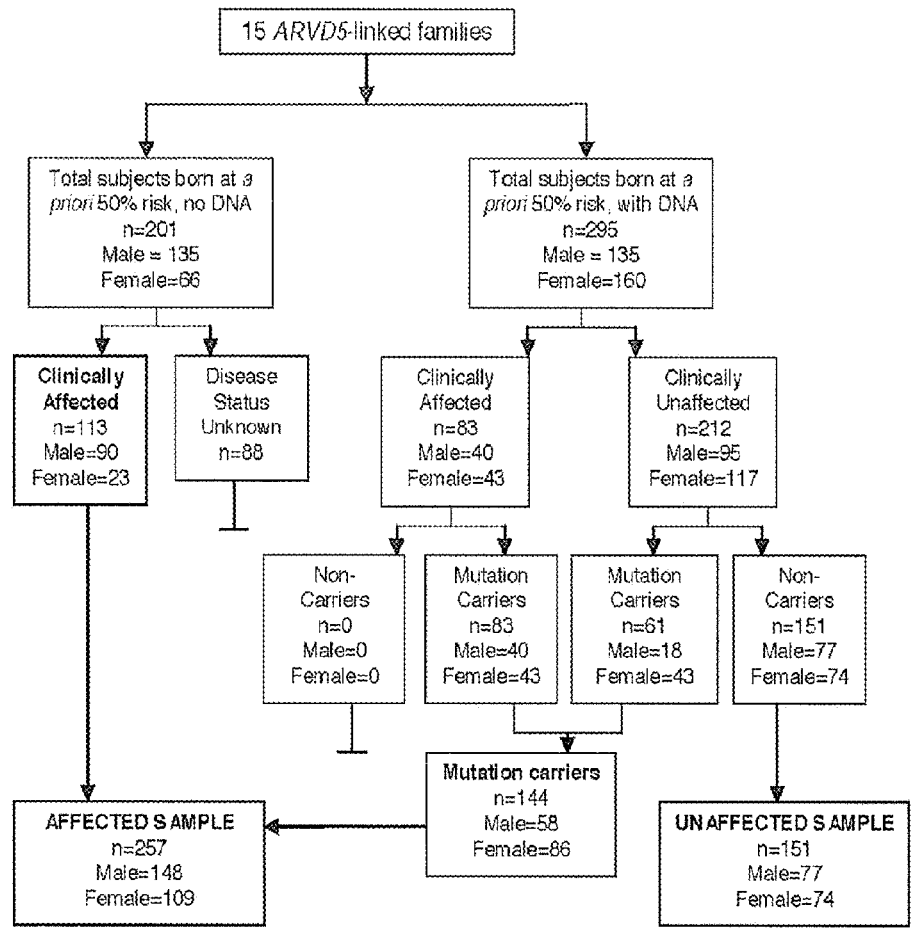

Over the past nine years, approximately 150 families have been referred to either the Newfoundland Labrador provincial genetics program or the Newfoundland Labrador cardiomyopathy genetics clinic because of sudden cardiac death and a family history of cardiomyopathy. Fifteen of these families were determined to have an autosomal dominant form of ARVC based on established criteria[1], a shared haplotype on chromosome 3p and deep genealogies (up to eight generations) (FIG. 1). Informed consent and blood samples were obtained from each subject in compliance with the Human Investigation Committee requirements of the Eastern Health Corporation of St. John's, Newfoundland (study number 00-176). A total of 425 genomic DNA samples were collected from subjects born at a priori 50% risk (obligate carriers and first degree relatives of affected subjects) and those born at less than a priori 50% risk (second and third degree relatives and spouses, a priori 25%, 12.5% and 0%, respectively). Subjects born at a priori 50% risk were further subdivided into three groups based on their affection status (primary, secondary and clinically unaffected) for the molecular arm of the study (FIG. 2).

Refine Mapping of the ARVD5 Locus

A previous study that included a genomewide linkage analysis of Family AR1 (FIG. 1) mapped a novel locus for ARVC to 3p23 and excluded other loci that had been identified for ARVC (14q23; ARVD1, 1q42; ARVD2, 14q12; ARVD3 and 2q32; ARVD4). Fine mapping with microsatellite markers defined a 9.3 cM (9.98 Mb) region between markers D353610-D3S3659.[8] To further refine the critical region and identify the ARVD5 gene the inventors recruited extended members of family AR1 and 14 additional ARVC families from the Newfoundland population (FIG. 1). Extensive haplotyping using 18 polymorphic microsatellite markers was done on subjects at a priori 50% risk with primary affection status. In order to refine the critical region a recombination had to be detected in subjects from at least two families.

Screening Candidate ARVD5 Genes

A mutation screening panel comprised of seven genomic DNA samples from four subjects with primary affection status from three families (AR1, AR8, AR15) and three control samples (spouses) was established. All coding and non-coding exons and intron-exon boundaries of positional candidate genes for ARVD5 were sequenced. All sequences were amplified by polymerase-chain reaction (PCR) assay from genomic DNA in 25 µl reaction volume. The components for the PCR reactions are in µl:

| | |
|---|---|
| 10× PCR Buffer | 2.50 |
| 2 mM dNTP's | 2.50 |
| 50 mM MgCl2 | 0.75 |
| 3.75M Betaine | 5.00/0.00 |
| 5 U/ul DNA Taq Polymerase | 0.20 |
| Water | 11.05/16.05 |
| Forward primer | 1.00 |
| Reverse primer | 1.00 |
| 25 ng/ul DNA | 1.00 |

These conditions were the standard trial conditions for each primer set +/−betaine and the temperature scheme for the PCR reaction was TD54 where the first 5 rounds of PCR decrease the annealing temperature by 2° C. starting at 64° C. for 30 seconds standard denaturing and extension temperatures of 95° C. and 72° C. respectively for 30 seconds each. The following 30 rounds of PCR have an annealing temperature of 54° C. and standard denaturing and extension temperatures of 95° C. and 72° C. respectively for 30 seconds each. These conditions along with the PCR mixture were adjusted if required to achieve the cleanest amplification per primer pair.

The PCR products were purified using 50% sephacryl (Amersham Biosciences) and MultiScreen HTS filter plates (Millipore Corporation). Purified PCR products were cycle sequenced in both forward and reverse directions with the use of BigDye Terminator V3.1 cycle sequencing kit on an automated ABI 3700 DNA analyzer (Applied Biosystems). Sequencing electropherograms were inspected manually and analyzed with Mutation Surveyor software (Transition Technologies). Sequencing variants found exclusively in ARVC subjects were experimentally verified to reside on the ARVC haplotype by segregation analysis in family AR14. The population frequencies of ARVD5-associated alleles were determined with population-based controls obtained through random phone dialing, as part of a large colorectal cancer study. Key recombinant families (AR2 and AR10) were analyzed to determine which rare variants (<1% of the population) were shared amongst subjects with primary affection status (FIG. 2).

Expression of TMEM43 in Myocardium and Lymphocytes of ARVC Patients

Total RNA was extracted from Epstein Barr virus (EBV) transformed B lymphocytes from two affected subjects and one unaffected control and heart tissue from one affected subject and an unrelated control using Trizol (Invitrogen) followed by DNase1 treatment (Ambion). Complementary synthesis (Invitrogen) was performed and analyzed by both size fractionation and direct sequencing with over-lapping primers designed to cover the complete coding sequence of TMEM43.

Bioinformatic Analysis

Conservation of the TMEM43 protein across species was determined using ClustalW and Weblogo[10-12]. Potential protein localization, function, structure and posttranslational modification sites were predicted using the online tools via the ExPASy web site.[12] The effects of amino acid substitutions of protein function were predicted.[13-17] Both the mutant and normal amino acid sequences of TMEM43 were used as input for these online tools to predict based on what is known about other similar proteins, the protein localization, function, structure and posttranslational modification sites. The web addresses of the sites used are available through accessing the main page at:

The following online tools were used:
    9aaTAD—Prediction of Nine Amino Acid Transactivation Domain
    MITOPROT—Prediction of mitochondrial targeting sequences
    Predotar—Prediction of mitochondrial and plastid targeting sequences
    PTS1—Prediction of peroxisomal targeting signal 1 containing proteins
    SignalP—Prediction of signal peptide cleavage sites
    DictyOGlyc—Prediction of GlcNAc O-glycosylation sites in Dictyostelium NetCGlys—C-mannosylation sites in mammalian proteins
NetOGlyc—Prediction of O-GalNAc (mucin type) glycosylation sites in mammalian proteins
NetGlycate—Glycation of epsilon amino groups of lysines in mammalian proteins
NetNGlyc—Prediction of N-glycosylation sites in human proteins
YinOYang—O-beta—GlcNAc attachment sites in eukaryotic protein sequences
big—PI Predictor-GPI Modification Site Prediction
GPI-SOM—Identification of GPI-anchor signals by a Kohonen Self Organizing Map
Myristoylator—Prediction of N-terminal myristoylation by neural networks
NMT—Prediction of N-terminal N-myristoylation
PrePS—Prenylation Prediction Suite
NetAcet—Prediction of N-acetyltransferase A (NatA) substrates (in yeast and mammalian proteins)
NetPhos—Prediction of Ser, Thr and Tyr phosphorylation sites in eukaryotic proteins
NetPhosK—Kinase specific phosphorylation sites in eukaryotic proteins
Sulfinator—Prediction of tyrosine sulfation sites
SulfoSite—Prediction of tyrosine sulfation sites
SUMOplot—Prediction of SUMO protein attachment sites
TerminNator—Prediction of N-terminal modification
NetNES Leucine—rich nuclear export signals (NES) in eukaryotic proteins
PSORT—Prediction of protein subcellular localization
TargetP—Prediction of subcellular location
HMMTOP—Prediction of transmembrane helices and topology of proteins (Hungarian Academy of Sciences)
PredictProtein—Prediction of transmembrane helix location and topology (Columbia University)
SOSUI—Prediction of transmembrane regions (Nagoya University, Japan)
TMHMM—Prediction of transmembrane helices in proteins (CBS; Denmark)
TMpred—Prediction of transmembrane regions and protein orientation (EMBnet-CH)
TopPred—Topology prediction of membrane proteins (France)
GlobPlot—Protein disorder/order/globularity/domain predictor
CLUSTALW [At EBI, PBIL, My Hits or at EMBnet-CH]
WebLogo—Sequence logos at Berkeley/USA The potential effect of the amino acid substitution was assessed using the following tools: SIFT, PANTHER, PolyPhen, SNPs3D and PMut.

Clinical Assessment of TMEM43 Carriers and Non-Carriers

Only well-ascertained subjects born at a priori 50% risk were investigated for clinical outcomes. Subjects were categorized as affected, unaffected or unknown (FIG. 2). Clinical data was collected prospectively over nine years. This involved annual visits by subjects to the cardiomyopathy genetics clinic where 12 lead ECGs, Holter monitors, MRI's, signal averaged ECG's and echocardiograms were done. All cardiac anomalies were noted following clinical testing. Clinical data was also obtained retrospectively from medical records including "at risk" relatives not seen in clinic. All available autopsy results from deceased subjects were obtained.

The prevalence of ECG abnormalities was determined by two physicians blind to disease status. The prevalence of structural cardiac abnormalities was determined on first echocardiogram. Left ventricular enlargement (LVE) was defined as 2 and 3 standard deviations (SD) above a predicted mean: left ventricular end diastolic diameter (LVEDD) >112% (>25D) and LVEDD >117% (>35D).[18] Those with echocardiography reports that did not include measurements were excluded. The prevalence of arrhythmias was determined on first Holter monitor. In subjects with serial Holter monitors, the age to onset of de novo ≥1000 premature ventricular contractions (PVCs) was calculated by time to event analysis, after excluding those with ≥1000 PVCs present at baseline.

Statistical Analysis

Comparisons between survival of affected versus unaffected subjects was calculated by the Kaplan Meier product limit method with censoring occurring at the time of ICD therapy, heart transplantation or last follow-up (defined as the age at the last clinic visit). Relative risk was calculated using Cox's Regression model. Proportions were assessed using Chi Square. A p-value of <0.05 was considered significant (SPSS software, version 14, Chicago USA).

Results

Refine Mapping

Figure 3:
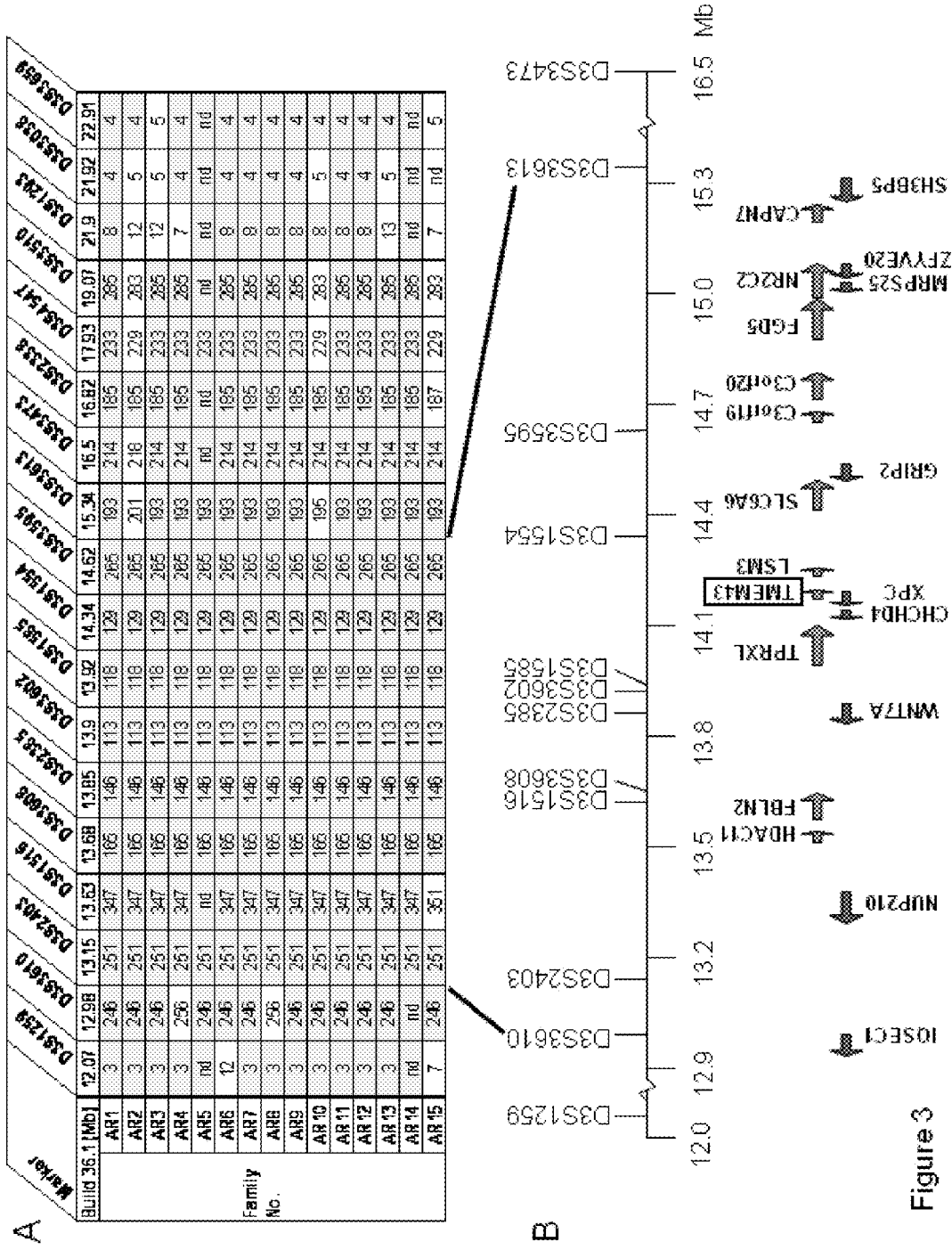

Extensive haplotype analysis both within and across the 15 extended ARVC families refined the genetic interval of ARVD5. Recombinations were identified in subjects in 8 (AR2, AR3, AR4, AR6, AR8, AR10, AR13 and AR15) of the 15 families, subjects from the other six families (AR5, AR7, AR9, AR11, AR12, AR14) shared the full-length ARVD5 haplotype identified in Family AR1 (FIG. 3). Key recombinations in the ARVD5 haplotype reduced the shared haplotype to a physical region between markers D3S3610-D3S3613, reducing the ARVD5 critical region to 2.36 Mb (FIG. 3A). This physical region on chromosome 3p includes 20 annotated genes (FIG. 3B). The apparent recombination at D3S1516 in family AR15 was not taken into account as it was not observed in another family.

Mutation Screening

Figure 9:
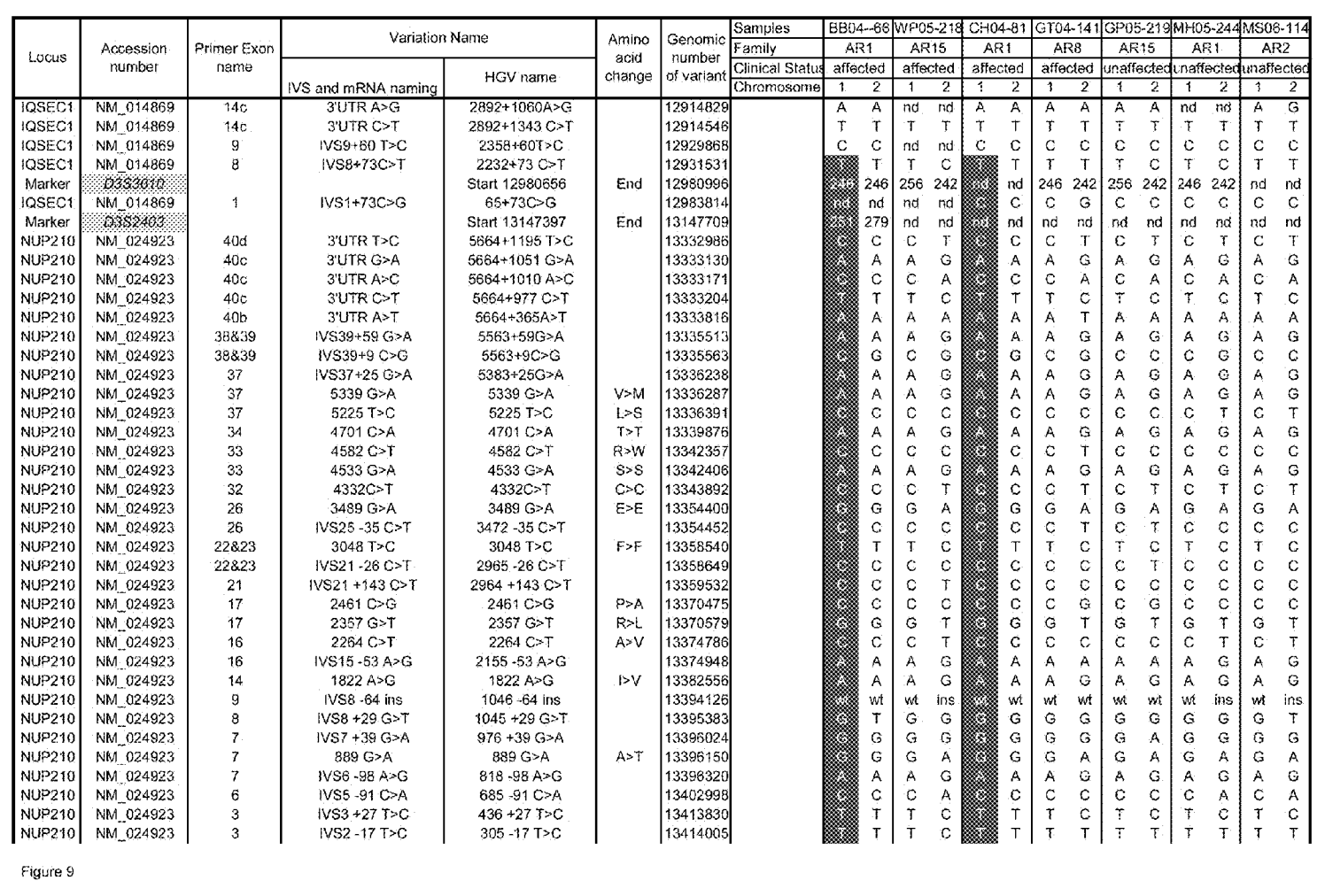
Figure 9:
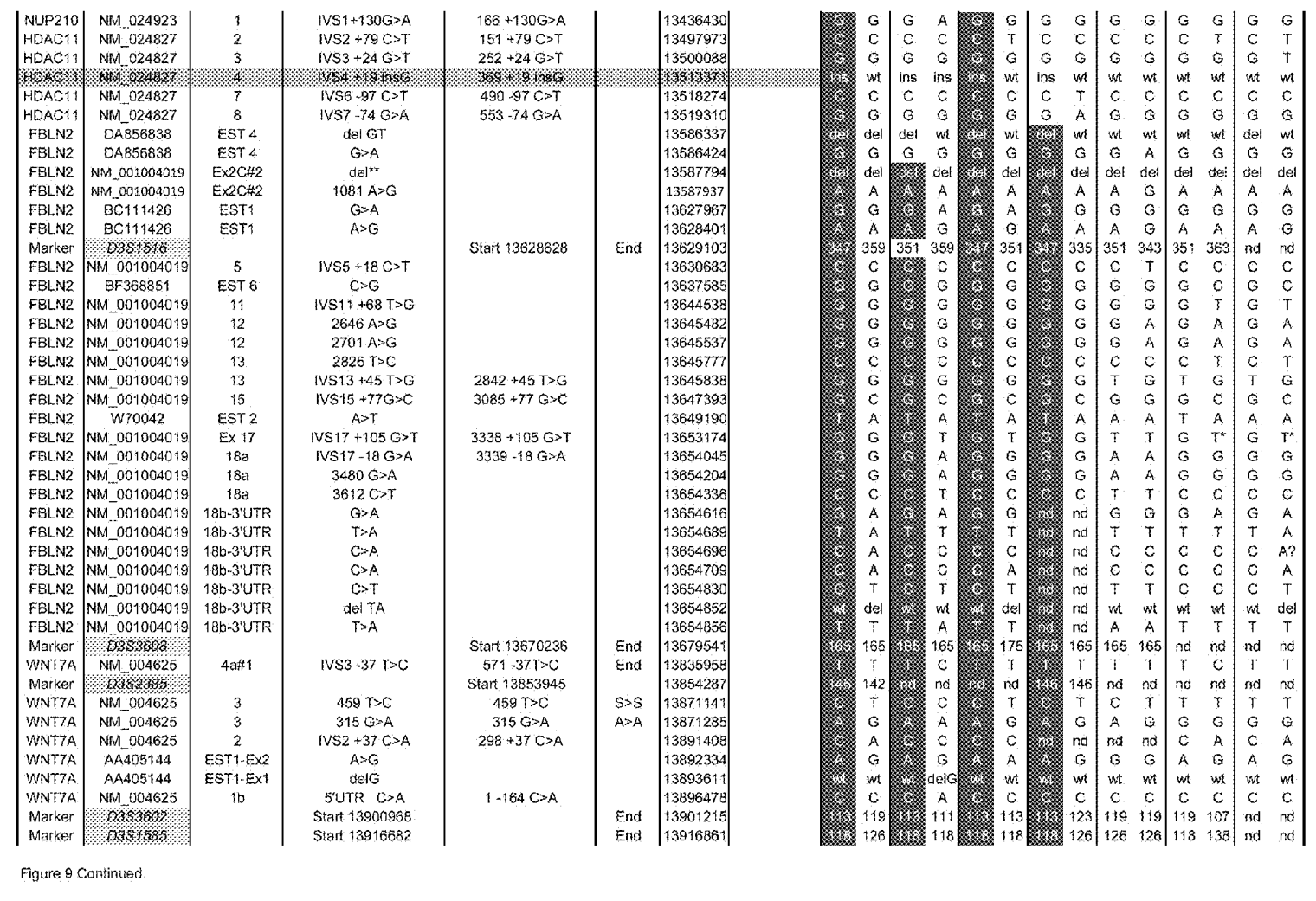
Figure 9:
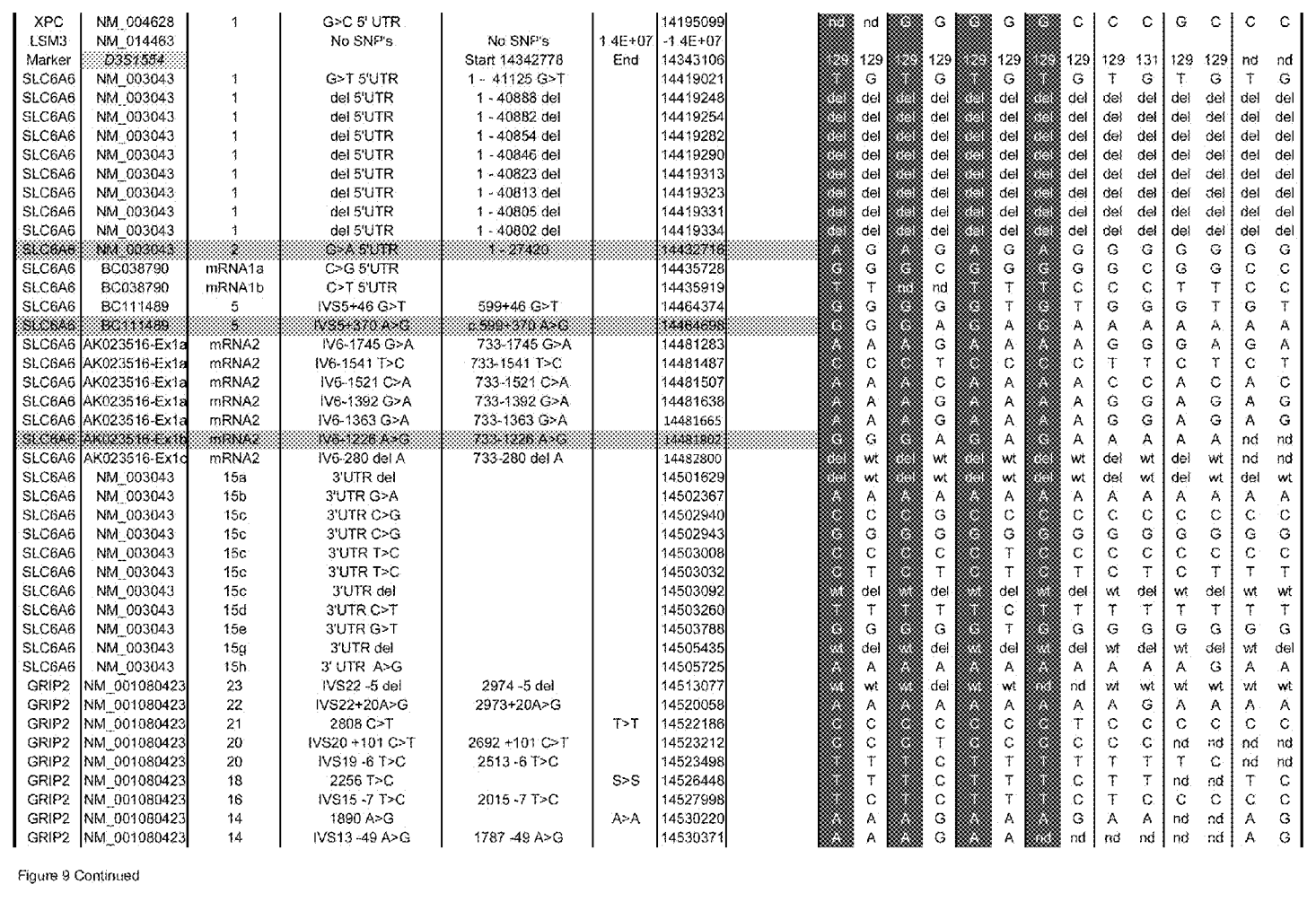
Figure 9:
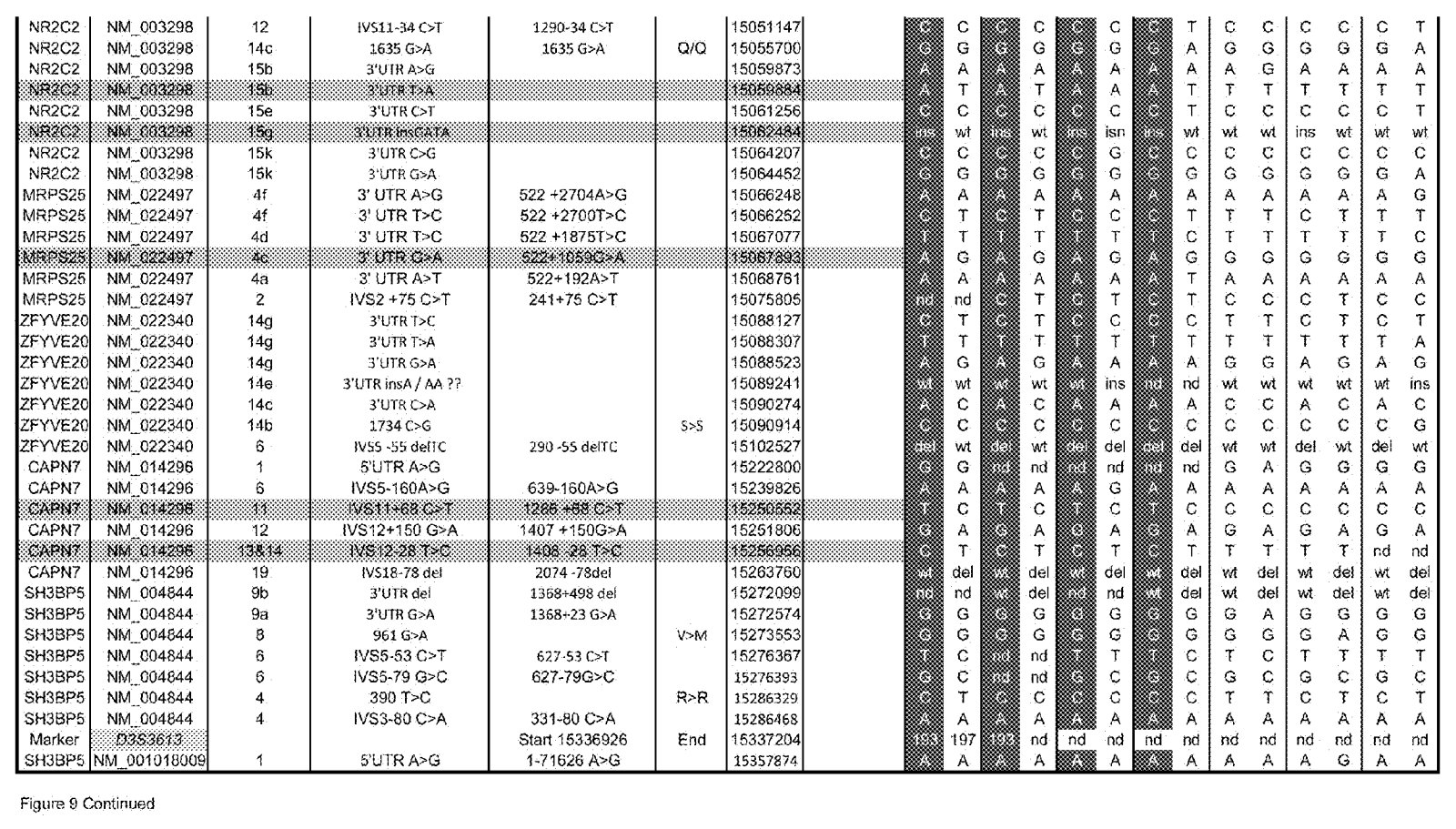
Figure 10:
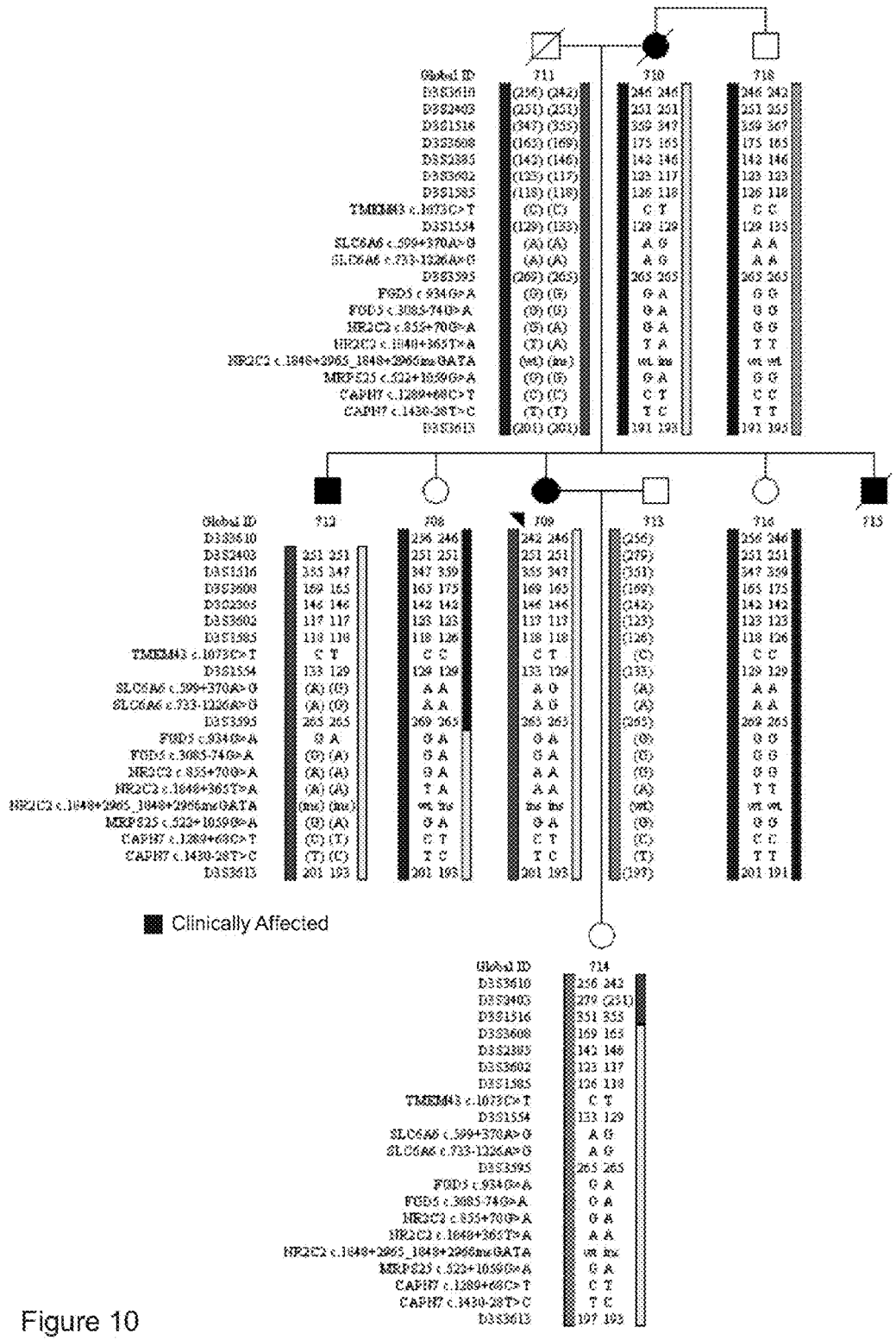
FIG. 10 is a segregation analysis through family AR14 illustrates that eleven of the nineteen variants are on the ARVD5-associated haplotype (white).

The characteristics of the 20 ARVD5 positional candidate genes, namely IQSEC1, NUP210, HDAC11, FBLN2, WNT7A, TPRXL, CHCHD4, TMEM43, XPC, LSM3, SLC6A6, GRIP2, C3orf19, C3orf20, FGD5, NR2C2, MRPS25, ZFYVE20, CAPN7, SH3BP5, are provided (Table 3). Direct sequencing of genomic DNA from subjects on the mutation screening panel revealed a total of 240 sequencing variants across the 20 ARVD5 candidate genes (FIG. 9). Of these 240 variants, only 19 variants were found exclusively in subjects with primary affection status on the mutation screening panel, excluding 221 variants from further analysis (Table. 1). Of these 19 variants, 11 were determined to reside on the ARVD5 ancestral haplotype (FIG. 10) and five were rare (<1% of population chromosomes; Table 1). Only one of the five rare variants, TMEM43 1073 C>T (S358L) (FIG. 4D), was shared by all ARVC subjects with primary affection status across the 15 families. In fact, this was the only rare variant of the five that was still retained on the key recombinant ARVD5 haplotype identified in subjects with primary affection status from families AR2 and AR10 (FIG. 5), which shows that TMEM43 is ARVD5. Additional support comes from the observation that clinically unaffected adults who share distal sections of the ARVD5 haplotype lack the TMEM43 mutation (FIG. 11).

TABLE 1

Nineteen sequencing variants identified exclusively in ARVC subjects with primary affection status.

| Gene Name | Accession# | Variant Nomenclature | Classification | Population Frequency |
|---|---|---|---|---|
| HDAC11 | NM_024827 | c.369 + 18_369 + 19insG | Non-coding | nd |
| THEM43 | NM_024334 | c. 1073C > T | Missense (S > L) | 0% * |
| THEM43 | NM_024334 | c. 1203 + 115T > C | Non-coding | nd |
| XPC | NM_004628 | c.2823 + 684G > C | Non-coding | nd |
| SLC6A6 | NM_003043 | c. 1 – 27420G > A | Non-coding | nd |
| SLC6A6 | NM_003043 | c.599 + 370A > G | Non-coding | 46% |
| SLC6A6 | NM_003043 | c.733 – 1226A > G | Non-coding | 55.60% |
| FGD5 | NM_152536 | c.934G > A | Missense (V > M) | 0.6% * |
| FGD5 | NM_152536 | c.2186 + 22G > A | Non-coding | nd |
| FGD5 | NM_152536 | c.2187 – 82G > A | Non-coding | nd |
| FGD5 | NM_152536 | c.2220G > T | Synonymous (L > L) | nd |
| FGD5 | NM_152536 | c.2613 + 50C > T | Non-coding | nd |
| FGD5 | NM_152536 | c.3085 – 74G > A | Non-coding | 9.00% |
| NR2C2 | NM_003298 | c.855 + 70G > A | Non-coding | 9.10% |
| NR2C2 | NM_003298 | c.1848 + 365T > A | Non-coding | 17.80% |
| NR2C2 | NM_003298 | c.1848 + 2965_1848 + 2966insGATA | Non-coding | 18.30% |
| MRPS25 | NM_022497 | c.522 + 1059G > A | Non-coding | 0% * |
| CAPN7 | NM_014296 | c.1289 + 68C > T | Non-coding | 0.01% * |
| CAPN7 | NM_014296 | c.1430 – 28T > C | Non-coding | 0% * |

Eleven variants (shaded) were determined to be in phase on the ARVD5-ancestral haplotype and were subsequently sequenced on population controls.
* rare variant (<1% of the population)

The assessment included the following features all of which were at a frequency of less than 10% in affected subjects: first degree AV block, T wave inversion in V2 and V3, ST depression anterior, lateral and inferior, ST elevation anterior, lateral and inferior, epsilon waves, tall R wave in V2, V3, left bundle branch block, right bundle branch block, flat/inferior/inverted lateral T waves, short PR interval, long and short QT interval, Inferior, lateral and anterior Q waves, atrial fibrillation, left atrial enlargement, right ventricular enlargement, left anterior and posterior hemiblock, left axis, FS <20% and left ventricular hypertrophy.

TABLE 3

Characteristics of the 20 physical candidate genes mapping within the ARVD5 critical region on 3p25

| Gene Name | Accession Number | Strand | Genomic Position Start | End | Exons |
|---|---|---|---|---|---|
| IQSEC1 | NM_014869 | − | 13,003,536 | 12,917,079 | 13 |
| NUP210 | NM_024923 | − | 13,436,809 | 13,332,737 | 40 |
| HDAC11 | NM_024827 | + | 13,496,824 | 13,521,834 | 10 |
| FBLN2 | NM_001004019 | + | 13,565,625 | 13,654,922 | 18 |
| WNT7A | NM_004625 | − | 13,896,619 | 13,835,083 | 4 |
| TPRXL | AK092426 | + | 13,953,902 | 14,082,480 | 3 |
| CHCHD4 | NM_144636 | − | 14,141,323 | 14,128,584 | 4 |
| TMEM43 | NM_024334 | + | 14,141,546 | 14,160,180 | 12 |
| XPC | NM_004628 | − | 14,195,143 | 14,161,651 | 16 |
| LSM3 | NM_014463 | + | 14,195,341 | 14,214,840 | 4 |
| SLC6A6 | NM_003043 | + | 14,419,110 | 14,503,973 | 15 |
| GRIP2 | NM_001080423 | − | 14,558,592 | 14,510,177 | 25 |
| C3orf19 | NM_016474 | + | 14,668,278 | 14,689,167 | 11 |
| C3orf20 | NM_032137 | + | 14,691,658 | 14,789,544 | 17 |
| FGD5 | NM_152536 | + | 14,835,810 | 14,950,899 | 20 |
| NR2C2 | NM_003298 | + | 14,964,240 | 15,065,782 | 15 |

TABLE 3-continued

Characteristics of the 20 physical candidate genes
mapping within the ARVD5 critical region on 3p25

| | | | Genomic Position | | |
|---|---|---|---|---|---|
| Gene Name | Accession Number | Strand | Start | End | Exons |
| MRPS25 | NM_022497 | − | 15,081,820 | 15,065,024 | 4 |
| ZFYVE20 | NM_022340 | − | 15,115,659 | 15,086,584 | 14 |
| CAPN7 | NM_014296 | + | 15,222,737 | 15,269,426 | 21 |
| SH3BP5 | NM_004844 | − | 15,349,108 | 15,271,250 | 9 |
| | | | | Total | 275 |

ARVC at Locus ARVD5 is Caused by a Missense Mutation in TMEM43

Figure 4:
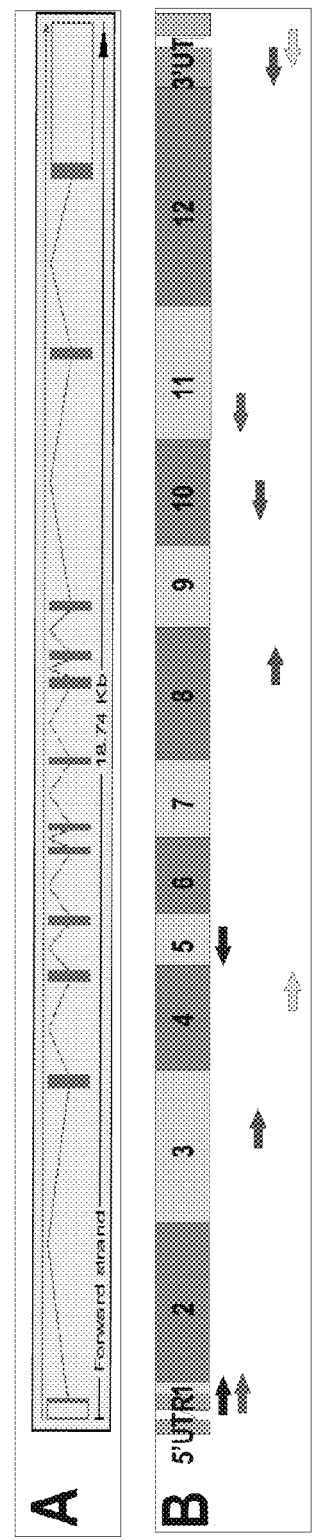
Figure 4:
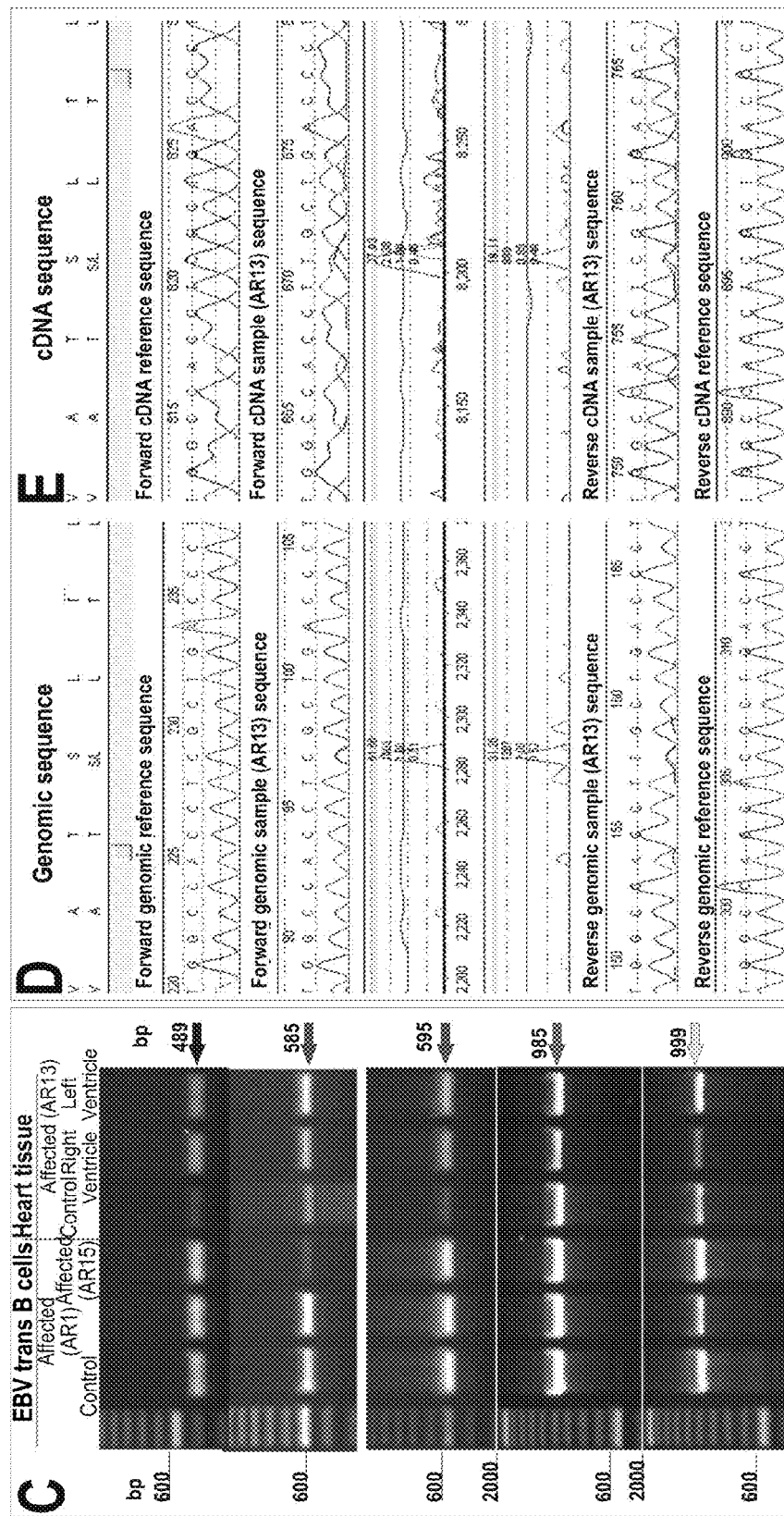
Figure 5:
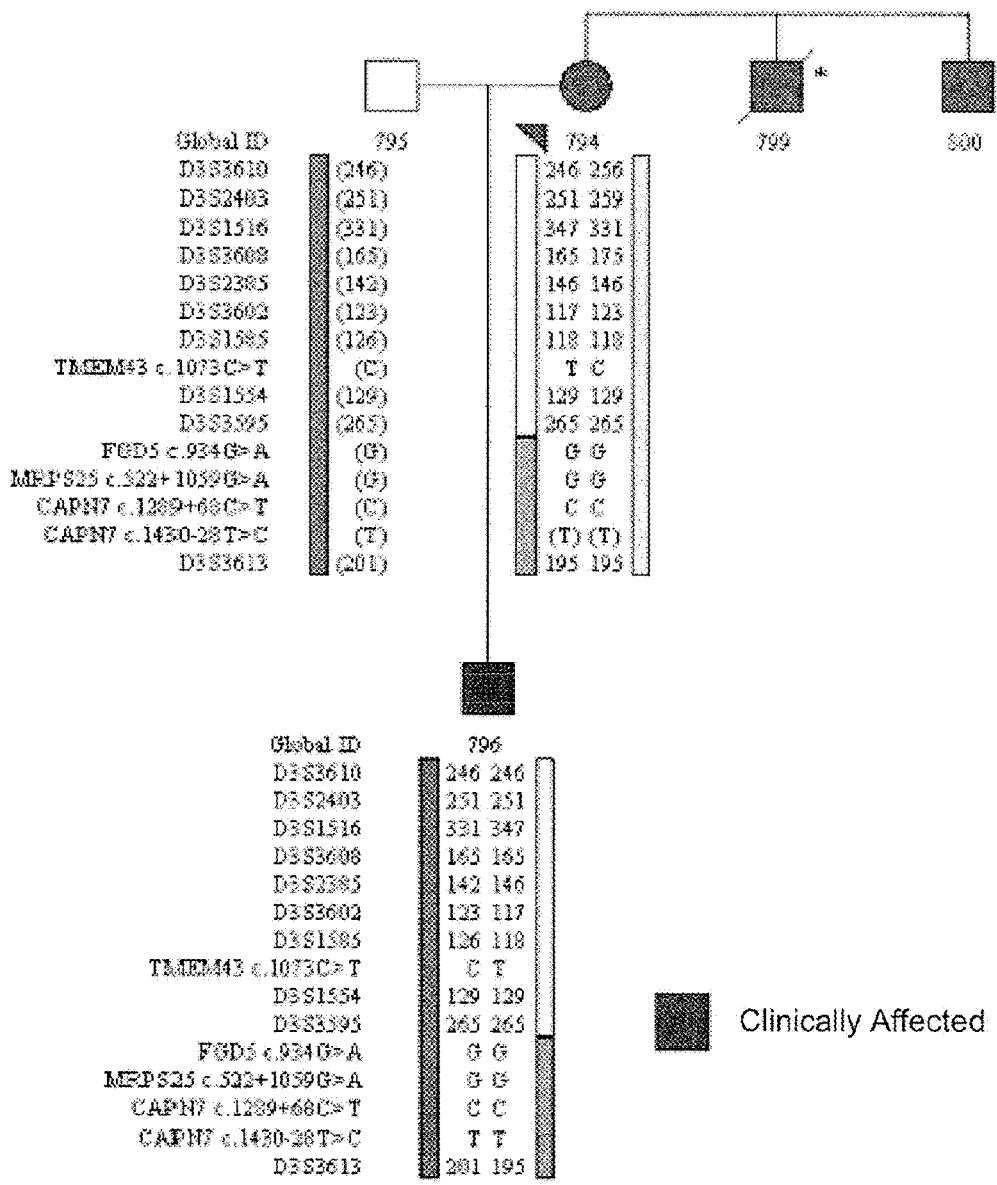
Figure 6:
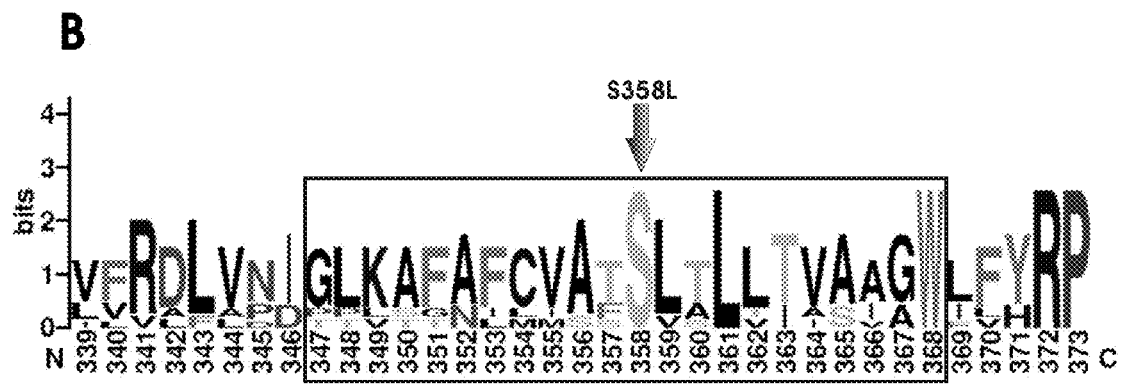

Transmembrane protein 43 (TMEM43, Genbank Accession number NM_024334) is a conserved gene, found across all eukaryotic and prokaryotic species (FIG. 6). The longest isoform has 12 exons producing a 400 amino acid protein (FIGS. 4A&B) that is 98% similar to the mouse protein (FIG. 6A). The TMEM43 transcript is expressed in white blood cells and heart tissue (FIG. 4C). The cDNA from the heart muscle of an affected subject was the full-length transcript, unaltered as determined by size fraction analysis and direct sequencing, suggesting that TMEM43 1073 C>T does not affect splicing (FIGS. 4C, D&E).

Figure 7:
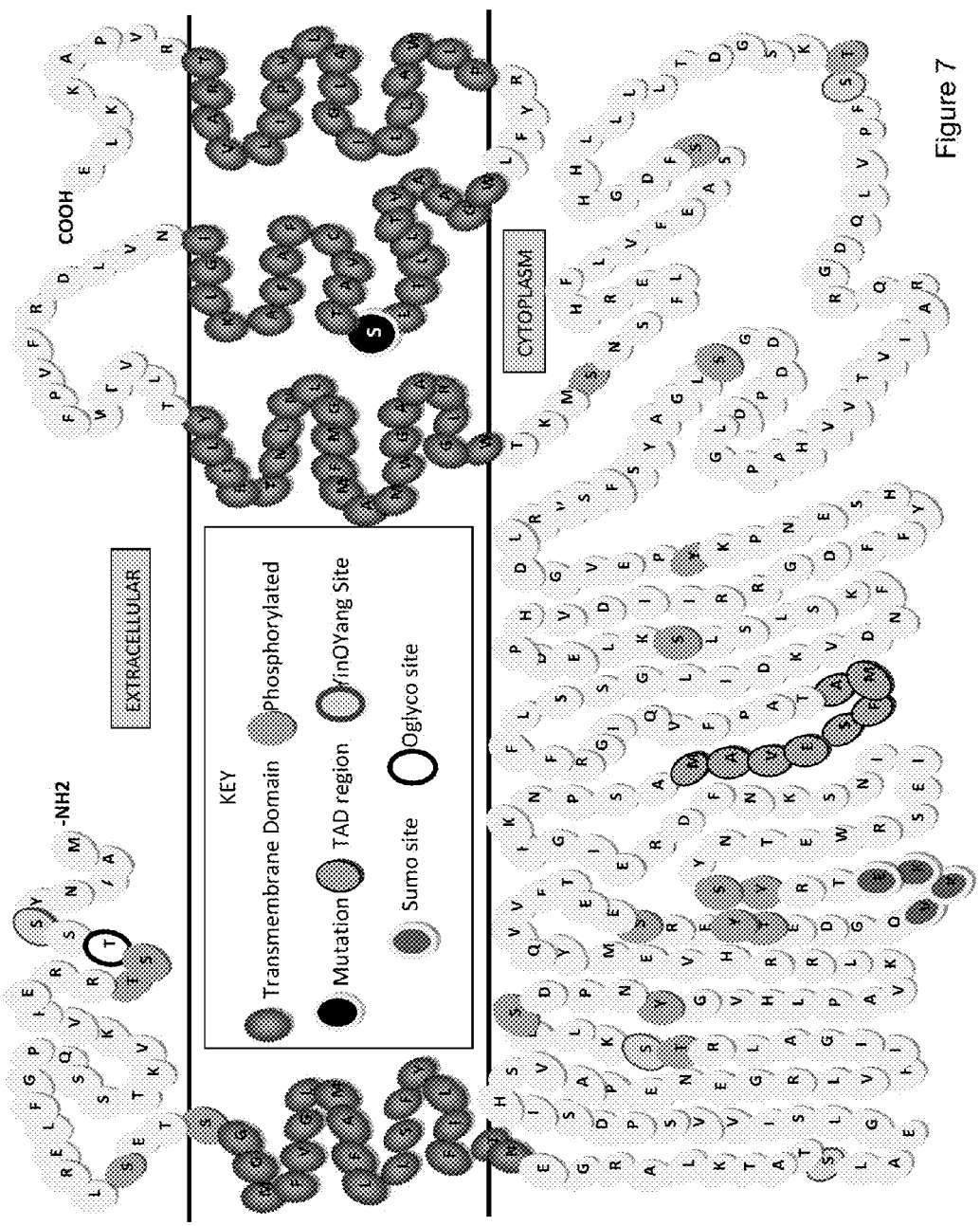

Bioinformatic analysis of the amino acid sequence of TMEM43 predicts it to be a cytoplasmic membrane protein with a number of potential post-translation modification sites (FIG. 7). The mutation (S358L) occurs within the third predicted transmembrane domain that is highly conserved in mammals, avian, amphibian, aquatic and insect orthologs (FIGS. 6A&B, FIG. 7). Interestingly, a leucine is tolerated in the bacterium *Rhizobium loti* but it is not found in any multicellular organisms (FIG. 6A). The S358L mutation is predicted to be deleterious (FIG. 6B, Table 4) but relatively little is known about the function of TMEM43.

TABLE 4

Prediction of the TMEM43 1073 C > T (S358L) mutation
effect by five different bioinformatic programs.

| | Method | | | | |
|---|---|---|---|---|---|
| Mutation | SIFT | Panther | PolyPhen | SNPs3D | PMut |
| S358L | deleterious | deleterious | benign | deleterious | deleterious |

Note:
Sequence homology for PolyPhen analyses was calculated with alignments of orthologs from Eukaryota and bacteria TMEM43 Mutation Screening in Extended ARVD5 Family Members Genomic DNA was sequenced from all available extended family members across the 15 ARVC families for the presence of the TMEM43 variant. All subjects at a priori 50% risk with primary or secondary affection status (n=106) were mutation carriers. Twenty-six subjects (3 male, 23 female) at a priori 50% risk who were clinically unaffected were mutation carriers as well. Median age of the males was 22 years, and for females 33 years: the absence of clinical signs is presumably due to age and sex dependent penetrance. The remaining 151 subjects at a priori 50% risk with no clinical signs who did not have the TMEM43 variant were considered unaffected. All subjects at less than a priori 50% risk (n=83) were also screened. Two subjects at a priori 25% risk had the TMEM43 variant. All spouses (n=47) were negative for the TMEM43 variant (FIG. 2).

Clinical Assessment of ARVD5 Kindreds

Pathology

Thirty-nine autopsy reports were available. Of these, 18 were reviewed from deceased males (median age 30 years—range 25-56; mean heart weight=500 g) from family AR1 who died suddenly. Fifteen of these reported on right ventricular histology, 11 had fibro-fatty replacement of the myocardium and the remaining four showed primarily fibrotic changes (FIG. 1B). No subject had critical coronary artery disease. For the 14 additional ARVD5 families 21 autopsy reports were reviewed, 17 males—median age 36.5 years (range 19-72) and 4 females—median age 52.5 years (range 36-65) were available. Mean heart weight was 525 g. Seven cases mentioned right ventricular histology all of which noted fibro-fatty replacement.

12-Lead ECG

Data on a total of 297 subjects (167 affected, 130 unaffected) that had at least one 12-lead surface ECG was available. The most prevalent features were poor R wave progression (PRWP), the presence of PVC's, and extended QRS 0.110 ms (Table 2). T wave inversion in leads V2-V3, and epsilon waves were noted in 3% of affected subjects. Of the 90 affected (35%), and 21 unaffected (14%) subjects with no ECG available for analysis, 73 affected and 2 unaffected were dead, the remaining subjects are in progress.

TABLE 2

12 lead ECG, Holter and Echocardiographic manifestations present on first
ECG, first Holter and first echocardiogram in subjects from 15 families with ARVC due to a
mutation in TMEM43 on chromosome 3

| | Affected | | | Unaffected | | | | |
|---|---|---|---|---|---|---|---|---|
| Sex | Male | Female | Tot. | Male | Female | Tot. | X2 | X2 |
| | 12 lead ECG | | | | | | | |
| N | 78 | 89 | 167 | 64 | 66 | 130 | Aff. Mv. | Aff. Fv. |
| Mean Age | 30 | 37.7 | | 33.1 | 38.2 | | Unaff. M | Unaff. F |

TABLE 2-continued 12 lead ECG, Holter and Echocardiographic manifestations present on first ECG, first Holter and first echocardiogram in subjects from 15 families with ARVC due to a mutation in TMEM43 on chromosome 3

| Sex | Affected | | | | | Unaffected | | | | | X2 | X2 |
|---|---|---|---|---|---|---|---|---|---|---|---|---|
| | Male | | Female | | Tot. | Male | | Female | | Tot. | | |
| SD | 12.1 | | 15.8 | | | 16 | | 13.2 | | | | |
| | n | % | n | % | N (%) | n | % | n | % | N (%) | | |
| PRWP | 23 | 30 | 25 | 28 | 48 (28.7) | 0 | 0 | 2 | 3 | 2 (1.5) | P ≤ 0.001 | P ≤ 0.001 |
| PVCs | 25 | 32 | 22 | 25 | 47 (28.1) | 0 | 0 | 1 | 2 | 1 (0.7) | p ≤ 0.001 | p ≤ 0.001 |
| QRS>110 | 25 | 32 | 8 | 9 | 33 (19.8) | 4 | 6 | 2 | 3 | 6 (4.6) | p ≤ 0.001 | p ≤ 0.2 ns |
| Septal Q | 10 | 13 | 14 | 16 | 24 (14.4) | 0 | 0 | 0 | 0 | 0 | p ≤ 0.01 | p ≤ 0.001 |
| Holter Monitor | | | | | | | | | | | | |
| N | 67 | | 79 | | 146 | 49 | | 44 | | 93 | Aff. Mv. Unaff. M | Aff. Fv. Unaff.F |
| Mean Age | 31.1 | | 37.7 | | | 33.1 | | 38.2 | | | | |
| SD | 13.3 | | 15.5 | | | 15.9 | | 12.8 | | | | |
| | n | % | n | % | N (%) | n | % | n | % | N (%) | | |
| PVCs ≥200/ 24 hours | 47 | 70 | 47 | 59 | 94 (64.4) | 0 | 0 | 1 | 2.3 | 1.0 | P < 0.001 | P < 0.001 |
| PVCs ≥1000/ 24 hours | 45 | 67 | 37 | 47 | 82 (56.2) | 0 | 0 | 1 | 2.3 | 1.0 | P < 0.001 | P < 0.001 |
| ≥1 run ns VT | 13 | 19 | 18 | 23 | 31 (21.2) | 0 | 0 | 0 | 0.0 | 0.0 | P < 0.01 | P < 0.001 |
| Echocardiograph | | | | | | | | | | | | |
| N | 67 | | 76 | | 143 | 50 | | 51 | | 101 | Aff. Mv. Unaff. M | Aff. Fv. Unaff.F |
| Mean Age | 31.58 | | 39.61 | | | 32.46 | | 38.27 | | | | |
| SD | 13.15 | | 15.14 | | | 14.91 | | 13.28 | | | | |
| | n | % | n | % | N (%) | n | % | n | % | N (%) | | |
| LVE > 2SD | 35 | 52 | 27 | 20 | 62 (43.3) | 10 | 20 | 4 | 8 | 14 (13.9) | P < 0.001 | P < 0.001 |
| LVE > 3SD | 24 | 4 | 20 | 13 | 44 (30.8) | 4 | 8 | 2 | 4 | 6 (5.9) | P < 0.001 | P < 0.001 |
| FS <30% | 24 | 36 | 17 | 22 | 41 (28.7) | 5 | 10 | 4 | 8 | 9 (8.9) | P < 0.01 | P < 0.05 |
| Wall motion | 18 | 27 | 15 | 20 | 33 (23.1) | 2 | 4 | 0 | 0 | 2 (1.9) | P < 0.01 | P < 0.001 |
| LAE | 16 | 24 | 8 | 10 | 24 (16.8) | 4 | 8 | 3 | 6 | 7 (6.9) | P < 0.025 | P < 1 ns |

PVC: premature ventricular complex,
VT: Ventricular tachycardia,
PRWP: poor R wave progression defined as V3 less than 3 mm
[32]LVE: Left ventricular enlargement indexed to height and weight
[18,19]LAE: left atrial enlargement,
FS: fractional shortening,
M: males,
F: females.

The assessment included the following features all of which were at a frequency of less than 10% in affected subjects: first degree AV block, T wave inversion in V2 and V3, ST depression anterior, lateral and inferior, ST elevation anterior, lateral and inferior, epsilon waves, tall R wave in V2, V3, left bundle branch block, right bundle branch block, flat/inferior/inverted lateral T waves, short PR interval, long and short QT interval, Inferior, lateral and anterior Q waves, atrial fibrillation, left atrial enlargement, right ventricular enlargement, left anterior and posterior hemiblock, left axis, FS <20% and left ventricular hypertrophy.

Holter Monitor

Figure 8:
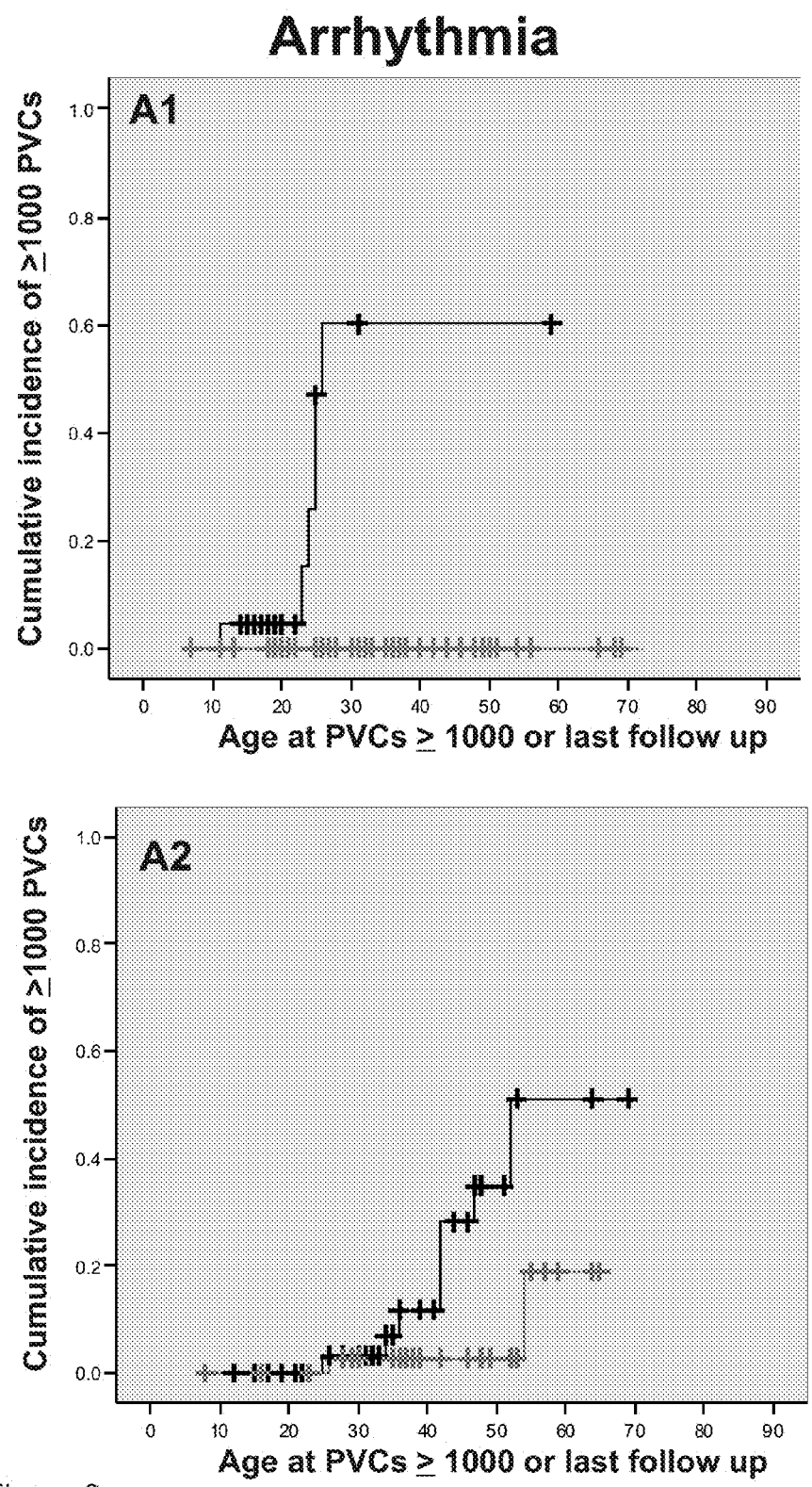
Figure 8:
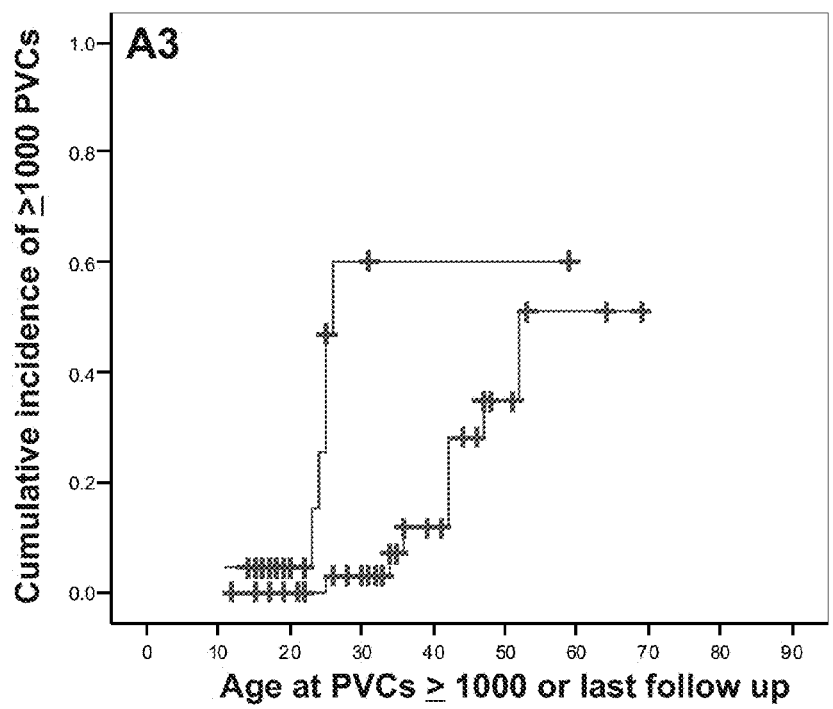
Figure 8:
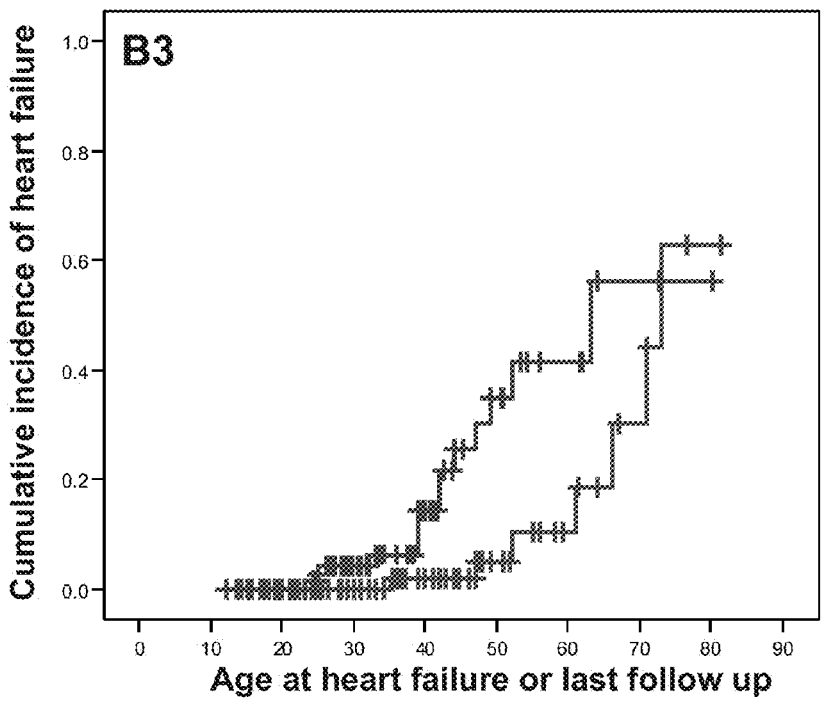
Figure 8:
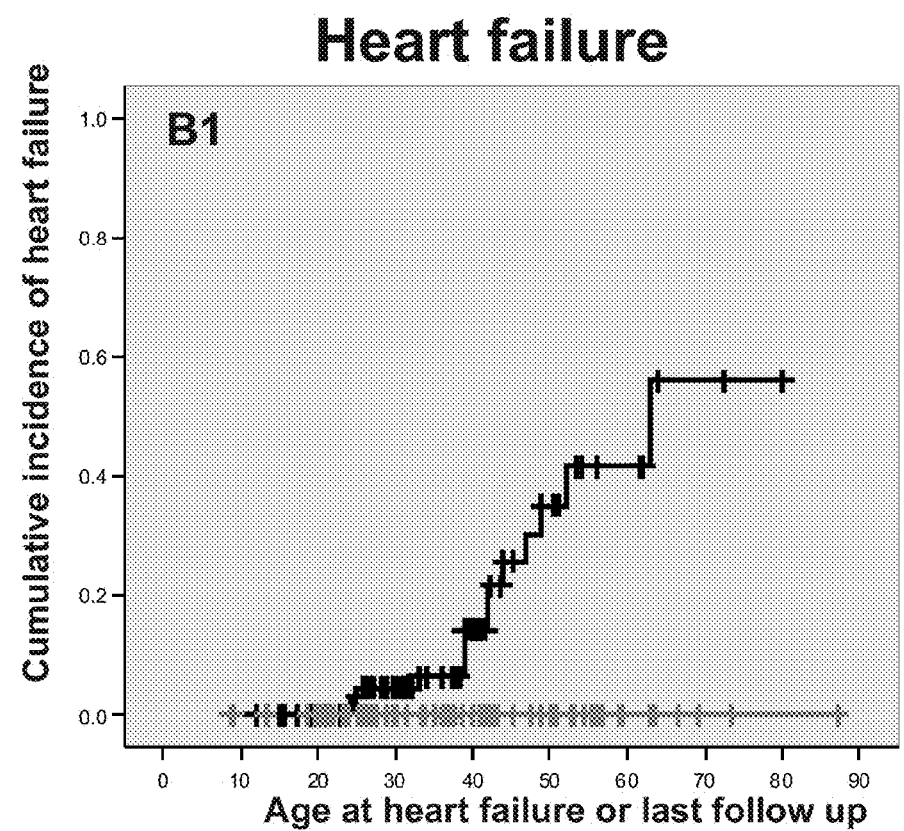
Figure 8:
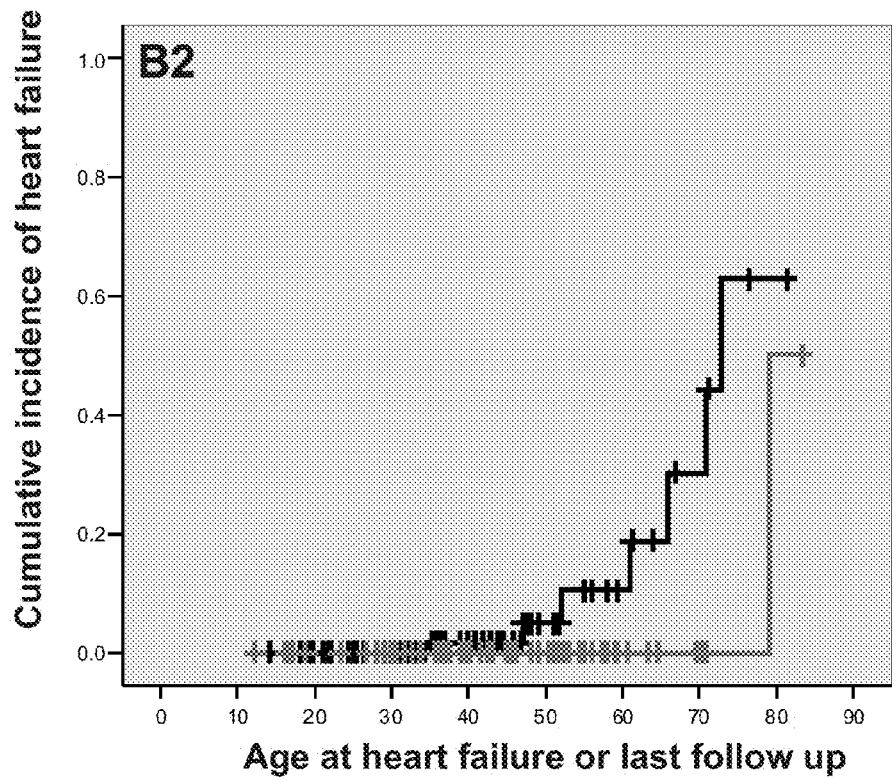
Figure 8:
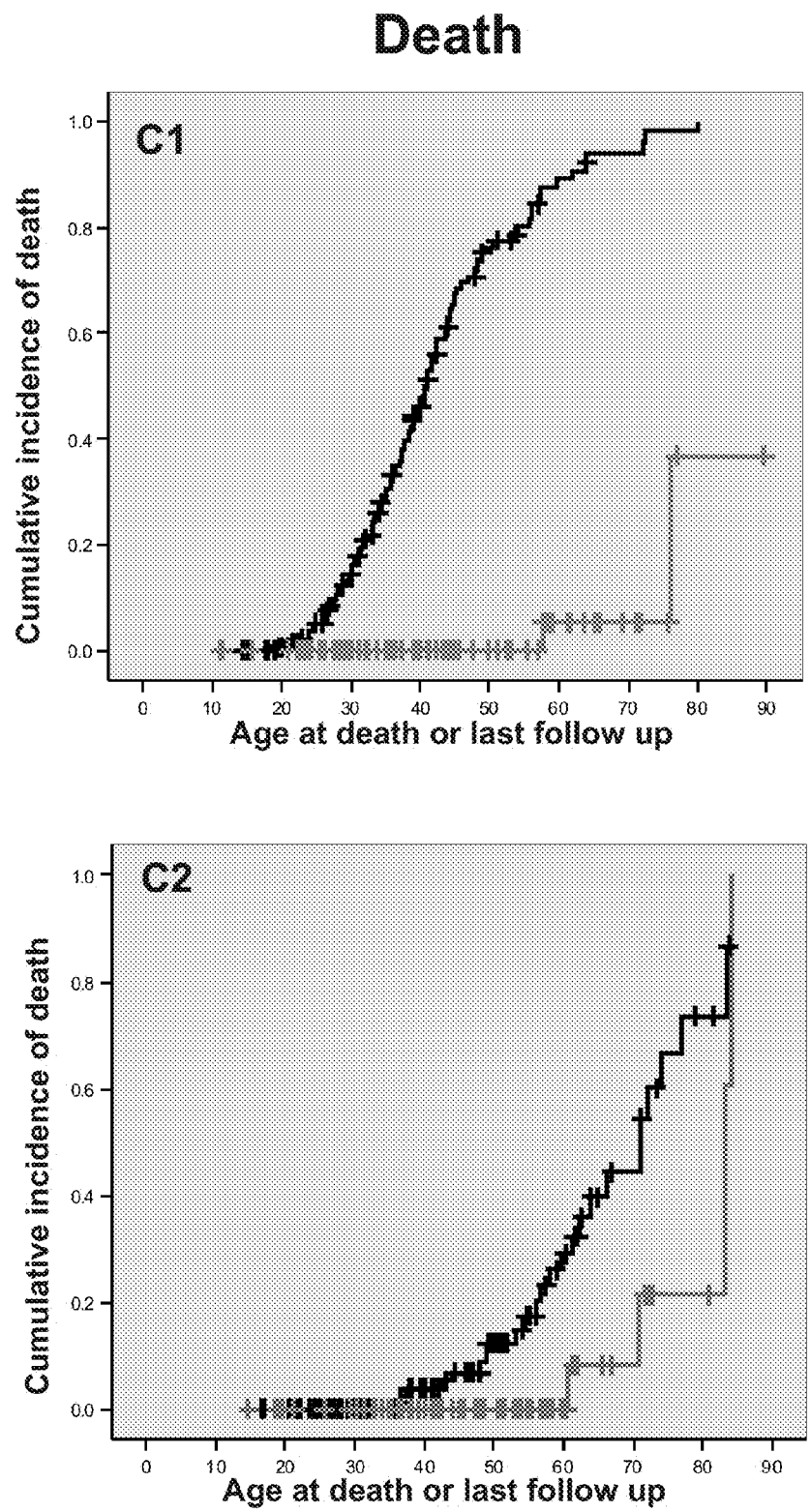
Figure 8:
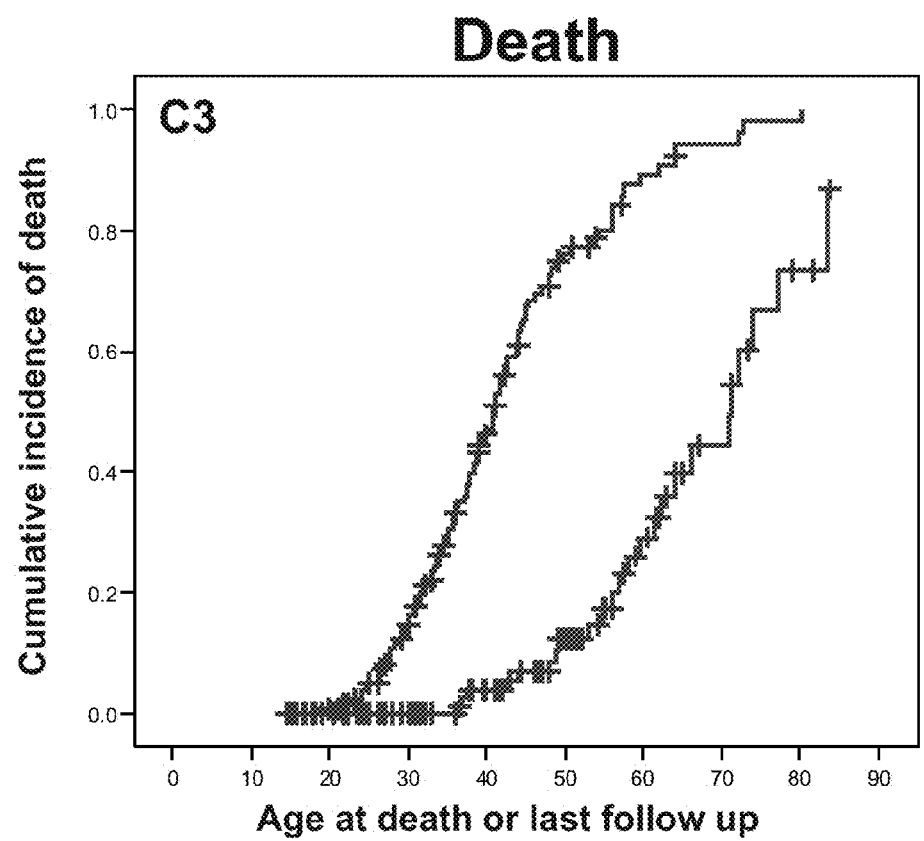

Of the 239 subjects (146 affected, 93 unaffected) with at least one Holter Monitor report, the most prevalent features were premature ventricular contractions (PVC's) ≥200 and ≥1000 in 24 hours, and the presence of at least one run of non sustained ventricular tachycardia (nsVT) (Table 2). Of the 111 affected (43%), and 58 unaffected (38%) subjects with no Holter monitor available for analysis, 76 affected and 2 unaffected were dead. The remaining subjects are in progress. Eighty-two affected subjects (56%: 45 male, 37 female) were determined to have ≥1000 PVC's on baseline Holter monitor (Table 2). Fifteen affected subjects (43%: six male, eight female) without ≥1000 PVC's at baseline subsequently developed ≥1000 PVC's (FIGS. 8A1&A2). One unaffected subject had ≥1000 PVC's at baseline (Table 2): two females developed ≥1000 PVC's on a subsequent Holter monitor (FIG. 8A2). The median age to onset of de-novo ≥1000 PVC's for affected males was 26 years. There was a significant difference between affected and unaffected males for time to development of ≥1000 PVC's (p≤0.0001) (FIG. 8A1). The median age to onset of de-novo ≥1000 PVC's for females in the affected group was 56 years with a significant difference between affected and unaffected females for time to development of ≥1000 PVC's (p=0.02, RR 5.9, 95% CI 1.2-28.5) (FIG. 8A2). Affected males were five times more likely to develop ≥1000 PVC's than affected females (RR 5.467, (95% CI 1.769-16.889) p≤0.003) (FIG. 8A3).

Echocardiography

Of the 244 subjects (143 affected and 101 unaffected) that had at least one 2D echocardiogram available for analysis. Five reports (three males, two females) from affected subjects were excluded because measurements were not available. Of these, three males and one female, all deceased, were reported to have a "massively dilated heart". The most prevalent feature was LVE based on LVEDD (Table 2) 19. Of the 114 (44%) affected, and 50 unaffected (33%) subjects with no echocardiogram, 86 affected and two unaffected were dead. The remaining subjects are in progress. Right ventricular echocardiography was unavailable for many echocardiograms from older subjects.

Heart Failure

Of 89 affected males with medical records, 14 developed heart failure at a median age of 63 years (95% CI 41 years-84 years) compared with none of the unaffected males (p≤0.0001: log rank) (FIG. 8B1). Of 87 affected females with medical records, seven developed heart failure (median age 73 years, 95% CI 69 years-77 years), and one unaffected female at age 79 years (p≤0.001, log rank) (FIG. 8B2). Affected males were three times more likely to develop heart failure than females (RR 3.4, 95% CI 1.36-8.57, p≤0.009) (FIG. 8B3).

Life Expectancy

In the affected group (n=257) there were 123 (48%) deaths (99 males and 24 females). DNA was available from 10 deceased subjects, the remainder (n=113) made up the primary affection status group for whom no DNA was available (FIG. 2). Sudden cardiac death occurred in 85 (86%) of the 99 males and 10 (42%) of the 24 females. Death was attributed to other cardiac causes in 14 (11%) subjects, (seven male, seven female) and non-cardiac conditions in seven (5%) subjects, three male and four female. For the remaining four deaths (two male, two female) the cause of death was unknown. The median survival was 41 years for affected males (95% CI 38 years-43 years) compared with a mean age of 83 years in unaffected males (p≤0.0001, log rank) (FIG. 8C1). The median survival was 71 years for affected females (95% C.I. 64 years-78 years), compared with a median age of 83 years for unaffected females (95% CI 65 years-101 years) (FIG. 8C2). The relative risk of dying was 6.8 times higher in affected males compared to affected females (95% C.I:4.3 10.9, p≤0.0001) (FIG. 8C3).

Discussion

The inventors have identified a mutation in TMEM43, as the cause of ARVC at locus ARVD5. Screening across 15 ARVD5-linked families for the S358L mutation show all subjects with primary affection status are heterozygous carriers, and the mutation was not detected in any population-based controls. This clearly is another Newfoundland founder mutation.[20] In addition, the serine at position 358 is well conserved across multicellular eukaryotic species and the effect of the amino acid change is predicted to be deleterious.

Without wishing to be bound by theory, mutations in desmosomal genes have been implicated in several genetic subtypes of ARVC, indicating that ARVC is primarily a disease of the desmosome.[5, 7] Mechanical stress has, therefore, been predicted to cause the ARVC phenotype. More recently signaling pathways have been implicated in ARVC pathogenesis[7, 21] For example, plakoglobin, when freed from desmosomal complexes, translocates to the nucleus where it competes and opposes the action of β-catenin to down regulate the canonical Wnt/β-catenin signaling pathway, which in turn promotes adipogenesis, fibrogenesis and apoptosis.[5, 21] Suppression of the canonical Wnt/β-catenin signaling has been shown to up regulate two adipogenic transcription factors, C/EBP-α and PPARγ.[21]

In the case of ARVD5, the inventors have identified a gene that is highly conserved across animal phyla for which functional domains with known proteins yields no information to potential biochemical pathways. Interestingly, a genome wide scan for peroxisome proliferator response elements (PPREs) identified 1085 potential target genes of PPARγ, including TMEM43[22]. While the function of the TMEM43 protein is not well understood, and to date, it has not been associated with any known disease, TMEM43 appears to be regulated by PPARγ.

The inventors have defined ARVC at locus ARVD5 across at least eight generations from fifteen families. The phenotype included fibrofatty infiltration of both left and right ventricles, manifestations of arrhythmogenic disease and early death. The inventors showed that the arrhythmias were the earliest manifestation, followed by death. Heart failure occurred later in those who survived or experienced less ectopy. Subjects had LVE, with systolic manifestations, which lead in some instances to heart failure. This condition is alternatively called "arrhythmic cardiomyopathy."[23, 24, 25] ARVC was difficult to diagnose prior to the present disclosure.[1] A problem with prior approaches is that there has to be access to the relevant clinical testing, the subject needs to be alive, and a large enough family present to recognize disease despite variable expression and reduced penetrance. Although modifications to these criteria have been proposed[26] the continued reliance on multiple testing made diagnosis problematic in the prior art. The ability to define those with the gene, by molecular testing, presymptomatically (particularly as the first symptom may be SCD) now removes the uncertainly surrounding false negative clinical assessment, and allows for prophylactic treatment with ICD therapy.

Common diseases are those that most physicians will encounter in their practice over their lifetime. As a practical definition, Motulsky set a frequency of 1 affected per 1000 for a given disease to be considered common.[27] ARVC clearly approaches the frequency of a common disease in Newfoundland Labrador and a population-based approach for molecular genetic testing to identify individuals at risk of SCD is being considered. The high morbidity and mortality associated with the mutation in TMEM43 would be reduced by screening for ARVC.[28]

Many medically important genes and mutations have been identified in patients and families from Newfoundland that are relevant to outbred populations. For example, the role of mismatch repair genes in colon cancer, a universal phenomenon, was discovered by genetic mapping in a multigenerational family from Newfoundland (33-34). The identification of multiple Newfoundland families with a rare, multisystem genetic disorder, Bardet-Biedl syndrome (BBS), included the mapping of a novel BBS gene (BBS5) and inspired a new medical field of inquiry, one of ciliary disease, involved in more common conditions (35-39). Hearing loss is the most common sensory disorder worldwide. A missense mutation in exon 8 of the WFS1 gene was first identified in a Newfoundland family with low frequency hearing loss (39). Since this report, missense mutations in the WFS1 gene have been found to underlie all reported cases for this type of hearing deficit except one (Costa Rican family) (40-41). These are but a few of many examples that both genes and specific mutations identified in patients and families with genetic disease from Newfoundland serve as a valuable resource for out bred populations. The Newfoundland founder population also has generalizability for more common (complex diseases). In a recent study of the genetic architecture of 12 of the worlds well established founder populations, the Newfoundland population was found to have the greatest generalizability of the founder populations, as all markers with an allele frequency greater than 10% in the NL population were also noted in a Caucasian out bred population (42).

The methods disclosed provide significant advantages because it they are based on a homogeneous population with almost total ascertainment of those at a priori 50% risk in the defined pedigrees. All the available past medical records from affected and unaffected subjects were examined, extensive genealogical data across multiple generations, and subjects are clinically screened at a single tertiary centre. An accurate knowledge of the disease process provides a basis for precise genetic counseling and clinical care of those at-risk. The TMEM43 mutations were made with a large and homogeneous ARVC population, which is well demarcated and well ascertained.

Example 2

ARVC Penetrance

Figure 12:
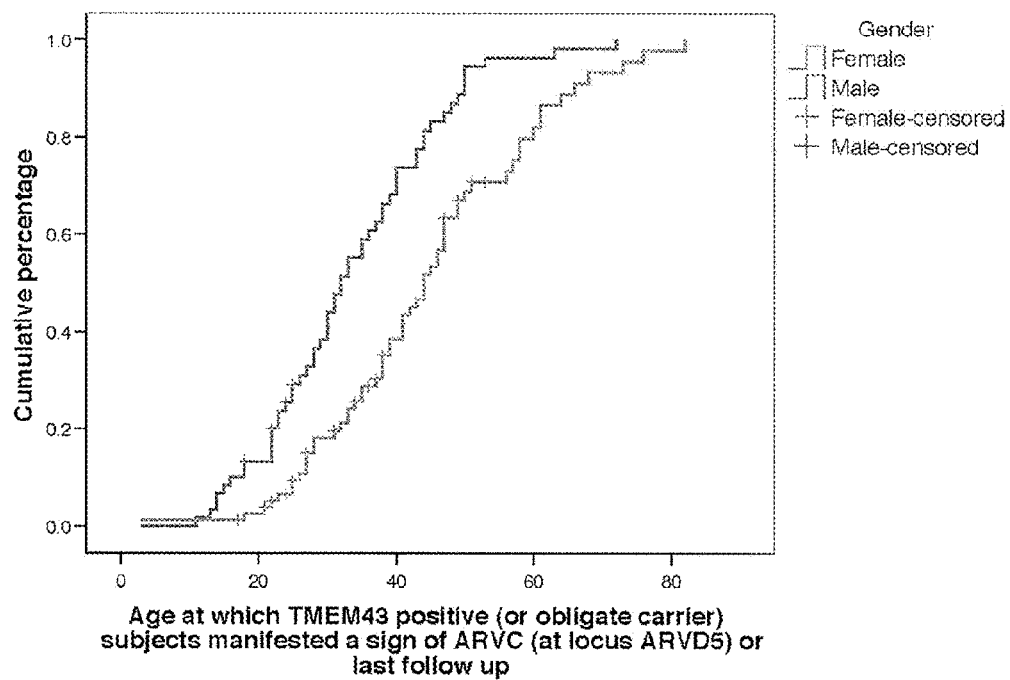
FIG. 12 is a graph (A) and table (B) showing age penetrance of TMEM43 positive subjects.

One hundred and thirty seven subjects (60 affected males, 77 affected females) were used to determine penetrance. Median age to develop an ARVD5 associated phenotype was 32 years (95% CI 28-35) for males and 44 years (95% CI 39-48) for females, with 100% of males and females penetrant by 63 and 76 years respectively (FIGS. 12A and B). Males were twice as likely to reveal the disease phenotype than females (RR 2, 99% CI 1.2-3.3) (p≤0.0001). The commonest clinical features for which subjects were initially penetrant were ectopy (44%), and LVE (27%), then VT (9%), QRS >110 ms (9%), late potentials on SAECG (7%), SCD (2%) and heart failure (2%).

For the penetrance study, subjects who were alive at the start of the study (1996), who had a medical record and had a genetic diagnosis (mutation carriers or obligate carriers) were followed. The results showed that ARVC was fully penetrant in males by the age of 63 and in females by the age of 76; ectopy and LVE were often the first presenting features, and few presented with death or heart failure. Therefore, in order to assess the penetrance of heart failure and death, all affected subjects were used. Heart failure and death were morbid outcomes at early ages in both males and females, with far more serious early events in males. In both sexes heart failure occurs as a later manifestation in subjects who did not succumb to SCD. These major manifestations define ARVC, due to the TMEM43 mutation, as a lethal, fully penetrant, sex-influenced, autosomal dominant disorder.

Example 3

Subjects and/or families which have a family history of suspected ARVD/C eg a family history of cardiomyopathy and sudden cardiac death are identified. Blood samples from $1^{st}$, $2^{nd}$ and third degree relatives of the affected subjects are obtained. One or more TMEM43 exons or parts thereof are sequenced and compared to normal subjects to identify putative mutations. The frequency and association of putative mutations in affected and control populations is determined, for example by assembling a pedigree. Mutations are confirmed, for example confirmed to be rare in a normal or non-ARVD/C population.

Example 4

TMEM43 transcripts identified by ECgene bioinformatic analysis are useful for designing probes and primers for use in the methods described herein.
>H3C1779.1 2,846 bp. Direction:F CDS(259 . . . 1,459)
>H3C1779.1 (SEQ ID NOS: 55 & 56)
>H3C1779.2 (SEQ ID NOS: 57 & 58)
>H3C1779.3 (SEQ ID NOS: 59 & 60)
>H3C1779.4 (SEQ ID NOS: 61 & 62)
>H3C1779.5 (SEQ ID NOS: 63 & 64)
>H3C1779.6 (SEQ ID NOS: 65 & 66)
>H3C1779.7 (SEQ ID NOS: 67 & 68)
>H3C1779.8 (SEQ ID NOS: 69 & 70)
>H3C1779.9 (SEQ ID NOS: 71 & 72)
>H3C1779.10 (SEQ ID NOS: 73 & 74)
>H3C1779.11 (SEQ ID NOS: 75 & 76)

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety

FULL CITATIONS FOR REFERENCES REFERRED TO IN THE SPECIFICATION

1. McKenna W J, Thiene G, Nava A, et al. Diagnosis of arrhythmogenic right ventricular dysplasia/cardiomyopathy. Task Force of the Working Group Myocardial and Pericardial disease of the European Society of Cardiology and the Scientific Council on Cardiomyopathies of the International Society and Federation of Cardiology. British Heart Journal 1994; 71:215-218.
2. Fontaine G, Fontaliran F, Frank R. Arrhythmogenic right ventricular cardiomyopathies. clinical forms and main differential diagnoses. Circulation 1998; 97:1532-1535.
3. Heuser A, Plovie E R, Ellinor P T, et al. Mutant Desmocollin-2 Causes Arrhythmogenic Right Ventricular Cardiomyopathy. Am J Hum Genet 2006; 79:1081-1088.
4. Pilichou K, Nava A, Basso C, et al. Mutations in Desmoglein-2 Gene Are Associated With Arrhythmogenic Right Ventricular Cardiomyopathy 10.1161/CIRCULATIONAHA.105.583674. Circulation 2006; 113:1171-1179.
5. Sen-Chowdhry S, Syrris P, McKenna W. Genetics of right ventricular cardiomyopathy. J Cardiovasc Electrophysiol 2005; 16:927-35.
6. Dokuparti M V, Pamuru P R, Thakkar B, Tanjore R R, Nallari P. Etiopathogenesis of arrhythmogenic right ventricular cardiomyopathy. J Hum Genet 2005; 50:375-81.

7. MacRae C A, Birchmeier W, Thierfelder L. Arrhythmogenic right ventricular cardiomyopathy: moving toward mechanism. J Clin Invest 2006; 116:1825-8.
8. Ahmad F, Li D, Karibe A, et al. Localisation of a gene responsible for arrhythmogenic right ventricular dysplasia to chromosome 3p23. Circulation 1998; 98:2791-2795.
9. Hodgkinson K, Parfrey P, Bassett A, et al. The impact of implantable cardioverter defibrillator therapy on survival in autosomal dominant arrhythmogenic right ventricular cardiomyopathy (ARVD5). The Journal of the American College of Cardiology 2005; 45:400-408.
10. Crooks G E, Hon G, Chandonia J M, Brenner S E. WebLogo: a sequence logo generator. Genome Res 2004; 14:1188-90.
11. Combet C, Blanchet C, Geourjon C, Deleage G. NPS@: network protein sequence analysis. Trends Biochem Sci 2000; 25:147-50.
12. Gasteiger E, Gattiker A, Hoogland C, Ivanyi I, Appel R D, Bairoch A. ExPASy: The proteomics server for in-depth protein knowledge and analysis. Nucleic Acids Res 2003; 31:3784-8.
13. Ramensky V, Bork P, Sunyaev S. Human non-synonymous SNPs: server and survey. Nucleic Acids Res 2002; 30:3894-900.
14. Ng P C, Henikoff S. Accounting for human polymorphisms predicted to affect protein function. Genome Res 2002; 12:436-46.
15. Thomas P D, Kejariwal A, Campbell M J, et al. PANTHER: a browsable database of gene products organized by biological function, using curated protein family and subfamily classification. Nucleic Acids Res 2003; 31:334-41.
16. Yue P, Melamud E, Moult J. SNPs3D: candidate gene and SNP selection for association studies. BMC Bioinformatics 2006; 7:166.
17. Ferrer-Costa C, Gelpi J L, Zamakola L, Parraga I, de la Cruz X, Orozco M. PMUT: a web-based tool for the annotation of pathological mutations on proteins. Bioinformatics 2005; 21:3176-8.
18. Henry W L, Gardin J M, Ware J H. Echocardiographic Measurements in Normal Subjects from Infancy to Old Age. Circulation 1980; 62:1054-1061.
19. Henry W L, Ware J, Gardin J M, Hepner S I, McKay J, Weiner M. Echocardiographic measurements in normal subjects. Growth related changes that occur between infancy and early adulthood. Circulation 1978; 57:278-285.
20. Rahman P, Jones A, Curtis J, et al. The Newfoundland population: a unique resource for genetic investigation of complex diseases. Hum. Mol. Genet. 2003; 12:167R-172.
21. Garcia-Gras E, Lombardi R, Giocondo M J, et al. Suppression of canonical Wnt/beta-catenin signaling by nuclear plakoglobin recapitulates phenotype of arrhythmogenic right ventricular cardiomyopathy. J Clin Invest 2006; 116:2012-21.
22. Lemay D G, Hwang D H. Genome-wide identification of peroxisome proliferator response elements using integrated computational genomics. J Lipid Res 2006; 47:1583-7.
23. Pinamonti B, Pagnan L, Bussani R, Ricci C, Silvestri F, Camerini F. Right Ventricular Dysplasia With Biventricular Involvement. Circulation 1998; 98:1943-1945.
24. Norman M, Simpson M, Mogensen J, et al. Novel Mutation in Desmoplakin Causes Arrhythmogenic Left Ventricular Cardiomyopathy 10.1161/CIRCULATIONAHA.104.532234. Circulation 2005; 112:636-642.
25. Sen-Chowdhry S, Syrris P, Ward D, Asimaki A, Sevdalis E, McKenna W. Clinical and genetic characterization of families with arrhythmogenic right ventricular dysplasia/cardiomyopathy provides novel insights into patterns of disease expression. Circulation 2007; 115:1710-20.
26. Hamid M S, Norman M, Quraishi A, et al. Prospective Evaluation of Relatives for Familal Arrhythmogenic Right Ventricular Cardiomyopathy/Dysplasia Reveals a Need to Broaden Diagnostic Criteria. Journal of the American College of Cardiology 2002; 40:1445-1450
27. King R A, Rotter J I, Motulsky A G. The Genetic Basis of Common Diseases. Oxford: Oxford University Press, 2002:1096.
28. Pullman D, Hodgkinson K. Genetic knowledge and moral responsibility: ethical concerns at the interface of genetic research and clinical practice. Clinical Genetics 2006; 69:199-203.
29. Syrris P, Ward D, Asimaki A, et al. Clinical Expression of Plakophilin-2 Mutations in Familial Arrhythmogenic Right Ventricular Cardiomyopathy 10.1161/CIRCULATIONAHA.105.561654. Circulation 2006; 113:356-364.
30. Syrris P, Ward D, Asimaki A, et al. Desmoglein-2 mutations in arrhythmogenic right ventricular cardiomyopathy: a genotype-phenotype characterization of familial disease 10.1093/eurheartj/eh1380. Eur Heart J 2007; 28:581-588.
31. Protonotarios N, Tsatsopoulou A, Anastasakis A, et al. Genotype-phenotype assessment in autosomal recessive arrhythmogenic right ventricular cardiomyopathy (Naxos disease) caused by a deletion in plakoglobin. Journal of the American College of Cardiology 2001; 38:1477-1484.
32. Gami A S, Holly T A, Rosenthal J E. Electrocardiographic poor R-wave progression: analysis of multiple criteria reveals little usefulness. American Heart Journal 2004; 148:80-85.
33. Papadopoulos, N. et al. Mutation of a mutL homolog in hereditary colon cancer. Science 263, 1625-9 (1994).
34. Green, R. C. et al. Hereditary nonpolyposis colon cancer: analysis of linkage to 2p15-16 places the COCA1 locus telomeric to D2S123 and reveals genetic heterogeneity in seven Canadian families. Am J Hum Genet 54, 1067-77 (1994).
35. Young T L, Penney L, Woods M O, Parfrey P S, Green J S, Hefferton D, Davidson W S (1999) A fifth locus for Bardet-Biedl syndrome maps to chromosome 2q31. Am J Hum Genet 64: 900-904
36. Young T L, Woods M O, Parfrey P S, Green J S, O'Leary E O, Hefferton D, Davidson W S (1998) Canadian Bardet-Biedl syndrome family reduces the critical region of BBS3 (3p) and presents with a variable phenotype. Am J Med Genet 78: 461-467
37. Woods M O, Young T L, Parfrey P S, Hefferton D, Green J S, Davidson W S (1999) Genetic heterogeneity of BBS in a distinct Canadian population: Evidence for a fifth locus. Genomics 55: 2-9.
38. Li, J B et al. Comparative and basal genomics identifies a flagellar and basal body proteome that includes the BBS in human disease gene. Cell 117: 541-52, 2004. (Citations: 130).
39. Kulaga H M, Leitch C C, Eichers E R, Badano J L, Lesemann A, Hoskins B E, Lupski J R, Beales P L, Reed R R, Katsanis N. Loss of BBS proteins causes anosmia in humans and defects in olfactory cilia structure and function in the mouse. Nat Genet. 2004 September; 36(9):994-8. Epub 2004 Aug. 22.
40. Young T L, Ives E, Lynch E, Person R, Snook S, MacLaren L, Cator T, Griffin A, Fernandez B, Lee M K, King M C (2001) Non-syndromic progressive hearing loss DFNA38 is caused by heterozygous missense mutation in the Wolfram syndrome gene WFS1. Hum Mol Genet 10: 2509-14.
41. Cryns K, Sivakumaran T A, Van den Ouweland J M, Pennings R J, Cremers C W, Flothmann K, Young T L, Smith R J, Lesperance M M, Van Camp G. Mutational spectrum of the WFS1 gene in Wolfram syndrome, non-syndromic hearing impairment, diabetes mellitus, and psychiatric disease. Hum Mutat. 2003 October; 22(4):275-87.
42. Rahman P. Jones A. Curtis J. Bartlett S. Peddle L. Fernandez B. Freimer N. 2003. The Newfoundland population: a unique resource for genetic investigation of complex diseases. Hum. Mol. Genetics. 12(R2): R167-R172.
43. Dreger, M Bengtsson, L Schoneberg T, Otto H, and Hucho F; Nuclear envelope proteomics: novel integral membrane proteins of the inner nuclear membrane, 2001 PNAS 98:11943-11948.

We claim:

1. A composition comprising:
   (i) a polymerase reaction buffer and/or hybridization solution; and
   (ii) at least one isolated single stranded nucleic acid comprising at least 17 contiguous nucleotides of SEQ ID NO: 4 including the thymidine at position 171, or at least one isolated single stranded nucleic acid consisting of the sequence selected from the group consisting of SEQ ID NOS: 19, 20, 23, 24, 43, and 44; wherein the isolated nucleic acid is labeled with a detectable label selected from the group consisting of a fluorescent compound, a chemiluminescent (chromophore) compound, and an enzyme; and wherein the composition is used to detect a ARVD/C associated mutant TMEM43.

2. A microarray comprising a plurality of single stranded nucleic acid probes and a solid surface wherein the probes are fixed to the solid surface, wherein at least one of the plurality of probes comprises at least 17 contiguous nucleotides of SEQ ID NO: 4, including the thymidine at position 171, or the complement thereof.

3. A kit comprising instructions for use and one or more of:
   a) a nucleic acid detection reagent comprising:
      (i) at least one isolated nucleic acid probe comprising at least 17 contiguous nucleotides of SEQ ID NO: 4 including the thymidine at position 171, or the complement thereof;
      (ii) a carrier selected from the group consisting of agarose, cellulose, dextran, Sephadex, Sepharose, carboxymethyl cellulose polystyrine, filter paper, ion-exchange resin, plastic film, plastic tube, glass beads, polyamine-methyl vinyl-ether-maleic acid copolymer, amino acid copolymer, ethylene-maleic acid copolymer, nylon, and silk fixed to the at least one isolated nucleic acid probe in (i) or a detectable label selected from the group consisting of a fluorescent compound, a chemiluminescent (chromophore) compound, and an enzyme, wherein the isolated nucleic acid probe in (i) is labeled with the detectable label;
   b) the composition of claim 1;
   c) a microarray comprising a plurality of single stranded nucleic acid probes and a solid surface wherein the probes are fixed to the solid surface, wherein at least one of the plurality of probes comprises at least 17 contiguous nucleotides of SEQ ID NO: 4 including the thymidine at position 171; and
   d) one or more primers selected from SEQ ID NOS: 19, 20, 23, 24, 43, and 44 labeled with a detectable label selected from the group consisting of a fluorescent compound, a chemiluminescent (chromophore) compound, and an enzyme.

4. The kit of claim 3, wherein the one or more primers are selected from the group consisting of SEQ ID NOS: 19, 20, 23, 24, 43, and 44.

5. The kit of claim 3 further comprising an isolated nucleic acid probe that hybridizes with wildtype TMEM43, wherein the probe is labeled with a detectable label selected from the group consisting of a fluorescent compound, a chemiluminescent (chromophore) compound, and an enzyme.

6. The kit of claim 3 wherein the nucleic acid probe comprises 17-20 contiguous nucleotides of SEQ ID NO: 53.

7. The kit of claim 5 wherein the wildtype TMEM43 sequence consists of SEQ ID NO: 54.

8. A composition comprising at least one isolated deoxyribonucleic acid comprising at least 250 contiguous nucleotides of SEQ ID NO: 4, including the thymidine at position 171, or the complement thereof, wherein the isolated deoxyribonucleic acid is labeled with a detectable label selected from the group consisting of a fluorescent compound, a chemiluminescent (chromophore) compound, and an enzyme.

9. The composition of claim 1 wherein the composition comprises:
   (i) PCR buffer; and
   (ii) at least one isolated single stranded nucleic acid selected from the group consisting of SEQ ID NOS: 19, 20, 23, 24, 43, and 44 labeled with a detectable label selected from the group consisting of a fluorescent compound, a chemiluminescent (chromophore) compound, and an enzyme, wherein the composition is used to detect ARVD/C associated mutant TMEM43.

10. The composition of claim 1, wherein the composition comprises:
    (i) a hybridization solution; and
    (ii) at least one isolated single stranded nucleic acid comprising at least 17 contiguous nucleotides of SEQ ID NO: 4, including the thymidine at position 171, labeled with a detectable label selected from the group consisting of a fluorescent compound, a chemiluminescent (chromophore) compound, and an enzyme, wherein the composition is used to detect ARVD/C associated mutant TMEM43.

* * * * *